(12) United States Patent
Eisenbach-Schwartz et al.

(10) Patent No.: US 7,399,740 B2
(45) Date of Patent: *Jul. 15, 2008

(54) POLY-GLU,TYR FOR NEUROPROTECTIVE THERAPY

(75) Inventors: Michal Eisenbach-Schwartz, Rehovot (IL); Ester Yoles, D.N. Nahal Sorek (IL); Ehud Hauben, Hadera (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 153 days.

This patent is subject to a terminal disclaimer.

(21) Appl. No.: 10/807,414

(22) Filed: Mar. 24, 2004

(65) Prior Publication Data

US 2004/0248802 A1 Dec. 9, 2004

Related U.S. Application Data

(63) Continuation-in-part of application No. 09/893,344, filed on Jun. 28, 2001, now Pat. No. 6,835,711, and a continuation-in-part of application No. PCT/IL2004/000008, filed on Jan. 6, 2004, and a continuation-in-part of application No. PCT/IL02/00979, filed on Dec. 5, 2002.

(60) Provisional application No. 60/527,772, filed on Dec. 9, 2003.

(51) Int. Cl.
*A61K 38/02* (2006.01)
(52) U.S. Cl. ............................................. 514/2; 514/12
(58) Field of Classification Search ........................ None
See application file for complete search history.

(56) References Cited

U.S. PATENT DOCUMENTS 6,835,711 B2 * 12/2004 Eisenbach-Schwartz et al. . 514/2
2003/0003082 A1   1/2003 Eisenbach-Schwartz et al.

FOREIGN PATENT DOCUMENTS

| WO | 99/34827 A1 | 7/1999 |
|---|---|---|
| WO | WO 03/002140 A1 | 1/2003 |
| WO | WO03/047500 A2 | 6/2003 |
| WO | WO 03/047500 A2 | 6/2003 |
| WO | WO2004/060266 A2 | 7/2004 |
| WO | WO2005/055920 A2 | 6/2005 |

OTHER PUBLICATIONS

Bussiere et al. 2001. In Functional Neurobiology of Aging, Hof and Mobbs (Eds.). pp. 77-84.*
Kemperman 2002. Journal of Neuroscience 22:635-638.*
Orr 2001. Genes and Development 15:925-932.*
Cecil Textbook of Medicine, 2000, pp. 2092-2109.*
Jackowski 1995. British Journal of Neurosurgery 9:303-317.*
Al-Chalabi et al. 2000. Current Opinion in Neurology 13:397-405.*
Cady et al, Response of Murine γδ T Cells to the Synthetic Polypeptide Poly-Glu$^{50}$Tyr$^{50}$, *J Immunol* 165(4):1790-1798 (2000).
Drach et al, "Suppressive effect of synthetic polypeptide GT on the induction of delayed-type hypersensitivity to a complex GT + methylated bovine serum albumin", *Anriales D'Immunologie*, France 131D(3):299-307 (1980).
Havenith et al, "T Cell Priming In Situ by Intratracheally Instilled Antigen-pulsed Dendritic Cells", *Am J Respir Cell Mol Biol* 9(5):484-488 (1993).
Lei et al, "Regulation of Immune Responses by I-J Gene Products; III. GT-specific Suppressor Factor is Composed of Separate I-J and Idiotype-bearing Chains", *J Immunol* 130(3):1274-1279 (1983).
Vidovic et al, "Recessive T Cell Response to Poly (Glu$^{50}$Tyr$^{50}$) Possibly Caused by Self Tolerance", *J Immunol* 134(6):3563-3568 (1985).
Hauben et al, (Sep. 1, 2000) "Passive or Active Immunization with Myelin Basic Protein Promotes Recovery from Spinal Cord Contusion," The Journal of Neuroscience 20(17): 6421-6430.
Hauben et al, (Aug. 2001) "Posttraumatic Therapeutic Vaccination with Modified Myelin Self-Antigen Prevents Complete Paralysis While Avoiding Autoimmune Disease," The Journal of Clinical Investigation 108(4): 591-599.
Fisher et al, (Jan. 1, 2001) "Vaccination for Neuroprotection in the Mouse Optic Nerve: Implications for Optic Neuropathies," The Journal of Neuroscience 21(1): 136-142.
Schori et al, (Mar. 13, 2001) "Vaccination for Protection of Retinal Ganglion Cells Against Death from Glutamate Cytotoxicity and Ocular Hypertension: Implications for Glaucoma," PNAS 98)6): 3398-3403.
Sucher et al, (1997) "Molecular Basis of Glutamate Toxicity in Retinal Ganglion Cells," Vision Res. 37(24): 3483-3493.
Schori et al,(2001) "T-Cell Based Immunity Counteracts the Potential Toxicity of Glutamate in the Central Nervous System," Journal of Neuroimmunology. 119(2): 199-204.
Stedman's Medical Dictionary (2002), Physicians' Desk Reference, Medical Economics Company Inc.
Angelov et al, "Therapeutic vaccine for acute and chronic motor neuron diseases: implications for amyotrophic lateral sclerosis", *Proc Natl Acad Sci USA* 100(8):4790-4795 (2003).
Debré et al, "Genetic control of specific immune suppression. II. H-2-linked dominant genetic control of immune suppression by the random copolymer L-glutamic acid$^{50}$-L-tyrosine$^{50}$ (GT)", *J Exp Med* 142(6):1447-1454 (1975).
Hirschberg et al, "Accumulation of passively transferred primed T cells independently of their antigen specificity following central nervous system trauma", *J Neuroimmunol* 89(1-2):88-96 (1998).

(Continued)

*Primary Examiner*—Robert C. Hayes
*Assistant Examiner*—Daniel E. Kolker
(74) *Attorney, Agent, or Firm*—Browdy and Neimark

(57) ABSTRACT

Methods and compositions are provided for preventing or inhibiting neuronal degeneration, or for promoting nerve regeneration, in the central nervous system (CNS) or peripheral nervous system (PNS), or for protecting nerves from glutamate toxicity, which comprises administering to an individual in need thereof an effective amount of the copolymer poly-Glu,Tyr.

11 Claims, 14 Drawing Sheets

OTHER PUBLICATIONS

Kipnis et al, "T cell immunity to copolymer 1 confers neuroprotection on the damaged optic nerve: possible therapy for optic neuropathies,", *Proc Natl Acad Sci USA* 97(13):7446-7451 (2000).

Kipnis et al, "Myelin specific Th1 cells are necessary for post-traumatic protective autoimmunity", *J Neuroimmunol* 130(1-2):78-85 (2002).

Kipnis et al, "Neuroprotective autoimmunity: naturally occurring $CD4^+CD25^+$ regulatory T cells suppress the ability to withstand injury to the central nervous system", *Proc Natl Acad Sci USA* 99(24):15620-15625 (2002).

Moalem et al, "Autoimmune T cells protect neurons from secondary degeneration after central nervous system axotomy", *Nat Med* 5(1):49-55 (1999).

Schwartz et al, "Protective autoimmunity: regulation and prospects for vaccination after brain and spinal cord injuries", *Trends Mol Med* 7(6):252-258 (2001).

Seo et al, "Activation of murine epidermal $V\gamma5/V\delta1$-$TCR^+$ T cell lines by Glu-Tyr polypeptides", *J Invest Dermatol* 116(6):880-885 (2001).

Yoles et al, "Protective autoimmunity is a physiological response to CNS trauma", *J Neurosci* 21(11):3740-3748 (2001).

* cited by examiner

MK-801 + YE DAY 1 - INPUT 1 MK 801 + PBS

INPUT 4

POLY-GLU,TYR FOR NEUROPROTECTIVE THERAPY

CROSS-REFERENCE TO RELATED APPLICATIONS

The present application is a continuation-in-part of application Ser. No. 09/893,344, filed Jun. 28, 2001, now U.S. Pat. No. 6,835,711 and is a continuation-in-part of International Application No. PCT/IL2004/000008, filed Jan. 6, 2004, in which the United States is designated, and is a continuation-in-part of International Application No. PCT/IL02/00979, filed Dec. 5, 2002, in which the United States is designated, and is a non-provisional of the Provisional Application No. 60/527,772, filed Dec. 9, 2003, the entire contents of each and all these applications being hereby incorporated by reference herein in their entirety as if fully disclosed herein.

FIELD OF THE INVENTION

The present invention relates to compositions and methods for the promotion of nerve regeneration or prevention or inhibition of neuronal degeneration to ameliorate the effects of injury or disease of the nervous system (NS). In particular, the invention relates to compositions comprising poly-Glu, Tyr to protect nerves from glutamate toxicity, to promote nerve regeneration or to prevent or inhibit neuronal degeneration caused by injury or disease of nerves within the central nervous system (CNS) or peripheral nervous system (PNS) of a human subject.

ABBREVIATIONS: ALS: amyotrophic lateral sclerosis; CFA: complete Freund's adjuvant; CNS: central nervous system; IOP: intraocular pressure; MBP: myelin basic protein; MCA: middle cerebral artery; NS: nervous system; NSS: neurological severity scores; OP: organophosphate; PBS: phosphate-buffered saline; pEY: Poly-Glu,Tyr; PNS: peripheral nervous system; Poly-Glu,Tyr: a random heterocopolymer of L-glutamic acid and L-tyrosine; RGC: retinal ganglion cells; SC: subcutaneously; Teff: T effector cells; Treg: T regulatory cells.

BACKGROUND OF THE INVENTION

The nervous system comprises the central (CNS) and the peripheral nervous system (PNS). The CNS is composed of the brain spinal cord and visual system; the PNS consists of all of the other neural elements, namely the nerves and ganglia outside of the brain and spinal cord.

Damage to the nervous system may result from a traumatic injury such as penetrating trauma or blunt trauma, or a disease or disorder including, but not limited to, Alzheimer's disease, Parkinson's disease, Huntington's disease, amyotrophic lateral sclerosis (ALS), diabetic neuropathy, senile dementia, stroke and ischemia.

Maintenance of CNS integrity is a complex "balancing act" in which compromises are struck with the immune system. In most tissues, the immune system plays an essential part in protection, repair, and healing. In the CNS, because of its unique immune privilege, immunological reactions are relatively limited. A growing body of evidence indicates that the failure of the mammalian CNS to achieve functional recovery after injury is a reflection of an ineffective dialog between the damaged tissue and the immune system. For example, the restricted communication between the CNS and blood-borne macrophages affects the capacity of axotomized axons to regrow; transplants of activated macrophages can promote CNS regrowth.

Activated T cells have been shown to enter the CNS parenchyma, irrespective of their antigen specificity, but only T cells capable of reacting with a CNS antigen seem to persist there (Hickey et al, 1991). T cells reactive to antigens of CNS white matter, such as myelin basic protein (MBP), can induce the paralytic disease experimental autoimmune encephalomyelitis (EAE) within several days of their inoculation into naive recipient rats (Ben-Nun, 1981). Anti-MBP T cells may also be involved in the human disease multiple sclerosis (Ota et al., 1990). However, despite their pathogenic potential, anti-MBP T cell clones are present in the immune systems of healthy subjects (Pette et al, 1990). Activated T cells, which normally patrol the intact CNS, transiently accumulate at sites of central nervous system white matter lesions (Hirschberg et al, 1998).

A catastrophic consequence of CNS injury is that the primary damage is often compounded by the gradual secondary loss of adjacent neurons that apparently were undamaged, or only marginally damaged, by the initial injury. The primary lesion causes changes in extracellular ion concentrations, elevation of amounts of free radicals, release of neurotransmitters, depletion of growth factors, and local inflammation. These changes trigger a cascade of destructive events in the adjacent neurons that initially escaped the primary injury. This secondary damage is mediated by activation of voltage-dependent or agonist-gated channels, ion leaks, activation of calcium-dependent enzymes such as proteases, lipases and nucleases, mitochondrial dysfunction and energy depletion, culminating in neuronal cell death. The widespread loss of neurons beyond the loss caused directly by the primary injury has been called "secondary degeneration."

One of the most common mediators which cause self-propagation of the diseases even when the primary risk factor is removed or attenuated is glutamate, an excitatory amino acid capable of displaying dual activity: playing a pivotal role in normal CNS functioning as an essential neurotransmitter, but becoming toxic when its physiological levels are exceeded. Elevation of glutamate has been reported in many CNS disorders. In its role as an excitotoxic compound, glutamate is one of the most common mediators of toxicity in acute and chronic (including optic nerve degeneration in glaucoma) degenerative disorders (Pitt et al., 2000). Endogenous glutamate has been attributed to the brain damage occurring acutely after status epilepticus, cerebral ischemia or traumatic brain injury. It may also contribute to chronic neurodegeneration in such disorders as ALS and Huntington's chorea.

Intensive research has been devoted to attenuating the cytotoxic effect of glutamate by the use of locally acting drugs, such as N-methyl-D-aspartate (NMDA)-receptor antagonists. Conventional therapy of this type is often unsatisfactory, however, as in neutralizing the toxic effect it is likely to interfere with the physiological functioning. In humans, such compounds have psychotropic and other side effects that make them unsuitable as therapeutic agents. They also have the disadvantage of interfering with the essential physiological functioning of glutamate as a ubiquitous CNS neurotransmitter. Because glutamate activity is essential for normal physiological functioning, yet is potentially devastating after acute injury or in chronic CNS disorders, any attempt to neutralize its harmful effect must do so without eliminating its essential activity at other sites in the body.

Another tragic consequence of CNS injury is that neurons in the mammalian CNS do not undergo spontaneous regeneration following an injury. Thus, a CNS injury causes permanent impairment of motor and sensory functions.

Spinal cord lesions, regardless of the severity of the injury, initially result in a complete functional paralysis known as spinal shock. Some spontaneous recovery from spinal shock may be observed, starting a few days after the injury and tapering off within three to four weeks. The less severe the insult, the better the functional outcome. The extent of recovery is a function of the amount of initially undamaged tissue minus the loss due to secondary degeneration. Recovery from injury would be improved by neuroprotective treatment that could reduce secondary degeneration. For example, alleviation of the effect of glutamate is a frequent target of neuroprotective drug development. Among the drugs which are being developed for this purpose are N-methyl-D-aspartate (NMDA)-receptor or alpha-amino-3-hydroxy-5-methyl-4-isoxazole-propionic acid (AMPA)-receptor antagonists. These drugs will inevitably have severe side effects as they interfere with the functioning of NMDA and AMPA receptors, which are crucial for normal CNS activity. One of the most intensely studied NMDA-receptor antagonist is MK-801 (dizocilpine), which provides effective neuroprotection but with severe side effects. In animal models of cerebral ischemia and traumatic brain injury, NMDA and AMPA receptor antagonists protect against acute brain damage and delayed behavioral deficits. Such compounds are undergoing testing in humans, but therapeutic efficacy has yet to be established. Other clinical conditions that may respond to drugs acting on glutamatergic transmission include epilepsy, amnesia, anxiety, hyperalgesia and psychosis (Meldrum, 2000).

In the laboratory of the present inventors, it has recently been discovered that activated T cells that recognize an antigen of the NS of the patient confer neuroprotection. Reference is made to U.S. application Ser. Nos. 09/218,277 and 09/314,161 and PCT Publication WO 99/60021, the entire contents of which is hereby incorporated herein by reference. More specifically, T cells reactive to MBP were shown to be neuroprotective in rat models of partially crushed optic nerve (see also Moalem et al, 1999) and of spinal cord injury (see also Hauben et al, 2000a). Until recently, it had been thought that immune cells do not participate in NS repair. Furthermore, any immune activity in the context of CNS damage was traditionally considered detrimental for recovery. It was quite surprising to discover that NS-specific activated T cells could be used to protect nervous system tissue from secondary degeneration which may follow damage caused by injury or disease of the CNS or PNS. The mechanism of action of such NS-specific T cells has yet to be discovered, but the massive accumulation of exogenously administered T cells at the site of CNS injury suggests that the presence of T cells at the site of injury plays a prominent role in neuroprotection. It appears, however, that the accumulation, though a necessary condition, is not sufficient for the purpose, as T cells specific to the non-self antigen ovalbumin also accumulate at the site, but have no neuroprotective effect (Hirschberg et al, 1998).

In addition to the NS-specific activated T cells, the above-referenced US applications and PCT publication WO 99/60021 disclose that therapy for amelioration of effects of injury or disease of NS can be carried out also with a natural or synthetic NS-specific antigen antigen such as MAG, S-100, β-amyloid, Thy-1, P0, P2, a neurotransmitter receptor, and preferably human MBP, human proteolipid protein (PLP), and human oligodendrocyte glycoprotein (MOG), or with a peptide derived from an NS-specific antigen such as a peptide comprising amino acids 51-70 of MBP or amino acids 35-55 of MOG.

More recently, it has been discovered in the laboratory of the present inventors that a high molecular weight synthetic basic random copolymer consisting of L-Ala, L-Glu, L-Lys and L-Tyr residues with an average molar fraction of 0.141, 0.427, 0.095 and 0.338, designated Copolymer 1 or Cop 1 and being the active ingredient of COPAXONE® (Teva Pharmaceuticals Ltd., Israel), a medicament for the treatment of multiple sclerosis, is able to prevent or inhibit neuronal degeneration, or to promote nerve regeneration, in the CNS or PNS, as well as to protect CNS cells from glutamate toxicity. Reference is made to copending U.S. application Ser. No. 09/765,301 and No. 09/765,644, and PCT International Publications WO 01/52878 and WO 01/93893, the entire contents of which is hereby incorporated herein by reference. More specifically, Cop 1-specific activated T cells were shown to accumulate in both injured and non-injured neuronal tissues and to be protective in the injured optic nerve against the destructive effect of secondary degeneration, and immunization with Cop 1 was shown to protect against glutamate toxicity.

Oral administration of autoantigen in order to obtain "oral tolerance" has been disclosed for the treatment of various autoimmune diseases. For example, EP 359 783 discloses the oral administration of MBP for the treatment of multiple sclerosis. PCT International Publications WO 91/12816, WO 91/08760 and WO 92/06704 all disclose the treatment of other autoimmune diseases using the oral tolerance method with a variety of autoantigens. Treatment of multiple sclerosis by ingestion or inhalation of Cop 1, to achieve suppression of the autoimmune T cell response to myelin antigens, has been disclosed in WO 98/30227.

The copolymer poly-Glu,Tyr, formerly often termed polyGT and hereinafter called poly-Glu,Tyr, poly-YE or pEY, is a random heterocopolymer of L-glutamic acid and L-tyrosine, with a capacity to elicit strong immune response in certain mouse strains (Vidovic et al., 1985; Vidovic and Matzinger, 1988). More than 20 years ago it was shown that several inbred as well as congenic resistant strains of mice, which fail to respond to pYE, were shown to develop specific plaque-forming cell (PFC) responses when stimulated by YE complexed to an immunogenic carrier such as methylated bovine serum albumin (MBSA), and that pre-immunization with pEY has a tolerogenic effect on the response to YE-MBSA in some mouse strains and this tolerance can be transferred to normal, syngeneic recipients by spleen cells or thymocytes of EY-primed animals (Debre et al., 1975). More recently, the activation of murine Vy5NV61-TCR(+) epidermal T cell lines by Glu-Tyr polypeptides has been studied. The physiologic role of γδ-T-cell-receptor (TCR)-bearing cells and the TCR ligands that they recognize is still poorly understood. One possible antigen for γδ-TCR(+) cells is poly-Glu,Tyr, because poly-Glu,Tyr-reactive γδ-TCR(+) hybridoma cells were produced from poly-Glu,Tyr-immunized mice (Seo et al., 2001).

None of these publications relates to, or suggests, the use of poly-Glu,Tyr for neuroprotection.

Citation or identification of any reference in this section or any other part of this application shall not be construed as an admission that such reference is available as prior art to the invention.

SUMMARY OF THE INVENTION

It has now been found by the present inventors that poly-Glu,Tyr can protect nerves from glutamate toxicity and from undergoing secondary degeneration following spinal cord contusion, and also following chronic elevation of intraocular pressure and cerebral ischemia. It was further found that active immunization with poly-Glu,Tyr attenuates neuronal degeneration induced by glutamate toxicity or by mechanical injury to the spinal cord.

The present invention thus relates to a method for preventing or inhibiting neuronal degeneration, or for promoting nerve regeneration, in the CNS or PNS, or for protecting nerves from glutamate toxicity, which comprises administering to an individual in need thereof an effective amount of poly-Glu,Tyr.

The present invention also provides pharmaceutical compositions comprising a therapeutically effective amount of poly-Glu,Tyr and methods for using such compositions to promote nerve regeneration or to prevent or inhibit neuronal degeneration in the CNS or PNS, or for protecting nerves from glutamate toxicity, in an amount which is effective to ameliorate the effects of an injury or disease of the NS.

As used herein, the term "neuroprotection" refers to the prevention or inhibition of degenerative effects of injury or disease in the NS, including protection from the secondary neurodegenerative effects which persist even when the primary risk factor is removed or attenuated. This includes protection of both white matter and gray matter.

BRIEF DESCRIPTION OF THE DRAWINGS

FIG. 4B shows that rats immunized with poly-Glu,Tyr (triangles) recovered significantly better than the control PBS/CFA (squares) and PBS-treated (diamonds) rats.

FIG. 16B shows that the effect was even more significant in the co-cultures of Teff and TregYE to which poly-Glu,Tyr was added (TregYE+YE), as shown by the significantly higher Teff proliferation.

DETAILED DESCRIPTION OF THE INVENTION

Figure 1:
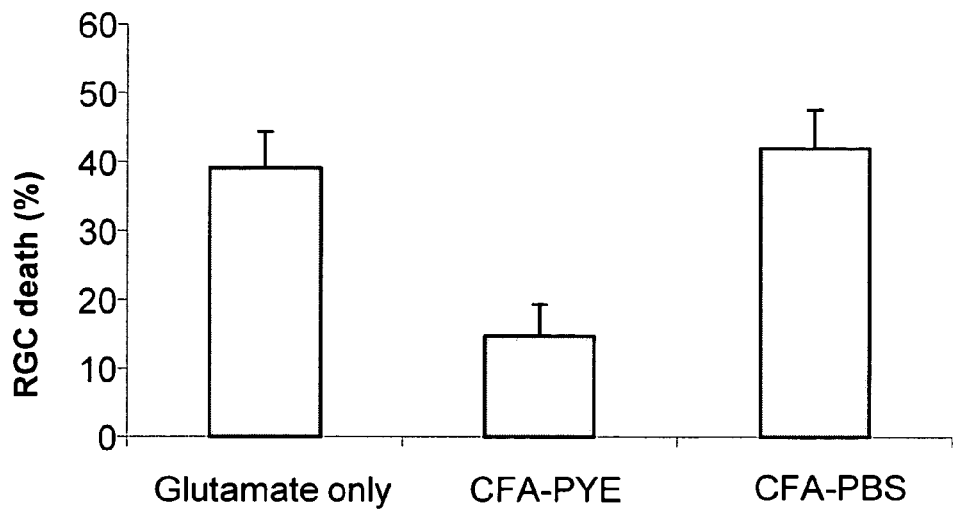
FIG. 1 is a graph showing how immunization with polyYE attenuates significantly retinal ganglion cells (RGCs) death induced by glutamate. The number of labeled (surviving) RGC/mm² in retinas excised from C57BL/6J mice who had been immunized with an emulsion of poly-Glu,Tyr in complete Freund's adjuvant (CFA-PYE) or with PBS in CFA (CFA-PBS) or non-treated mice (glutamate only), 7 days prior to intravitreal glutamate injection, and 7 days later, was counted. Bars represent mean ±sem of percentage of RGC death compared to the naïve retina.

As used herein, the terms "poly-YE", "polyYE", "pYE", and "poly-Glu,Tyr" are each used interchangeably to denote a random copolymer comprising residues of L-glutamic acid and L-tyrosine. Any poly-Glu,Tyr presently available or to be discovered in the future is encompassed by the present invention, but most preferred is the random copolymer poly-Glu:Tyr 1:1, most preferably the sodium salt of poly-Glu:Tyr 1:1, mol wt 20,000-50,000, preferably 20,000-40,000 Da.

The compositions of the invention comprising poly-Glu,Tyr may be used to promote nerve regeneration or to prevent or inhibit secondary degeneration which may otherwise follow primary NS injury, e.g., closed head injuries and blunt trauma, such as those caused by participation in dangerous sports, penetrating trauma, such as gunshot wounds, hemorrhagic stroke, ischemic stroke, glaucoma, cerebral ischemia, or damages caused by surgery such as tumor excision. In addition, such compositions may be used to ameliorate the effects of disease that result in a degenerative process, e.g., degeneration occurring in either gray or white matter (or both) as a result of various diseases or disorders, including, without limitation: diabetic neuropathy, senile dementias, Alzheimer's disease, Parkinson's disease, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases including, but not limited to, uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia vera, IgA and IgG gammapathies, complications of various drugs (e.g., metronidazole) and toxins (e.g., alcohol or organophosphates), Charcot-Marie-Tooth disease, ataxia telangiectasia, Friedreich's ataxia, Guillain-Barre syndrome, amyloid polyneuropathies, adrenomyelo-neuropathy, Giant axonal neuropathy, Refsum's disease, Fabry's disease, lipoproteinemia, etc.

In light of the findings with respect to the glutamate protective aspect of the present invention, other clinical conditions that may be treated in accordance with the present invention include epilepsy, amnesia, anxiety, hyperalgesia, psychosis, seizures, abnormally elevated intraocular pressure, oxidative stress, and opiate tolerance and dependence. In addition, the glutamate protective aspect of the present invention, i.e., treating injury or disease caused or exacerbated by glutamate toxicity, can include post-operative treatments such as for tumor removal from the CNS and other forms of surgery on the CNS.

In view of the fact that poly-Glu,Tyr immunization has been surprisingly found useful in protecting against glutamate toxicity, it is expected that poly-Glu,Tyr treatment in accordance with the present invention will be effective in the treatment of the above listed conditions not only in a late phase when myelin is being affected, but also in the early stages in which the neurons are being attacked by factors which cause an elevation in glutamate levels to toxic levels. Thus, the present invention is useful for any indication, i.e., chronic or acute neurodegeneration, which is caused or exacerbated by an elevation in glutamate levels, including the early stages of ischemic stroke, Alzheimer's disease, etc.

The present invention provides a method for preventing or inhibiting neuronal degeneration, or for promoting nerve regeneration, in the central nervous system (CNS) or peripheral nervous system (PNS), or for protecting nerves from glutamate toxicity, which comprises administering to an individual in need thereof an amount of poly-Glu,Tyr effective to prevent or inhibit neuronal degeneration, or to promote nerve regeneration, in the CNS or PNS, or to protect nerves from glutamate toxicity.

In one embodiment, the compositions of the invention comprising poly-Glu,Tyr are used in a method to promote nerve regeneration or to prevent or inhibit secondary degeneration which may otherwise follow primary CNS injury.

In one preferred embodiment, the present invention relates to a method for reducing neuronal degeneration caused by the neurodegenerative effects of an injury, disease, disorder or condition in the CNS or PNS of the individual in need, which comprises administering poly-Glu,Tyr in an amount effective to reduce the neurodegeneration caused by said injury, disease, disorder or condition.

In a preferred embodiment, the individual in need is one suffering from secondary neuronal degeneration resulting from an injury that has caused primary neuronal damage.

Thus, in a preferred embodiment, the method of the present invention comprises administering poly-Glu,Tyr to an individual in need for treating neurodegenerative effects caused by a primary injury, in an amount effective to reduce neuronal degeneration caused by said primary injury. The primary injury includes spinal cord injury, closed head injury, blunt trauma such as those caused by participation in dangerous sports, penetrating trauma such as gunshot wounds, hemorrhagic stroke, ischemic stroke, cerebral ischemia, optic nerve injury, myocardial infarction and injury caused by surgery such as tumor excision.

In one more preferred embodiment, the injury is myocardial infarction. In another more preferred embodiment, the injury is spinal cord injury. I a still more preferred embodiment, the injury is ischemic stroke.

In another preferred embodiment, the method of present invention comprises administering poly-Glu,Tyr to an individual in need for treating neurodegenerative effects caused by a condition, disorder or disease associated with the eye, such as non-arteritic optic neuropathy, age-related macular degeneration, a retinal disorder or a disease associated with elevated intraocular pressure, e.g. glaucoma, in an amount effective to reduce neuronal degeneration caused by said condition, disorder or disease associated with the eye. In a most preferred embodiment of the invention, poly-Glu,Tyr is administered for preventing or reducing optic nerve degeneration in glaucoma patients.

In another preferred embodiment, the present invention provides a method for treating an injury, disease, disorder or condition caused or exacerbated by glutamate toxicity, which comprises administering poly-Glu,Tyr to the individual in need in an amount effective to ameliorate the neurodegeneration caused or exacerbated by glutamate toxicity.

According to this embodiment, the disease, disorder or condition caused or exacerbated by glutamate toxicity may be a neurodegenerative disease such as a senile dementia of both Alzheimer's type and non-Alzheimer's type, Parkinson's disease, facial nerve (Bell's) palsy, glaucoma, Huntington's chorea, a motor neurone disease such as amyotrophic lateral sclerosis (ALS), Alper's disease, Batten disease, Cockayne syndrome, Lewy body disease, Guillain-Barre syndrome, and a prion disease such as Creutzfeldt-Jakob disease.

Thus, poly-Glu,Tyr may be used to ameliorate the effects of disease or disorder that result in a degenerative process, e.g. degeneration occurring in either gray or white matter (or both) as a result of the chronic neurodegenerative diseases recited in the previous paragraph or as a result of further diseases, disorders and conditions. For example, in a patient suffering from Huntington's disease, poly-Glu,Tyr is administered in an amount therapeutically effective to reduce disease progression and/or to protect the patient from neurodegeneration and/or from glutamate toxicity. In a patient suffering from a motor neurone disease, poly-Glu,Tyr is administered in an amount effective to reduce disease progression, and/or to protect the patient from motor nerve degeneration and/or from glutamate toxicity. In a particular embodiment, the motor neurone disease is amyotrophic lateral sclerosis (ALS) and poly-Glu,Tyr may be administered to the ALS patient as sole therapy or in combined therapy with Riluzole. In a patient suffering from Alzheimer's disease, poly-Glu,Tyr is administered in an amount therapeutically effective to reduce disease progression and/or to protect the patient from neurodegeneration and/or from glutamate toxicity and/or to reduce memory loss associated with the disease.

In another embodiment of the invention, poly-Glu,Tyr may be used for the treatment of a peripheral neuropathy. Peripheral neuropathy, a general term referring to disorders of the PNS, can be associated with poor nutrition, a number of diseases, and pressure or trauma. Known etiologies include complications of other diseases, mainly diabetes. Nearly 60% of all people with diabetes suffer from peripheral neuropathy. Peripheral neuropathy can be classified by where it occurs in the body: nerve damage that occurs in one area of the body is called mononeuropathy, and in many areas, polyneuropathy. It can also be categorized by cause such as diabetic neuropathy and nutritional neuropathy. When a cause cannot be identified, the condition is called idiopathic neuropathy.

According to the present invention, poly-Glu,Tyr may be used for the treatment of peripheral neuropathies, both mononeuropathies and polyneuropathies, caused by or associated with many diseases, disorders and conditions.

Examples of peripheral neuropathies that may be treated with poly-Glu,Tyr according to the invention include, but are not limited to, adrenomyeloneuropathy, alcoholic neuropathy (associated with chronic alcoholism), amyloid neuropathy or polyneuropathy (caused by amyloidosis), axonal neuropathy, chronic sensory ataxic neuropathy associated with Sjogren's syndrome, diabetic neuropathy, an entrapment neuropathy or nerve compression syndrome such as carpal tunnel syndrome or a nerve root compression that may follow cervical or lumbar intervertebral disc herniation, giant axonal neuropathy, hepatic neuropathy (associated with viral hepatitis, liver cirrhosis, or biliary cirrhosis), ischemic neuropathy, nutritional polyneuropathy (due to nutritional deficits such as vitamin, e.g. vitamin B6, B12 deficiency, malabsorption syndromes and alcoholism), porphyric polyneuropathy (a severe form associated with various types of porphyria), toxic neuropathy (caused by toxins such as organophosphates), uremic polyneuropathy (caused by the uremia of chronic renal failure), a neuropathy associated with a disease or disorder such as acromegaly, ataxia telangiectasia, Charcot-Marie-Tooth disease, chronic obstructive pulmonary diseases, Fabry's disease, Friedreich ataxia, Guillain-Barré syndrome (an acute inflammatory polyneuropathy), hypoglycemia, IgG or IgA monoclonal gammopathy (non-malignant or associated with multiple myeloma or with osteosclerotic myeloma), lipoproteinemia, polycythemia vera, Refsum's syndrome, Reye's syndrome, Sjogren-Larsson syndrome, or a polyneuropathy associated with various drugs (e.g., nitrofurantoin and metronidazole), or a polyneuropathy associated with hypoglycemia, with infections such as HIV infection, or with cancer (radiation treatments, chemotherapy or the cancer can be the cause of the nerve damage).

As mentioned before, other clinical conditions that may be treated in accordance with the present invention include epilepsy, amnesia, anxiety, hyperalgesia, psychosis, seizures, abnormally elevated intraocular pressure, oxidative stress, and opiate tolerance and dependence.

Thus, in another preferred embodiment of the invention, poly-Glu,Tyr is used for the treatment of a psychosis or psychiatric disorder selected from the group consisting of an anxiety disorder, a mood disorder, schizophrenia or a schizophrenia-related disorder, drug use and drug dependence and withdrawal, and a memory loss or cognitive disorder.

The psychosis or psychiatric disorder that can be treated according to the invention is selected from: (i) anxiety disorders, that include phobic disorders, obsessive-compulsive disorder, post-traumatic stress disorder (PTSD), acute stress disorder and generalized anxiety disorder; (ii) mood disorders, that include depression, dysthymic disorder, bipolar disorders and cyclothymic disorder; (iii) schizophrenia and related disorders such as brief psychotic disorder, schizophreniform disorder, schizoaffective disorder and delusional disorder; (iv) dependence on or withdrawal from a drug of abuse such as alcoholism, opiate dependence, cocaine dependence, amphetamine dependence, hallucinogen dependence, and phencyclidine use; and (v) memory loss disorders such as amnesia or memory loss associated with Alzheimer's type dementia or with non-Alzheimer's type dementia, e.g. multi-infarct dementia or memory loss associated with Parkinson's disease, Huntington's disease, Creutzfeld-Jakob disease, head trauma, HIV infection, hypothyroidism and vitamin B12 deficiency, and cognitive deficits in children or in adults associated with psychosis, drug-induced psychosis, stroke, and sexual dysfunction. The cognitive problems may be related to thinking, reasoning, problem solving, visual perception and auditory processing problems, including difficulties in spatial cognition and orientation, e.g. object localization, spatial memory, awareness of position and place. In this aspect, poly-Glu,Tyr may also be useful for improving memory (both short term and long term) and learning ability.

In one preferred embodiment, poly-Glu,Tyr is used for treatment of schizophrenia; in another embodiment, for treatment of depression; and in another embodiment, for improving memory in patients suffering from memory loss associated with a disease or disorder as defined in (v) in the previous paragraph.

In another preferred embodiment of the invention, poly-Glu,Tyr may be used for treatment of individuals exposed to neurotoxins, e.g. nerve gases such as organophosphate nerve gases, for example, sarin.

In another preferred embodiment of the invention, poly-Glu,Tyr may be used in post-operative treatments such as for tumor removal from the CNS and other forms of surgery on the CNS, that may be caused or exacerbated by glutamate toxicity.

Acute and/or chronic injuries to the adult CNS in the brain, spinal cord and the visual system lead to the irreversible loss of function resulting from the loss of neurons and the very scarce neurogenesis in the adult CNS. The injury is often compounded by the inability of nerve cells within the CNS to regenerate damaged axons, eventually inducing degeneration of the entire neuron. In addition, regardless of the initial cause of the primary injury, the dying cells cause accumulation of neural toxic molecules at the site of the injury. Due to failure to cope with the accumulating toxic molecules, neurons and glial cells adjacent to the site of the primary injury die, leading to additional progressive neuronal loss—a phenomenon known as secondary degeneration. The volume of tissue destroyed by secondary degeneration is usually larger than that caused by the initial injury. The use of a neuroprotective agent that can mitigate the adversities associated with secondary neurodegeneration could preserve nerve function. Towards minimizing neuronal loss (neuroprotection), several approaches have been adopted in the past, with the most common approach targeting the risk factors in an attempt to neutralize or inhibit their actions. Unfortunately, these therapeutic strategies showed marginal efficacy in human subjects and with concomitant severe side effects. The failure of agents with discrete singular mechanism of action argues for a multi-pronged approach.

Injury to the CNS triggers the immediate death of injured neurons, and this is inevitably followed by a series of destructive processes, collectively termed secondary degeneration (Yoles and Schwartz, 1998), which result in the gradually spreading degeneration and death of initially undamaged adjacent neural cells. The processes of secondary degeneration are mediated mainly by destructive self-compounds that emanate from the directly damaged neurons and render the extracellular environment hostile to recovery. Until very recently, the prevailing view was that the CNS, being an immune-privileged site, cannot benefit from immune intervention and that all immune activity is detrimental. Studies by our group showed, however, that one way in which the hostility of the environment at the damaged site can be circumvented is by eliciting a systemic defensive activity that homes to the lesion site and helps the innate arm of the immune system to fight off the toxicity. This assistance is provided by the spontaneous recruitment of T cells specific to CNS-related self-antigens (Hauben et al., 2000b). The autoimmune T cells home to the site of the lesion and become activated there by encountering their specific antigens, which are presented to them by antigen-presenting cells (e.g. activated microglia). Thus, contrary to the prevailing belief that the immune system is always harmful to the CNS, our work suggested that the CNS withstands injurious post-injury conditions by eliciting a protective autoimmunity (Moalem et al., 1999).

Further studies by our group showed that adult rats or mice deficient in mature T cells, or deprived (as a result of immunization at birth with spinal cord homogenate) of T cells specific to self-antigens residing in the site of damage, are unable to withstand injurious conditions in the CNS (Kipnis et al., 2001; Schori et al., 2002). The T cells that participate in protection were found to possess a phenotype characteristic of Th1 cells (Kipnis et al., 2002b). These and related results led us to formulate the concept of "protective autoimmunity" as a physiological mechanism of protection against destructive self-compounds (Schwartz and Kipnis, 2001; Yoles et al., 2001). When stressed, the CNS signals to the immune system to help regulate self-compounds that have exceeded their normal physiological levels and become toxic. This recruited immune activity is in the form of autoimmune T cells directed against abundant antigens residing in the site of stress. This discovery not only challenges the way we view immune activity in the brain and thus the meaning of immune "privilege", but also changes the way we view autoimmunity: Instead of seeing autoimmunity as a "mistake" in which the body attacks its own tissues, it can be seen as the body's way of defending itself against self-enemies.

One of the self-enemies that has received a great deal of attention in the last two decades is glutamate, an amino acid pivotal for the functioning of the CNS. Yet when glutamate exceeds its normal physiological levels it is a major cause of neuronal toxicity and death. Unregulated levels of glutamate have been associated with psychogenic and neurodegenerative disorders. After it was discovered that autoimmunity helps regulate glutamate toxicity as well as other local CNS threats, it became clear that it might be possible to develop therapeutic approaches to psychogenic and neurodegenerative diseases by regulating this beneficial autoimmune response. This boosting takes the form of therapeutic vaccination using self- or self-like peptides which promote autoimmune protection without inducing autoimmune disease. Thus, our group showed that this physiological response can be boosted by injection (passive transfer) of activated autoimmune T cells (Moalem et al., 1999; Kipnis et al., 2002b; Hauben et al., 2000a) or by active vaccination with self- or self-related antigens (Hauben et al., 2001a, 2001b; Kipnis et al., 2000; Schori et al., 2001a).

Moreover, the spontaneous protective response was found to be suppressed by the constitutive presence of naturally occurring regulatory T cells (Treg) cells. Thus, nude mice replenished with splenocytes deprived of Treg are better able to withstand injurious conditions in the CNS than their matched wild-type controls or nude mice replenished with a population consisting of the full complement of spleen cells (Kipnis et al., 2002a; Schwartz and Kipnis, 2002).

The naturally occurring $CD4^+CD25^+$ cells, which comprise about 10% of the total $CD4^+$ population, are the so-called (natural) regulatory T cells (Treg). Treg cells display suppressive functions in vitro or in vivo, and were originally called suppressor T cells. Treg cells express the transmembrane protein called CD25, the a chain of the IL-2 receptor (Sakaguchi et al., 1995). $CD4^+CD25^+$ T cells are potent suppressors of the activation of both $CD4^+$ and $CD8^+$ T cells in vitro and also potent suppressors of a large number of animal models of autoimmunity, including gastritis, thyroiditis, inflammatory bowel disease and insulin-dependent diabetes mellitus. Both suppressor cytokines, such as interleukin (IL)-4, IL-10 and transforming growth factor (TGF)-β, and a cell-contact-dependent mechanism, may have a role in the suppression of the disease in vivo (Shevach, 2002).

As described above, recent evidence provided by the present inventors indicates that autoimmunity, that has long been viewed as a destructive process, is the body's endogenous response to CNS injury and its purpose is in fact beneficial. This neuroprotective autoimmunity was shown by the inventors to be inhibited by naturally occurring $CD4^+CD25^+$ cells, that suppressed an endogenous T-cell mediated neuroprotective mechanism to achieve maximal activation of autoimmunity and, therefore, to withstand injury to the CNS (Kipnis et al., 2002a).

Thus, it can be summarized that the peripheral immune response to injury is part of a natural repair mechanism of the human body. This spontaneous T cell-mediated neuroprotective immune response can be enhanced by accumulation of activated T cells at the site of injury. This may be achieved either by active immunization of the individual with a nervous tissue-specific antigen, e.g. MBP, a MBP peptide, or an altered MBP peptide, or by passive immunization with MBP-activated T cells as shown previously by the inventors (Moalem et al., 1999; Hauben et al., 2001a; WO 99/060021; WO 02/055010), or by circumventing the tissue specificity using weak antigens like Copolymer 1 or poly-Glu,Tyr, or by down-regulating the suppressive effect of the Treg cells.

It has further been unexpectedly found in accordance with the present invention that poly-Glu,Tyr down-regulates the suppressive activity of the Treg cells on the autoimmune Teff cells.

Thus, administration of poly-Glu,Tyr according to the invention follows a fundamentally different approach to nerve preservation and restoration, taking advantage of natural physiological mechanisms of protection and self-healing via the immune system. As described above, activation of the autoimmune response is part of a physiological repair mechanism following CNS damage. However, this response is restricted in the CNS by naturally-occurring Treg cells. An appropriately controlled boost to the immune response by administering poly-Glu,Tyr that down-regulates the suppressive activity of Treg on the autoreactive effector T cells, protects CNS cells from further degeneration and enhances functional recovery. This is accomplished by causing the effector T cells, which recognize their antigen at the lesion site, to home there, and activate the resident cells to eliminate self-destructive compounds that cause nerve degeneration and to secrete growth factors that may induce axonal elongation, synaptogenesis and neurogenesis.

According to the present invention, poly-Glu,Tyr is shown to down-regulate the suppressive activity of Treg cells on the Teff cells, and thus to boost the spontaneous protective activity of T cells at the site of injury or disease.

In another aspect, the present invention relates to a method for down-regulation of the suppressive activity of $CD4^+$ $CD25^+$ regulatory T cells (Treg) on $CD4^+CD25^-$ effector T cells (Teff), modulation of the immune response, modulation of the autoimmune response, protection from glutamate toxicity, or a combination thereof, in an individual suffering from a neurological, neurodegenerative or psychiatric injury, condition, disorder or disease, which comprises administering to said individual in need an amount of the copolymer poly-Glu, Tyr effective for the treatment of said neurological, neurodegenerative or psychiatric injury, condition, disorder or disease.

In still another aspect, the present invention relates to a method for conferring neuroprotection to an individual suffering from a neurological, neurodegenerative or psychiatric injury, disease, disorder or condition, which comprises administering poly-Glu,Tyr to the individual in need in an amount effective to ameliorate the neurodegeneration associated with said neurological, neurodegenerative or psychiatric injury, disease, disorder or condition.

It is envisaged by the present invention that poly-Glu,Tyr affords neuroprotective activity and broad therapeutic benefits to all injuries, diseases, disorders and conditions in the CNS and PNS defined in the present specification and in the claims, irrespective of their etiology and/or associated risk factors.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

Methods of administration of compositions containing poly-Glu,Tyr include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local. Most preferably, poly-Glu,Tyr is administered subcutaneously or topically, e.g. as eye drops.

As shown hereinafter in Section III of the Examples, poly-Glu,Tyr can be administered as eye drops both for treatment of an injury, disease or disorder associated with the eye, particularly glaucoma, and of any other CNS or PNS injury, disease or disorder, because the effect of poly-Glu,Tyr administered as eye drops is systemic.

Thus, in one preferred embodiment, the invention provides pharmaceutical compositions in the form of eye drops comprising poly-Glu,Tyr and a pharmaceutically acceptable carrier.

The compositions may be formulated for subcutaneous and parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use. Where the composition is administered by injection, an ampoule of sterile water or saline for injection can be provided so that the ingredients may be mixed prior to administration.

Pharmaceutical compositions comprising poly-Glu,Tyr may be also administered with an adjuvant in the usual manner for immunization, but preferably no adjuvant is added to the composition.

The present invention also provides a pharmaceutical kit comprising a package housing a container containing poly-Glu,Tyr, and instructions for using poly-Glu,Tyr in the treatment of an injury, condition, disease or disorder as described in the specification in order to prevent or inhibit neuronal degeneration caused by said injury, condition, disease or disorder, or to protect from glutamate toxicity.

As will be evident to those skilled in the art, the therapeutic dose of poly-Glu,Tyr to be administered to the individual in need will be determined by the physician and will depend on the injury, condition, disorder or disease to be treated, on the individual's age and health condition, on other physical parameters (e.g., gender, weight, etc.) of the individual, as well as on various other factors, e.g., whether the individual is taking other drugs. In general, the dose will be from 0.1 to 100, preferably 10-50, more preferably, 15-30, and most preferably, 20 mg poly-Glu,Tyr per person.

According to the invention, poly-Glu,Tyr may be administered as a single dose or may be repeated, preferably at 4 weeks intervals, and then at successively longer intervals, once every two months, once every three months, once every six months, etc. The course of treatment may last several months, several years or occasionally also through the lifetime of the individual, depending on the condition or disease which is being treated. In the case of a CNS injury, the treatment may range between several days to months or even years, until the condition has stabilized and there is no or only a limited risk of development of secondary degeneration. In chronic human disease such as glaucoma, Alzheimer's disease or Parkinson's disease, the therapeutic treatment in accordance with the invention may be for life.

It is envisaged by the present invention that poly-Glu,Tyr will be used as sole therapy or that it is used in conjunction with a drug commonly used for the treatment of the injury, disease, disorder or condition being treated. For example, for the treatment of ALS, the treatment may include administration of poly-Glu,Tyr together with Riluzole; for the treatment of glaucoma, the treatment may include administration of poly-Glu,Tyr together with a drug that decreases the intraocular pressure; for the treatment of ischemic stroke, the treatment may include administration of poly-Glu,Tyr together with an anti-clot drug; or before exposure to organophosphate nerve gases, the individual may receive the usual antidote treatment (e.g., atropine) followed by an anti-convulsant after exposure, e.g. midazolam.

The present invention further provides an article of manufacture comprising packaging material and a pharmaceutical composition contained within the packaging material, said pharmaceutical composition comprising poly-Glu,Tyr; and said packaging material includes a label that indicates that poly-Glu,Tyr is therapeutically effective for conferring neuroprotection to an individual suffering from a neurological, neurodegenerative or psychiatric injury, disease, disorder or condition, wherein said neurological, neurodegenerative or psychiatric injury, disease, disorder or condition is as described hereinbefore in the specification.

The following examples illustrate certain features of the present invention but are not intended to limit the scope of the present invention.

EXAMPLES

Merely for ease of explanation, the Examples of the present invention are presented as the following sections: (I) Poly-Glu,Tyr protects optic nerve from glutamate toxicity; (II) Poly-Glu,Tyr confers neuroprotection in CNS spinal cord and optic nerve crush injury models; (III) Poly-Glu,Tyr confers neuroprotection in the chronic and acute glaucoma models; (IV) Poly-Glu,Tyr circumvents the tissue specificity barrier; (V) Neuroprotective effect of poly-Glu,Tyr in stroke; (VI) Effect of poly-Glu,Tyr in induction of neurogenesis after stroke; (VII) Neuroprotective effect of poly-Glu,Tyr in ALS; (VIII) Neuroprotective effect of poly-Glu,Tyr in Huntington's disease; (IX) Effect of poly-Glu,Tyr on Treg cells; (X) Poly-Glu,Tyr is protective in the treatment of psychiatric disorders; (XI) Poly-Glu,Tyr protects against nerve gases; and (XII) Cardioprotective effect of Poly-Glu,Tyr in myocardial infarction.

The poly-Glu,Tyr used in all Examples hereinafter was the $pE^{50}Y^{50}$ of molecular weight 20,000-40,000 purchased from Sigma (St. Louis, Mo., USA, Catalog No. P-1051).

The animals used in the experiments, if not indicated differently, were supplied by the Animal Breeding Center of the Weizmann Institute of Science (Rehovot, Israel). All animals were handled according to the regulations formulated by the Institutional Animal Care and Use Committee (IACUC).

Section I

Poly-Glu,Tyr Protects Optic Nerve from Glutamate Toxicity

As described hereinbefore, glutamate toxicity was found to play a major role in triggering neurodegeneration following CNS insult regardless of the initial cause, whether acute or chronic. We use an in vivo model of glutamate toxicity for screening potential neuroprotective agents. Intraocular injection of glutamate into the eye of a mouse exposes the RGCs (the retinal neurons that project the visual information to the brain through their axons, the optic nerve, and are part of the CNS) to temporary elevation of glutamate concentration, leading to RGC death as measured 7 days later. The effectiveness of the neuroprotective agent in protecting neurons is measured by counting the surviving RGCs. This is a useful model for establishment of the drug dosages and protocols to be used in the treatment of acute and/or chronic diseases.

Materials and Methods—Section I

Animals. Mice of the C57BL/6J strain, aged 8-13 weeks, were housed in light- and temperature-controlled rooms. Prior to their use in experiments, animals were anesthetized by intraperitoneal administration of ketamine (80 mg/kg) and xylazine (16 mg/kg).

Immunization. Mice were immunized with poly-Glu,Tyr (25, 100 or 225 µg) emulsified with an equal volume of CFA containing 0.5 mg/ml *Mycobacterium tuberculosis*. The emulsion (total volume 0.1 ml) was injected subcutaneously (SC) at one site in the flank in the mice. Control mice were injected with PBS in CFA (Difco Laboratories, Detroit, Mich., USA).

Glutamate injection. The right eye of the anesthetized mouse was punctured with a 27-gauge needle in the upper part of the sclera, and a 10-µl Hamilton syringe with a 30-gauge needle was inserted as far as the vitreal body. Mice were injected with L-glutamate dissolved in saline. The left eye was not injected and served as a control.

Labeling of RGCs in mice. RGCs were labeled 72 hours before the end of the experiment. Mice were anesthetized and placed in a stereotactic device. The skull was exposed and kept dry and clean. The bregma was identified and marked. The designated point of injection was at a depth of 2 mm from the brain surface, 2.92 mm behind the bregma in the antero-posterior axis and 0.5 mm lateral to the midline. A window was drilled in the scalp above the designated coordinates in the right and left hemispheres. The neurotracer dye FluoroGold (5% solution in saline; Fluorochrome, Denver, Colo.) was then applied (1 µl, at a rate of 0.5 µl/min in each hemisphere) using a Hamilton syringe, and the skin over the wound was sutured.

Assessment of RGC survival in mice. Seven days after glutamate administration, mice were given a lethal dose of pentobarbitone (170 mg/kg). Their eyes were enucleated and their retinas were detached and prepared as flattened whole mounts in paraformaldehyde (4% in PBS). Labeled cells from 4-6 selected fields of identical size (0.7 mm 2) were counted. The selected fields were located at approximately the same distance from the optic disk (0.3 mm) to overcome the variation in RGC density as a function of distance from the optic disk. Fields were counted under the fluorescence microscope (magnification x800) by observers blinded to the treatment received by the mouse. The average number of RGCs per field in each retina was calculated.

Example 1

Immunization with Poly-Glu,Tyr in Adjuvant Protects Optic Nerve Fibers from Glutamate Toxicity In order to find out whether poly-Glu,Tyr can impart a more general neuroprotection from hostile environmental conditions caused by glutamate-induced toxicity, the following experiment was conducted.

Injection of the excitatory neurotransmitter glutamate into the vitreal body of C57BL/6J mice eye causes dose-dependent death of the cell bodies of optic nerve neurons. A previous study showed that the onset of RGC death is delayed (by more than 24 hours after glutamate injection) and is apoptotic-like.

In the present experiment, 8-week-old male C57BL/6J mice were immunized SC with 100 µg poly-Glu,Tyr emulsified in CFA, 7 days prior to glutamate injection. A group of mice immunized at the same time with PBS emulsified in CFA (to rule out a non-specific effect of the immunization) and a group of non-immunized mice served as controls. Mice in all three groups received an injection of glutamate (400 nmole) into the vitreous of the right eye. The left eye received no injection and was used as an intact control. Seven days after glutamate injection, the eyes were excised and RGC survival was determined.

The average number of RGCs per mm$^2$ counted in the intact retinas of the poly-Glu,Tyr-immunized, the PBS-immunized, and the non-immunized mice were 2796±165, 2874±197 and 2807±42, respectively, indicating that immunization had no effect on survival of RGCs in the contralateral intact eye. These average values of RGCs per mm$^2$ in intact retina in all 3 experimental groups were therefore combined and taken as 100% RGC survival (0% toxicity).

The results depicted in FIG. 1 show that immunization of the mice with poly-Glu,Tyr in CFA (CFA-PYE) significantly attenuated the glutamate-induced RGC death compared to immunization with PBS (CFA-PBS; t-test, p=0.007) or to non-immunization (t-test, p=0.01). There was no difference in RGC survival between the 2 latter groups (t-test, p=0.71).

Example 2

Figure 2:
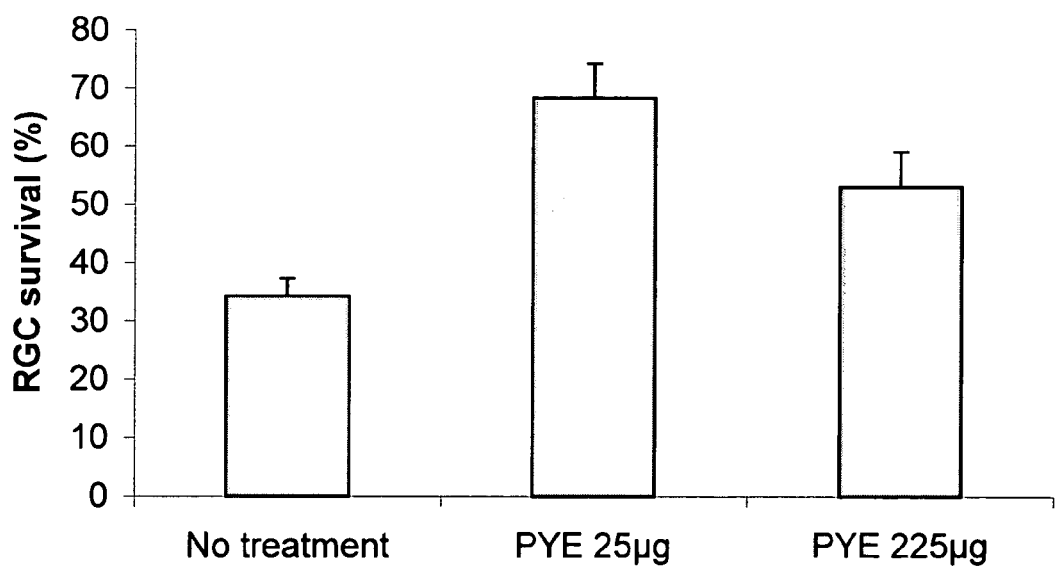
FIG. 2 shows that immunization with different doses of poly-Glu,Tyr (PYE 25 and 225 μg) without adjuvant protects mice RGCs from glutamate toxicity. Bars represent mean ±sem of percentage of RGC survival compared to the naïve retina.

Immunization with Poly-Glu,Tyr without Adjuvant Protects Optic Nerve Fibers from Glutamate Toxicity To examine the efficacy of immunization with poly-Glu, Tyr without adjuvant to protect the neurons from glutamate toxicity, the retina of C57BL/6J mice were exposed to excess amount of glutamate. The mice were divided into 3 experimental groups: (i) not immunized—negative control (n=9); (ii) immunized with poly-Glu,Tyr 25 μg/mouse (n=10); and (iii) immunized with poly-Glu,Tyr 225 μg/mouse (n=10). The treated groups were immunized with poly-Glu,Tyr dissolved in 100 μl PBS 7 days prior to intraocular glutamate injection. The number of RGCs that survived 7 days after exposure to elevated level of glutamate was counted and calculated as percentage of normal eyes. The results are shown in FIG. 2. RGC survival in the treated groups was significantly (t-test, p<0.001) higher than the negative control group. Upon exposure to glutamate, only 34% of the RGCs survived in the non-treated animals while 68% RGC survival was observed in the group treated with 25 μg poly-Glu,Tyr (t-test, p<0.005).

Section II

Immunization with Poly-Glu,Tyr Confers Neuroprotection in the Cns in the Spinal Cord and Optic Nerve Crush Injury Models Progression of damage is a common occurrence after any CNS insult. Consequently, the outcome of spinal cord injury is far more severe than might be expected from the immediate effect of the insult. This is because the injury not only involves primary degeneration of the directly injured neurons, but also initiates a self-destructive process that leads to secondary degeneration of neighboring neurons that escaped the initial insult. Much research has been devoted to limiting the extent of secondary degeneration and thereby improving functional recovery from partial CNS injury (Hauben et al., 2000a, 2000b; Basso et al., 1996).

Studies over the last few years in the inventor's laboratories have provided evidence that the immune system, if properly harnessed, can play a pivotal role in regrowth of the injured spinal cord and its protection from secondary degeneration (Hauben et al., 2000a, 2000b, 2001). It was of interest to examine the effect of poly-Glu,Tyr immunization in spinal cord injury.

Acute incomplete spinal cord injury at the low thoracic levels causes an immediate loss of hind limb motor activity that spontaneously recovers within the first 12 days post-injury and stabilizes on deficient movement abilities. The amount of motor function restoration is the sum up effect of the positive recovery from spinal shock and the negative effect of longitudinal and ventral spread of damage. A therapeutic approach aiming at reducing the spread of damage through neuroprotection will result in a better recovery in terms of hind limb motor activity.

In the following experiments, the effect of active immunization with poly-Glu,Tyr on motor activity of the hind limb after spinal cord contusion, was tested.

Materials and Methods—Section II

Animals. Adult male SPD rats (aged 8-12 weeks) were housed in light- and temperature-controlled rooms. The rats were matched for age and size in each experiment. Prior to their use in experiments, animals were anesthetized by intraperitoneal administration of ketamine (80 mg/kg) and xylazine (16 mg/kg).

Antigens. MBP was from spinal cords of guinea pigs. Ovalbumin (Ova) and Con-A were purchased from Sigma (St. Louis, Mo., USA). Cop 1 was purchased from Teva Pharmaceuticals Ltd. (Petach Tikva, Israel). The MBP p87-99 peptide was synthesized at the Weizmann Institute of Science (Rehovot, Israel).

Spinal cord contusion. SPD rats were anesthetized and their spinal cords were exposed by laminectomy at the level of T7, T8 or T9. One hour after induction of anesthesia, a 10-g rod was dropped onto the laminectomized cord from a height of 50 mm, using the New York University (NYU) impactor, a device shown to inflict a well-calibrated contusive injury of the spinal cord (Basso et al., 1996; Hauben et al., 2000a).

Immunization. Rats were immunized with 100 or 500 μg of poly-Glu,Tyr emulsified with an equal volume of CFA containing 0.5 mg/ml *Mycobacterium tuberculosis*. The emulsion (total volume 0.1 ml) was injected SC in the upper back in the rats. Control rats were injected with PBS in CFA (Difco Laboratories, Detroit, Mich., USA).

Assessment of recovery from spinal cord contusion. Behavioral recovery was scored in an open field using the Basso, Beattie, Bresnahan (BBB) locomotor rating scale (Basso et al., 1995), where a score of 0 registers complete paralysis and a score of 2, complete mobility. Blind scoring ensured that observers were not aware of the treatment received by individual rats. Aproximately twice a week, the locomotor activities of the trunk, tail and hind limbs were evaluated in an open field by placing each rat for 4 min in the center of a circular enclosure (90 cm diameter, 7 cm wall height) made of molded plastic with a smooth, non-slip floor. Before each evaluation, the rats were examined carefully for perineal infection, wounds in the hind limbs, and tail and foot autophagia.

Crush injury of optic nerve: (a) The optic nerve is subjected to crush injury. Briefly, rats are deeply anesthetized by intraperitoneal (i.p.) injection of Rompun (xylazine, 10 mg/kg; Vitamed, Israel) and Vetalar (ketamine, 50 mg/kg; Fort Dodge Laboratories, Fort Dodge, Iowa). Using a binocular operating microscope, lateral canthotomy is performed in the right eye, and the conjunctiva is incised lateral to the cornea. After separation of the retractor bulbi muscles, the optic nerve is exposed intraorbitally by blunt dissection. Using calibrated cross-action forceps, the optic nerve is subjected to a crush injury 1-2 mm from the eye. Mild and severe crush injuries are inflicted for short-term trials (two weeks), as this time period is shown to be optimal for demonstrating secondary degeneration and its response to treatment (Yoles and Schwartz, 1998). The uninjured contralateral nerve is left undisturbed; (b) Rats are anesthetized and subjected to graded crush injury in the intraorbital portion of the optic nerve, 1-2 mm from the eyeball. With the aid of a binocular operating microscope, the conjunctiva is incised and the optic nerve exposed. Using cross-action calibrated forceps and taking special care not to interfere with the blood supply, the nerve is crushed for 30 s.

Measurement of secondary degeneration in the rat following optic nerve crush, by retrograde labeling of RGCs. Secondary degeneration of the optic nerve axons and their attached RGCs is measured by post-injury application of the fluorescent lipophilic dye, 4-[4-(didecylamino)styryl]-N-methylpyridinium iodide (4-Di-10-Asp) (Molecular Probes Europe BV, Netherlands), distally to the lesion site, two weeks after crush injury. Because only axons that are intact can transport the dye back to their cell bodies, application of the dye distally to the lesion site after two weeks ensures that only axons that survived both the primary damage and the secondary degeneration will be counted. This approach enables differentiation between neurons that are still functionally intact and neurons in which the axons are injured but the cell bodies are still viable, because only those neurons whose fibers are morphologically intact can take up dye applied distally to the site of injury and transport it to their cell bodies. Using this method, the number of labeled RGCs reliably reflects the number of still-functioning neurons. Labeling is carried out as follows: the right optic nerve is exposed for the second time, again without damaging the retinal blood supply. Complete axotomy is performed 1-2 mm from the distal border of the injury site and solid crystals (0.2-0.4 mm diameter) of 4-Di-10-Asp are deposited at the site of the newly formed axotomy. Five days after dye application, the rats are killed, their retinas are detached from the eyes, prepared as a flattened whole mount in 4% paraformaldehyde solution, and examined for labeled RGCs by fluorescence microscopy.

Assessment of RGC survival in rats. Survival of RGCs in rats is measured after post-injury application of 4-Di-10-Asp, distally to the optic nerve head as described above. Labeling and measurement are carried out as follows: the optic nerve is exposed without damaging the retinal blood supply. Complete axotomy is performed 1-2 mm from the optic nerve head and solid crystals (0.2-0.4 mm diameter) of 4-Di-10-Asp are deposited at the site of the formed axotomy. Five days after dye application, the rats are killed, their retinas are detached from the eyes, prepared as a flattened whole mount in 4% paraformaldehyde solution, and examined for labeled RGCs by fluorescence microscopy.

Example 3

Activation of Splenocytes from Contused Animals

Figure 3:
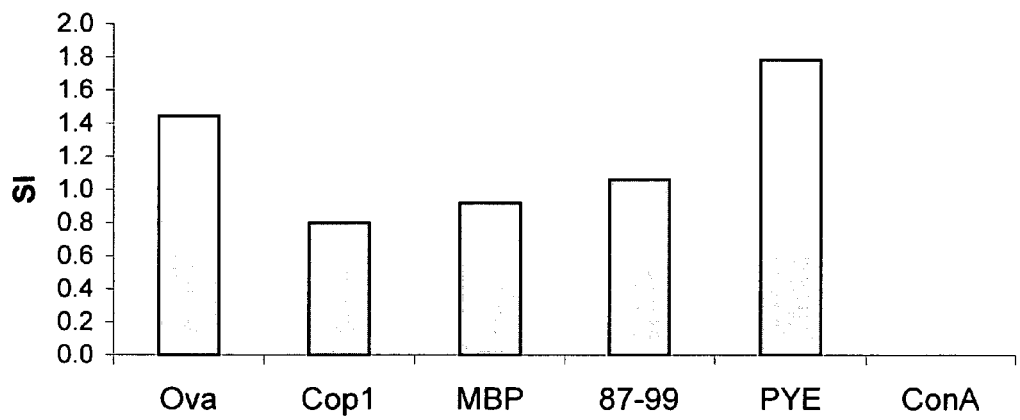
FIG. 3 is a graph showing the results of proliferation assay of splenocytes in response to different antigens: ovalbumin (Ova), copolymer 1(Cop 1), myelin basic protein (MBP), the MBP peptide p87-99, poly-Glu,Tyr (polyYE) and concanavalin A (Con A). The assay was carried out in splenocytes isolated from SPD rats 8-10 days after the rats were subjected to spinal cord contusion. The index was determined in comparison to proliferation of splenocytes in medium not containing any antigen (SI1).

SPD rats were anesthetized and their spinal cords were exposed by laminectomy at the level of T8. One hour after induction of anesthesia, a 10-g rod was dropped onto the laminectomized cord from a height of 50 mm, using the NYU impactor (Basso et al., 1995 and 1996). Rats were killed 8-10 days after spinal cord contusion and their spleens were excised and pressed trough a fine wire mesh. The washed cells ($2 \times 10^6$/ml) were cultured in triplicate in flat-bottomed microtiter wells in 0.2 ml proliferation medium containing DMEM supplemented with L-glutamine (2 mM), 2-mercaptoethanol ($5 \times 10^{-5}$ M), sodium pyruvate (1 mM), penicillin (100 IU/ml), streptomycin (100 µg/ml), non-essential amino acids, and autologous rat serum 1% (vol/vol) with the antigen (15 µg/ml) or Con A (1.25 µg/ml), and irradiated thymocytes (2000 rad, $2 \times 10^6$ cells/ml). The proliferative response to different antigens namely Ova, Cop 1, MBP, the MBP peptide 87-99, poly-Glu,Tyr and Con A, was determined by measuring the incorporation of [$^3$H]thymidine (1 µCi/well), which was added for the last 16 h of a 72 h culture. The splenocyte proliferation index (SI) was determined as compared to the proliferation of the splenocytes in medium with no antigen (SI=1 indicates no proliferation response to the antigen above the proliferation without any antigen). This parameter is indicative of the physiological T-cell repertoire in contused animals. Con-A is the positive control. The results in FIG. 3 show that the proliferative response of splenocytes of the spinally contused rats to poly-Glu,Tyr (pYE) was higher than to the other antigens.

Example 4

Active Immunization with Poly-Glu,Tyr: the Effect of Pye/Cfa Immunization on Rat Recovery from Spinal Cord Contusion A contusive injury of the spinal cord was inflicted on anesthetized 12 SPD male rats by using the NYU impactor device to drop a 10-g rod from a height of 50 mm onto the exposed laminectomized spinal cord at level T8. The NYU impactor device used allowed, for each animal, measurement of the trajectory of the rod and its contact with the exposed spinal cord to allow uniform lesion. The resultant injury involves mostly the white matter and is analogous to accidental spinal cord injury in humans. Due to the spinal shock, the motor skills of the rats' hind limbs initially disappeared, but recovered with time to reach a steady state of deficient motor activity. The amount of this deficiency caused by the injury can be reduced with adequate neuroprotective treatment.

Figure 4A:
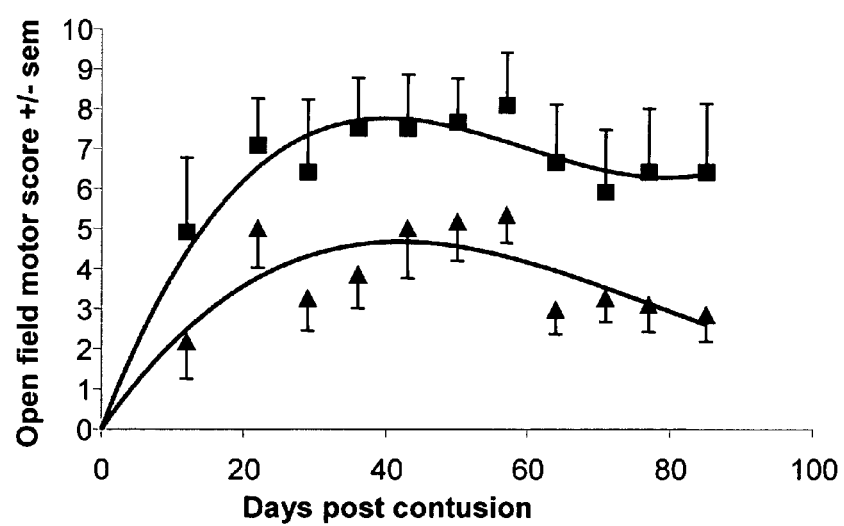
FIGS. 4A-4B depict the effects of pYE/CFA immunization on the recovery of rats from spinal cord contusion. The graphs presents the mean ±sd of hindlimbs motor activity scores in open field (BBB test) with time after spinal cord injury in two groups of SPD rats immunized with pYE/CFA (squares) or CFA-PBS (control; triangles) immediately after spinal cord injury (FIG. 4A).

The rats were divided into 2 groups (6 each) according to their impact errors to achieve similar groups. In one group, the rats were SC immunized in their upper back with PBS/CFA. In the other group, the rats were SC immunized with poly-Glu,Tyr/CFA (100 µg/rat). Both groups were immunized immediately after the injury and 7 days later both groups received a second immunization identical to the first one. The hind limb motor skills of the animals were scored using the BBB locomotor rating scale, following the kinetics and amount of hind limb motor activity in the two experimental groups. The results depicted in FIG. 4A show that rats treated with poly-Glu,Tyr (squares) showed a tendency to recover better than PBS-treated rats (triangles).

Figure 4B:
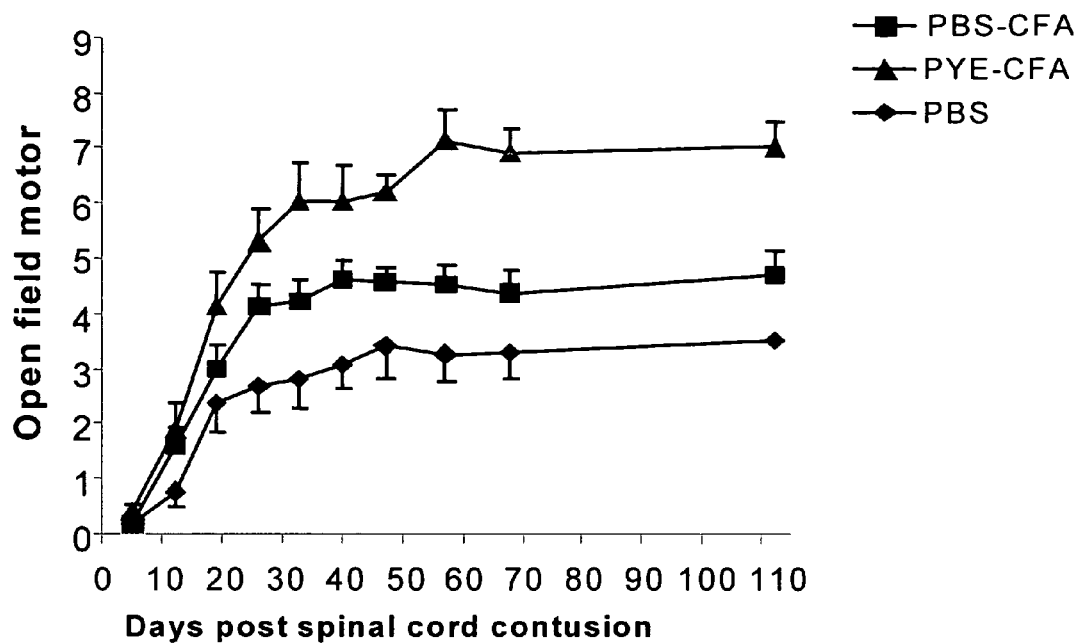

In another experiment, rats were subjected to controlled severe contusion of the exposed spinal cord at level T9 using the NYU impactor; the impact rod (10 g) was dropped from a height of 50 mm. The contused rats were randomly divided into a poly-Glu,Tyr treatment group (6 rats) and a control group. Rats in the treatment group were immunized with 500 µg poly-Glu,Tyr emulsified in CFA, injected SC into the base of the tail. Control rats were injected with PBS emulsified in CFA (6 rats), or with PBS alone (5 rats). The immunization was given up to 1 hour after contusion. The animals were evaluated neurologically over the weeks following contusion by assessing locomotor activity in an open field with the BBB locomotor rating scale. The results depicted in FIG. 4B show that rats immunized with poly-Glu,Tyr (triangles) recovered significantly better than the control PBS/CFA (squares) and PBS-treated (diamonds) rats.

Example 5

Immunization with Splenocytes Activated with Poly-Glu,Tyr

SPD rats (n=4) were SC immunized in their lower back with pYE/CFA (125 µg/rat). Seven days later their splenocytes were harvested and a single cell suspension was prepared by pressing the spleens against a metal mesh using the plunger of a syringe. The splenocytes were activated in culture for 3 days with pYE (10 µg/ml). The cells were harvested, washed in PBS and counted.

Figure 5:
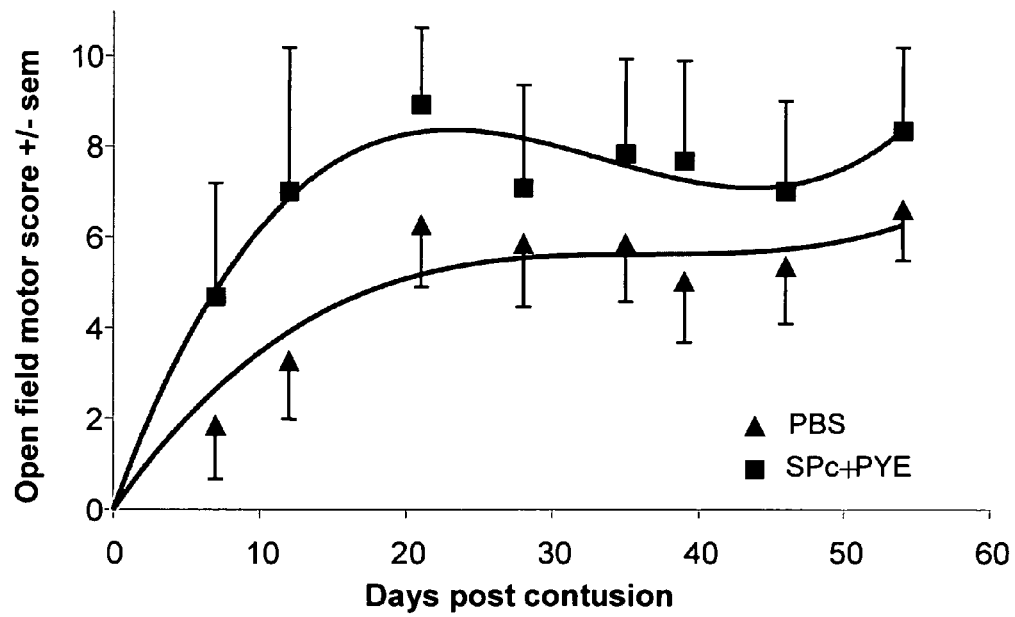
FIG. 5 depicts the effects of adoptive transfer of splenocytes activated with poly-Glu,Tyr on spinal cord injury recovery. The graph presents the mean ±sd of hindlimbs motor activity scores in open field (in each group) with time after spinal cord injury in two groups of SPD rats injected intraperitoneally with CFA-YE-activated T cells (SPc+pYE; squares) or CFA-PBS-treated T cells (control; triangles) immediately after spinal cord injury.

Another group of 12 male SPD rats went trough surgery and their spinal cord was contused at T7 level using the NYU impactor. Immediately after the contusion, the rats were divided into 2 equal groups according to their impact errors. One group received intravenously 0.5 ml of PBS and the other group received splenocytes activated with pYE ($30 \times 10^6$/0.5 ml PBS/rat). The rats were followed for their recovery of function using the open field BBB score. The results depicted in FIG. 5 show that the rats treated with splenocytes activated with pYE (squares) recovered better than the control group (triangles).

Section III

Poly-Glu,Tyr Immunization Confers Neuroprotection in the Chronic and Acute Glaucoma Models Glaucoma is now recognized as a chronic neurodegenerative disease, characterized by the slow, progressive degeneration of RGCs, causing a gradual loss of visual field and leading eventually to blindness. The primary cause of the disease is not yet known and the factors contributing to its progression are not yet fully characterized. Blockage of aqueous outflow causes an increase in intraocular pressure (IOP), which results in RGC death (Bakalash et al., 2002; Schori et al., 2001b). Increased IOP is considered the major risk factor and believed to be the primary cause of neuronal death. Accordingly, biochemical agents or surgery designed to reduce IOP are the current standard therapy. Though IOP reduction significantly reduces the extent of neuronal loss, loss of RGCs may continue even after the IOP has been reduced. Moreover, optic nerve degeneration sometimes occurs in the absence of elevated IOP, a condition called normal tension glaucoma (occurring in approximately one third of glaucoma patients). The present inventors have attributed the ongoing loss of neurons to secondary factors that continue to cause degeneration of neurons (RGCs and their fibers) after the primary insult (e.g. increased IOP) is removed. Thus, neuroprotective therapy may be considered appropriate for treatment of glaucoma.

Deleterious factors (e.g. abnormally high concentrations of glutamate and nitric oxide) that might be associated with secondary degeneration were demonstrated in patients with glaucoma as well as in monkeys with abnormally high IOP. Similar changes are observed in a rat model of partial optic nerve injury, often used for studies of secondary degeneration. Since no single model fully simulates glaucoma, it is proposed that demonstrating neuroprotection in several in vivo models of retinal or optic nerve injury will provide comprehensive pre-clinical data that will eventually lead to clinical trials. Besides the mouse model of intraocular glutamate toxicity described in Section I above, the neuroprotetive effect of poly-Glu,Tyr either administered SC with adjuvant or in eye drops without adjuvant, is here examined in rat models of irreversible (chronic) or transient (acute) elevation of IOP.

Materials and Methods—Section III

Animals. Inbred adult male Lewis and SPD rats (8 weeks; average weight 300 g) were maintained in a light- and temperature-controlled room and were matched for age and weight before each experiment.

Chronic glaucoma: Induction of high IOP. Male Lewis rats were anesthetized with a mixture of ketamine (15 mg/kg), acepromazine (1.5 mg/kg), and xylazine (0.3 mg/kg). An increase in IOP was achieved by laser photocoagulation of the limbal and episcleral veins. Rats received 2 laser treatments, 1 week apart, with a blue-green argon laser (1 watt for 0.2 s, delivering a total of 130-150 spots of 50 or 100 µm in the 2 treatments; Coherent, Palo Alto, Calif.). IOP was measured once a week using TONO-PEN (Mentor, Norwell, Mass.), after injecting the rats intramuscularly with acepromazine (3.0 mg/kg) and applying procaine 0.5% topically on the eyes to anesthetize the cornea.

Acute glaucoma: Induction of high IOP. In our rat model of acute glaucoma, the IOP was transiently elevated for one our using Ringer fluid reservoir connected via a 27-gauge needle to the anterior chamber of the deeply anesthetized rats (ketamine hydrochloride 50 mg/kg, xylazine hydrochloride 0.5 mg/kg, injected intramuscularly). The reservoir height was adjusted to give a pressure of 50 mmHg. This was maintained for one hour during which IOP measurements were taken using a tonopen (Tonopen XL). Twenty-four hours after removal of the needle from the anterior chamber, normal IOP values (lower than 20 mmHg) were measured.

Measurement of IOP. Most anesthetic agents cause a reduction in IOP, thus precluding reliable measurement. To obtain accurate pressure measurements while the rat was in a tranquil state, we injected the rat intraperitoneally (i.p.) with 10 mg/ml acepromazine, a sedative drug that does not reduce 1OP. Five minutes later, Localin was applied to the corneas of both eyes and the pressure in both eyes was measured using a Tono-Pen XL tonometer (Automated Ophthalmics, Ellicott City, Md., USA). Ten measurements were taken from each eye and the averages were calculated. Because of the reported effect of anesthetic drugs on IOP measured by Tono-Pen (Jia et al., 2000), we always measured at the same time after acepromazine injection and calculated the average of the 10 values received from each eye. Measurements were performed every 2 days for 3 weeks, all at the same time of day. One week after the first laser treatment, the IOP reached levels of about 30 mmHg without any significant change until the end of the experiment (3 weeks after the first laser treatment). IOP in the untreated contralateral eye remained normal. Table 1 (below) summarizes the RGCs survival in rats with normal IOP and in rats with a laser-induced increase in IOP three weeks later.

Anatomical assessment of retinal damage caused by the increase in IOP: RGC survival. The hydrophilic neurotracer dye dextran tetramethylrhodamine (Rhodamine Dextran) (Molecular Probes, Oregon, USA) was applied 3 weeks after the first laser treatment directly into the intraorbital portion of the optic nerve. Only axons that survive the high IOP and remain functional, and whose cell bodies are still alive, can take up the dye and demonstrate labeled RGCs. The rats were killed 24 hours after dye application and their retinas were excised, whole mounted, and preserved in 4% paraformaldehyde. The labeled RGCs were counted under magnification of ×800 in a Zeiss fluorescence microscope. Four fields from each retina were counted, all with the same diameter (0.076 mm$^2$) and located at the same distance from the optic disc. Eyes from untreated rats were used as a control. RGCs were counted by an observer blinded to the identity of the retinas.

Active immunization with adjuvant. SPD rats were immunized SC with poly-Glu,Tyr (500 μg) emulsified with an equal volume of CFA containing 0.5 mg/ml *Mycobacterium tuberculosis* (total volume 0.1 ml). Control rats were injected with an emulsion of PBS in CFA (Difco Laboratories, Detroit, Mich., USA).

Active immunization without adjuvant Poly-Glu,Tyr was administered topically as eye drops after immersing the substance in PBS at a concentration of 10 mg/ml. Since each drop was of 50 μl, we administered 1 drop every 5 minutes for a total of 10 drops in 50 minutes.

TABLE 1

Elevated IOP causes severe RGC loss

|  | n | Mean RGC ± SD (per mm$^2$) | % Survival |
|---|---|---|---|
| Normal | 5 | 2525 ± 372 | 100% |
| 3 weeks post laser (IOP mean ± SD = 29.9 ± 2.38 mmHg) | 10 | 1420 ± 272 | 53.9% |

Example 6

Figure 6:
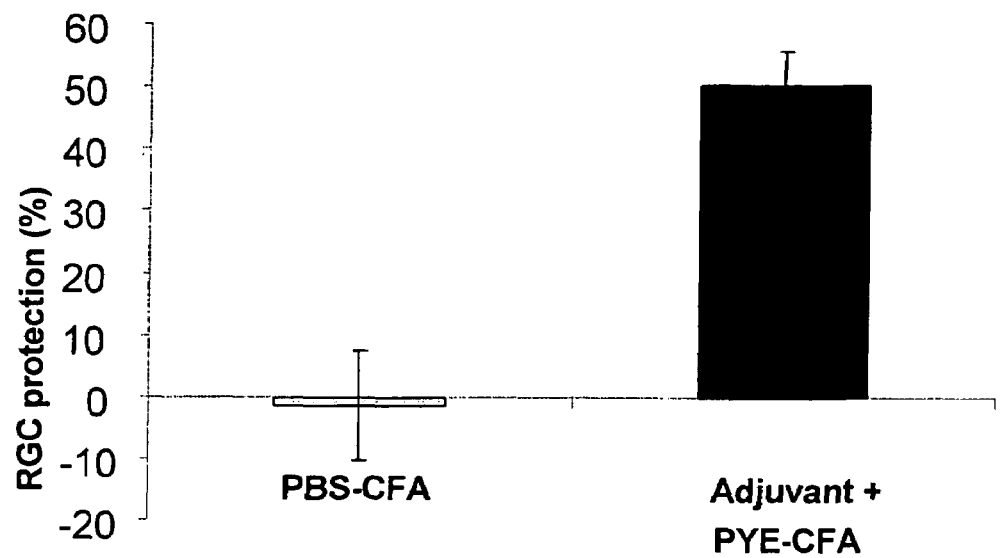
FIG. 6 shows that immunization of rats with poly-Glu,Tyr with adjuvant (PYE-CFA) increased RGC survival in the glaucoma intraocular pressure (IOP) model, in comparison to non-immunized rats (PBS-CFA).

Effect of Poly-Glu,Tyr Immunization with Adjuvant on RGC Survival in the Chronic Glaucoma IOP Model SPD rats were immunized with poly-Glu,Tyr (500 μg) emulsified with CFA one hour after the first laser treatment (n=9). One control group was immunized with PBS/CFA (n=7) and a second control group was injected with PBS alone (n=5). As shown in FIG. 6, though the IOP remained elevated throughout the experimental period, rats immunized with poly-Glu,Tyr in CFA, but not with PBS-CFA, showed significant increase in the number of surviving RGCs compared to non-immunized rats (PBS alone). Protection of RGC was calculated as percentage of cells survived in the treated groups out of the total cell loss in the non-immunized group.

Example 7

Effect of Poly-Glu,Tyr Immunization on RGC Survival in the Acute Glaucoma IOP Model One in one hundred individuals have narrowing of the opening through which intraocular fluid flows out of the eye. When this area suddenly closes off, it results in a build up of fluid pressure known as acute glaucoma. This damages the optic nerve causing partial vision loss, with blindness as possible, eventual outcome.

Figure 7:
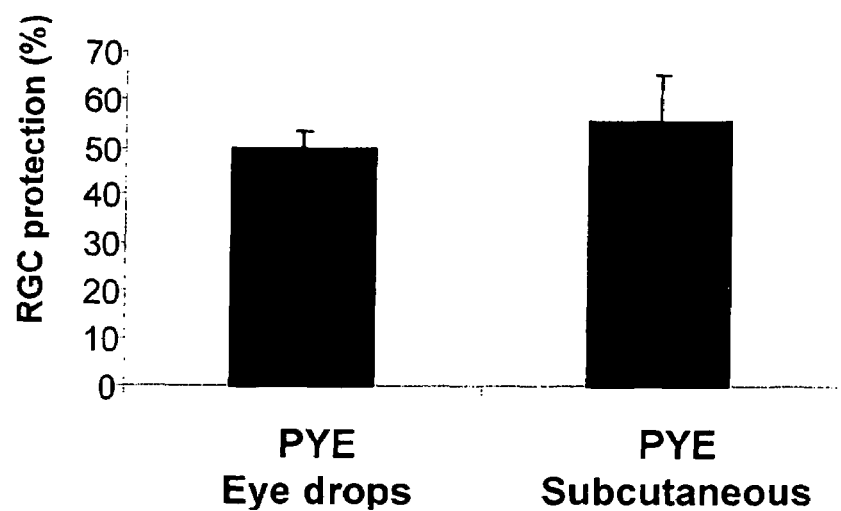
FIG. 7 shows protection of RGCs of rats immunized with poly-Glu,Tyr either subcutaneously or with eye drops in the acute glaucoma IOP model.

Rats with transient IOP elevation (acute glaucoma model) were treated with poly-Glu,Tyr immediately after removal of the needle. Poly-Glu,Tyr was administered either by subcutaneous injection (500 μg) or in five eye drops (1 mg each) given at 5 minute intervals. Both treatments significantly reduced RGC loss induced by transient IOP elevation, as depicted in FIG. 7. Control animals were treated with PBS instead of poly-Glu,Tyr solution. RGC protection was calculated as percentage cell survival in the treated groups relative to the total cell loss in the corresponding non-treated groups.

Example 8

Figure 8:
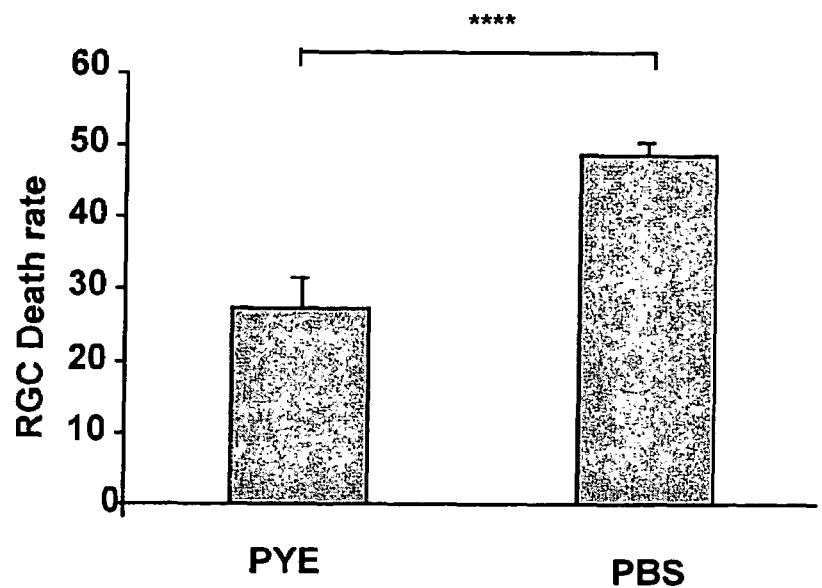
FIG. 8 shows that immunization with eye drops containing poly-Glu,Tyr induces neuroprotection to RGCs in a model of chronic glaucoma.

Administration of Poly-Glu,Tyr in Eye Drops without Adjuvant Induces Neuroprotection to Rgcs in a Model of Chronic Glaucoma Induction of high IOP was done using Argon laser irradiation that blocks the outflow of aqueous humor out of the eye. Immediately after the second laser session (seven days after the first laser irradiation), poly-Glu,Tyr was immersed in an isotonic solution (PBS) in a concentration of 10 mg/ml and applied on the eye. Assuming that about 10% of the total amount would penetrate the blood vessels and that each drop was of 50 μl volume, a total of 10 drops were administered during a course of 50 minutes. Each drop remained on the cornea for 5 minutes, allowing the substance to penetrate into the conjunctival circulation so that at least 500 μg penetrate into the blood vessels that drain from the eye. Control eyes were applied with PBS in the same manner. Death rates of RGCs (mean ±SD) after exposure to elevated IOP were calculated as percentage of normal eyes (controls). The results are shown in FIG. 8. The average death rate 3 weeks after IOP elevation was 48.52%±1.68 in the control (n=4) and 27.33%±4.73 in the group treated with poly-Glu,Tyr (n=6), (p<0.0001).

Example 9

Figure 9:
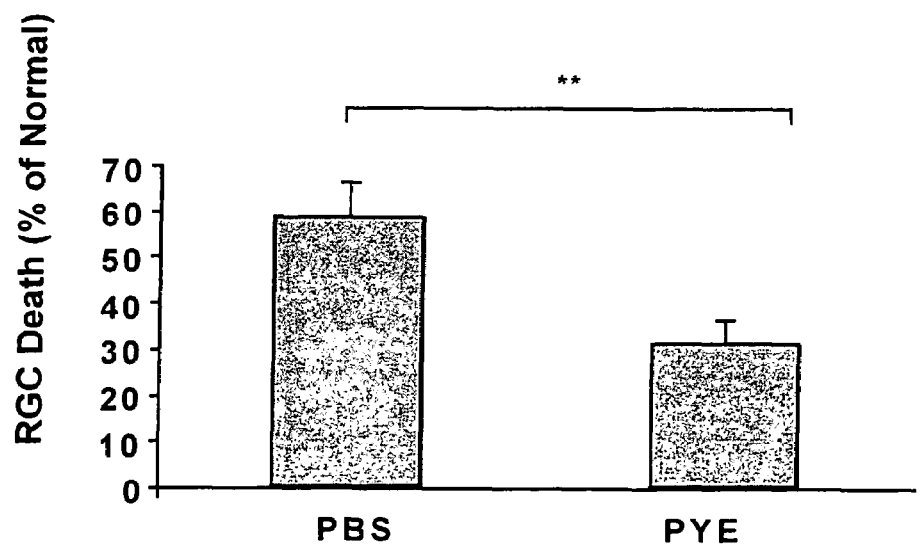
FIG. 9 shows that immunization with eye drops containing poly-Glu,Tyr induces neuroprotection to RGCs in a model of acute glaucoma.

Administration of Poly-Glu,Tyr in Eye Drops without Adjuvant Induces Neuroprotection to Rgcs in a Model of Acute Glaucoma High unilateral IOP was induced by inserting 30-gauge needle connected to a polyethylene tube and normal saline (0.9%) infusion. The infusion bag was placed 1 meter above the rat's head. The rats were deeply anesthetized with ketamine and xylazine. High IOP was induced for exactly 1 hour, ten IOP measurements were taken with Tono-Pen (XL, Mentor®, Norwell, Mass.). The IOP generated damage was assessed two weeks later by counting the surviving RGCs dyed retrogradely with Rhodamine Dextran. Poly-Glu,Tyr or PBS (control) were applied on the eye in the same manner that is described in Example 8. The results are shown in FIG. 9. Death rates were 58.58%±7.42 in the control group (n=4) and 31.5±4.73 in the group treated with poly-Glu,Tyr (n=6), (p<0.01).

Example 10

Immunization with Poly-Glu,Tyr has a Systemic Effect

Figure 10:
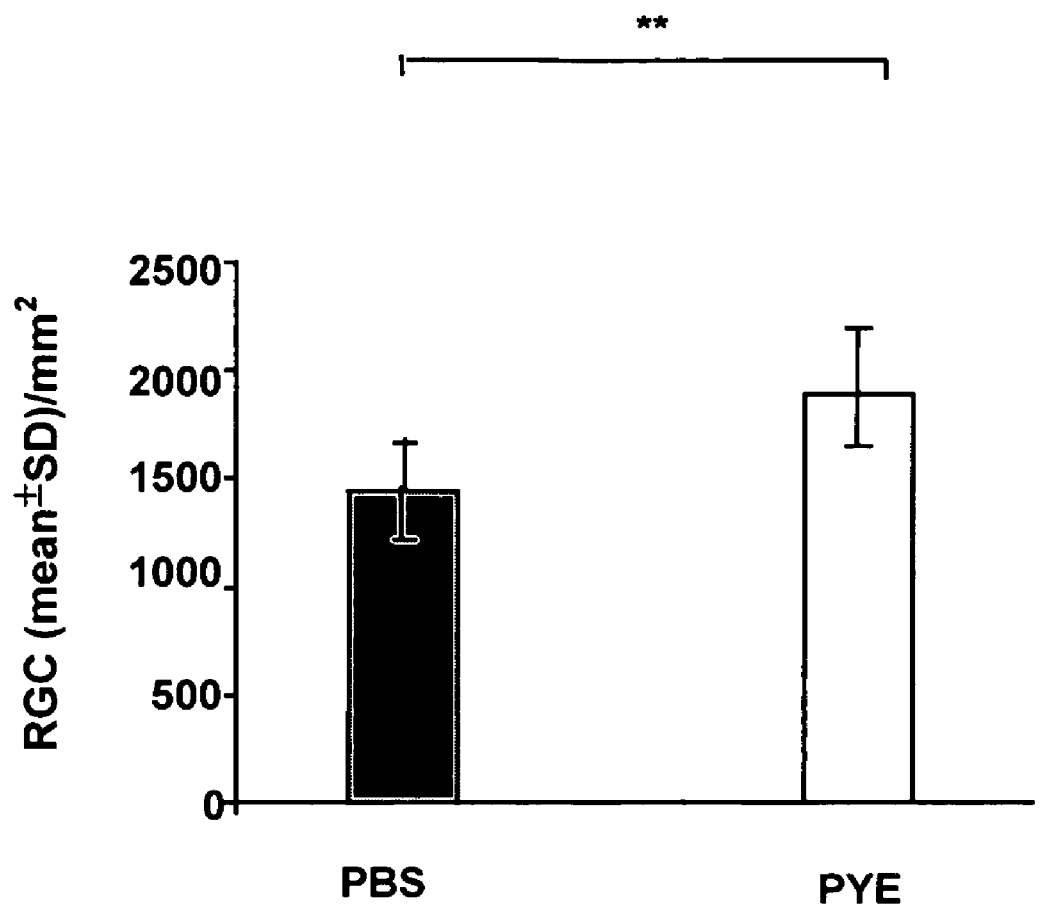
FIG. 10 shows that immunization with eye drops containing poly-Glu,Tyr has a systemic effect—acute rise of IOP was inflicted in the right eye of the rats and the contralateral side (left eye) was treated with poly-Glu,Tyr. The effect was the same as when poly-Glu,Tyr was applied ipsilaterally.

In this experiment, in order to prove that the eye drops provide a route of immunization, and not a way of local drug application, we inflicted acute rise in IOP in the right eye of Lewis rats and applied poly-Glu,Tyr in eye drops to the contralateral side. Thus, eye drops of PBS or poly-Glu,Tyr were applied on the left eye and viable RGCs were labeled and counted two weeks later in the right eye. The results are shown in FIG. 10. RGC cell count per mm$^2$ was 1454±221 in the control group (n=6) and 1908±252 per mm$^2$ in the group treated with poly-Glu,Tyr (n=5). It can be seen that the difference between the group treated with poly-Glu,Tyr, on one hand, and the control group (left column), on the other hand, was significant (p<0.01).

These results show that same effect was obtained as when given ipsilaterally, namely, poly-Glu,Tyr induced neuroprotection in the non-treated eye.

Section IV Immunization with Poly-Glu,Tyr Circumvents Tissue Specificity Barrier The inventor M. Schwartz and her team have shown previously that a tissue-specific self-antigen that is associated with an autoimmune disease in an organ, or a fragment of said self-antigen, can confer protective immunity to a non-autoimmune injury, disease, or disorder of said organ. For example, in the case of the T-cell-mediated eye-specific autoimmune disease uveitis, it was assumed that the interphotoreceptor retinoid-binding protein (IRBP), an uveitogenic antigen residing in the eye or a fragment thereof, could be used to protect the eye from a non-autoimmune disease, disorder or injury in the eye. Thus, it was shown that the Peptide R16, which sequence corresponds to the amino acid sequence 1177-1191 of bovine IRBP, conferred significant protection to the eye against glutamate toxicity and from the consequences of optic nerve injury (Mizrahi et al., 2002; WO 03/079968).

Another example of tissue specificity refers to the protection provided to the CNS by myelin-associated antigens in cases of CNS injury. The inventors have previously shown that passive or active immunization with T cells specific for CNS-associated myelin antigens reduces secondary degeneration in a rat model of spinal cord contusion. It was found that the protection and repair following spinal cord injury is amenable to therapeutic vaccination with myelin-associated antigens such as MBP and MBP-derived peptide (Moalem et al., 1999; WO 99/60021), the altered MBP-derived peptide A91 (derived from the encephalitogenic MBP peptide 87-99 in which the Lys residue 91 was replaced with Ala) (Hauben et al., 2001a; WO 02/055010), or even a Nogo peptide (Hauben et al., 2001b; WO 03/002602), but not with antigens specific for the eye (Mizrahi et al., 2002; WO 03/079968).

Poly-Glu,Tyr, as exemplified in Sections I-III hereinabove, protects the eye from glutamate toxicity and high IOP and confers neuroprotection in an animal model of spinal cord injury. It was, thus, of interest to compare the effect of poly-Glu,Tyr in these models with the eye tissue-specific antigen peptide R16 and the CNS-specific antigen peptide A91.

Materials and Methods—Section IV

Animals. Inbred adult 8-12-week old male Lewis (for the glaucoma model) or SPD rats (for the spinal cord model) were housed in a light- and temperature-controlled room and were matched for age and weight in each species for each experiment.

Antigens. The peptides A91 and R16 were synthesized by the Synthesis Unit at the Weizmann Institute of Science (Rehovot, Israel).

Active immunization Rats were immunized with peptide R16 (30 μg), peptide A91 (100 μg), or with poly-Glu,Tyr (100 μg), each antigen emulsified with 0.05 ml CFA containing 0.5 mg/ml *Mycobacterium tuberculosis* (Difco Laboratories, Detroit, Mich., USA) and 0.05 ml PBS (total volume 0.1 ml). The emulsion was injected SC into each rat at the base of the tail. Control rats were injected with PBS in CFA. In the chronic glaucoma model (see Section III above), male Lewis rats with a laser-induced increase in IOP were immunized, immediately after the first laser session, and in the incomplete spinal cord injury (ISCI) model (see Section II above), SPD rats were immunized within one hour after contusion at the level of T8.

Example 11

Poly-Glu,Tyr Circumvents the Tissue Specific Barrier

The experiments were carried out as described in Sections II-III hereinabove.

Figure 11:
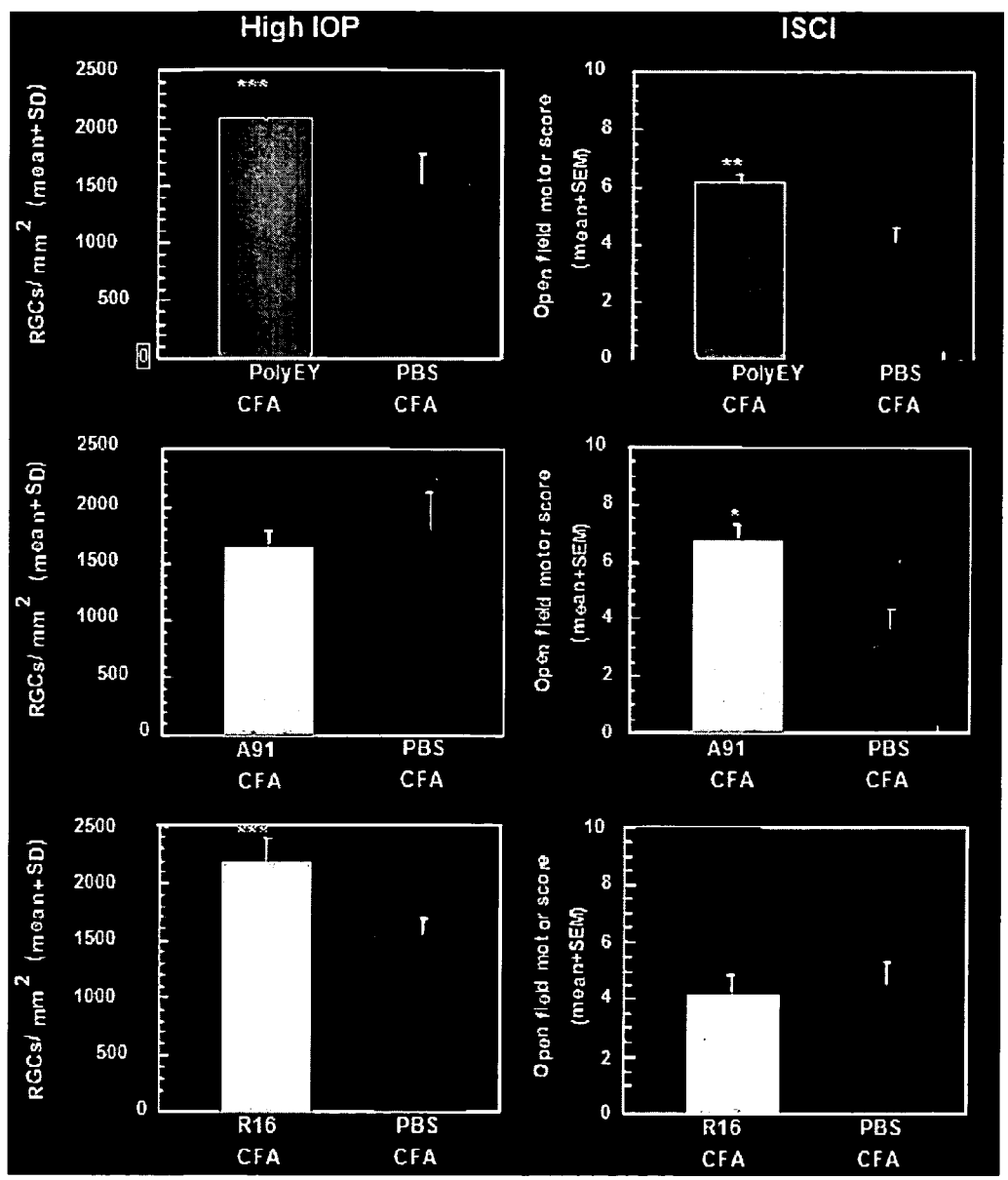
FIG. 11 shows the effect of immunization with uveitogenic peptide R16, altered MBP-derived peptide A91, and poly-Glu,Tyr on RGC survival in the rat glaucoma IOP and spinal cord injury models. Poly-Glu,Tyr circumvented the tissue-specificity barrier and was active in both models.

FIG. 11 shows results of immunization with the tissue-specific antigens R16 and A91 and poly-Glu,Tyr in reducing neuronal death following injury to gray matter (elevated IOP) or white matter (spinal cord injury).

Exposure of the retina to high IOP causes death of the RGCs. The left panels of FIG. 11 show that immunization with the retina specific antigen peptide R16 significantly reduced RGC death, while immunization with the myelin specific antigen peptide A91 had no effect on RGC survival. Poly-Glu,Tyr also significantly reduced RGC death showing that immunization with poly-Glu,Tyr conferred neuroprotection in the glaucoma model.

The same effect was obtained in the model of incomplete spinal cord injury (ISCI), which is mainly damage to myelinated axons. The right panels of FIG. 11 show that immunization with the myelin specific antigen peptide A91 significantly improved functional outcome of the spinally contused rats as measured by the open-field motor score using the BBB scale while immunization with the retina specific antigen peptide R16 had no effect. Poly-Glu,Tyr also significantly improved functional outcome of the contused rats showing that immunization with poly-Glu,Tyr afforded neuroprotection in this model too.

In summary, these results show the tissue specific nature of neuroprotective immunization and that poly-Glu,Tyr circumvents the tissue-specificity barrier.

Section V

Neuroprotective Effect of Poly-Glu,Tyr in Stroke

Stroke (cerebrovascular accident) is a sudden neurological deficit. Strokes are caused either by occlusion of cerebral blood vessels, e.g., the middle cerebral artery (MCA), leading to ischemic necrosis of the brain (cerebral infarction) or by rupture of blood vessels resulting in hemorrhage in the brain (hemorrhagic or bleeding stroke). Eighty percent of strokes are occlusive and 20 percent are hemorrhagic.

The interruption of blood flow deprives the brain of blood and oxygen and causes the death of brain cells. Impaired blood supply causes immediate loss of neurons at the ischemic site followed by secondary neuronal loss that affects the part of the body it controls. If the stroke is not resolved within a short period of time, the injury will lead to devastating losses in sensory, motor, and cognitive functions, causing paralysis, language and vision and other problems.

For many years, there was no hope for those suffering a stroke. Recently, new treatments to remove obstruction and restore blood flow to the brain are used. Because their mechanisms are different, the treatments for the types of stroke are different: ischemic stroke is treated by dissolving the intravascular occlusion by thrombolytic therapy, for example with the blood clot dissolver called alteplase, a tissue plasminogen activator commonly called TPA, which must be administered within a three-hour window from the onset of symptoms to work best. Generally, only 3-5% of those who suffer a stroke reach the hospital in time to be considered for this treatment. In hemorrhagic stroke, an obstruction is introduced to prevent rupture and bleeding of aneurysms and arteriovenous malformations.

Some brain damage that results from stroke may be secondary to the initial death of brain cells caused by the lack of blood flow to the brain tissue. This brain damage is a result of a toxic reaction to the primary damage. Neuroprotective agents have being proposed in order to prevent this secondary injury and protect the brain from the harmful cellular and metabolic consequences of ischemic injury. However, despite promising pre-clinical results, no neuroprotective therapy was found effective in reducing secondary neuronal loss in stroke patients.

The failure of many clinical trials using neuroprotective agents targeting a specific pathway of the ischaemic cascade emphasizes the need of a new strategy for neuroprotection. As described above, it has been shown by the inventors that activation of the autoimmune response is part of a physiological repair mechanism following CNS damage. Moreover, an appropriately controlled boost to the immune response was shown to enhance functional recovery in the injured CNS.

Poly-Glu,Tyr is a synthetic copolymer that modulates immune activity, thus boosting the spontaneous repair mechanism evoked by CNS injury. We show herein that treatment with poly-Glu,Tyr leads to better survival of neurons exposed to toxic amounts of glutamate, a major common element in neurodegenerative diseases.

To investigate the neuroprotective effect of poly-Glu,Tyr on stroke, the dose and time window were tested in a permanent middle cerebral artery occlusion (MCAO) model in rats. Single injection of poly-Glu,Tyr, administered immediately, 6 hours or 24 hours post MCAO, significantly improved neurological outcome measured in several time points up to 14 days post-occlusion. These results were in line with the reduced weight loss observed in the poly-Glu,Tyr-treated animals. Administration of poly-Glu,Tyr had no effect on infarct volume, but enhanced hippocampus neuron survival. The neuroprotective effect may involve a transient inhibition of T-regulatory (Treg) cells, as may be seen in the reduced suppressive activity on T-cell proliferation and changes in cytokine secretion profile of T-regulatory cells in the presence of poly-Glu,Tyr (see Section IX hereinafter). Immune modulation using poly-Glu,Tyr is suggested to overcome major obstacles in the treatment of ischemic stroke, because of the relatively long therapeutic time window and its long lasting beneficial effects on functional recovery.

Immunization with poly-Glu,Tyr was shown in the examples above to reduce neuronal loss following mechanical injury to white matter (spinal cord contusion), or gray matter (IOP elevation) and chemically-induced damage in gray matter (intraocular glutamate toxicity). The stroke model represents a different mechanism of damage, with both gray and white matter affected by the lack of oxygen supply. Permanent occlusion of the MCA causes focal gray and white matter damage in the ischemic zone. It is well known that progressive neuronal degeneration occurs at the edges of the ischemic area (penumbra), a consequence of environmental toxicity secondary to the primary neuronal loss.

Here we show that poly-Glu,Tyr is effective in reducing neurological loss following permanent MCA occlusion in rats, indicating that treatment of stroke may be carried out with poly-Glu,Tyr, either alone or complementary to anti-clot therapy, and can lead to better recovery.

Materials and Methods—Section V

Animals. Adult male SPD rats (aged 8-12 weeks) were housed in light- and temperature-controlled rooms. The rats were matched for age and size in each experiment.

Induction of permanent ischemia. Permanent focal ischemia (permanent MCA occlusion) was produced in rats by inserting a 4-0 nylon monofilament via the proximal external carotid artery into the internal carotid artery, and thence into the circle of Willis, effectively occluding the MCA.

Determination of neurological severity scores (NSS) was performed at different times after MCA occlusion. The NSS is the total sum of a number of ratings assigned to each of 11 parameters of posture and locomotion. The scale runs from 0 (normal rat) to 19 (fully incapacitated rat). Individual parameters are rated as follows: 1. Sedation (no—0, marked—1); 2. Piloerection (no—0, marked—1); 3. Position—tendency to lean on contralateral side (no—0, marked—2); 4. Contralateral circling—spontaneous (no—0, marked —3); 5. Contralateral circling when pulled by tail (no—0, marked—2); 6. Extension of contralateral forelimb towards floor when lifted by tail (Good—0, flexed limb—1, twisting of the body—1); 7. Motor activity with respect to control 9 for 15 min in an automated activity cage (0=76-100%, 1=51-75%, 2=26-50%, $3 \leq 25\%$); 8. Grasp rod with contralateral limb for 5-15 sec. When suspended by the armpit (good—0, poor—1); 9. Walk on 5-cm wide beam (good—0, poor—1); 10. Restoration of contralateral hind- and fore-limb to original position when intentionally displaced (good—0, poor—1(1 limb), 2 (2 limb)); 11. Grasping and balance on beam 2-cm wide (good—0, poor—1).

Example 12

Figure 12:
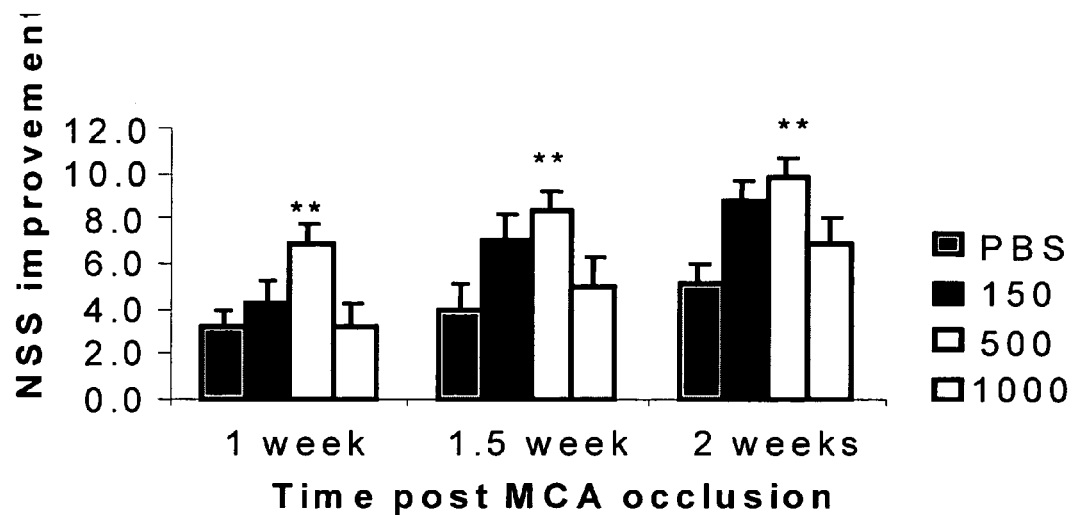
FIG. 12 shows dose response as expressed by improvement in neurological severity scores (NSS) in a rat model of stroke (MCA occlusion). Rats were subjected to permanent MCA occlusion and immediately thereafter treated with 150, 500 or 1000 μg poly-Glu,Tyr. The histogram shows score changes per animal averaged per group (n=15-19 animals per group), with the standard error of mean. (**$p<0.01$ repeated measures ANOVA).

Dose-Dependent Effect of Immunization with Poly-Glu,Tyr in a Rat Model of Stroke The experiment was performed using different doses of poly-Glu,Tyr (150, 500 and 1000 µg per rat). The control group was immunized with PBS. Immediately after permanent MCA occlusion was performed, rats were randomly divided into four groups: three groups were immunized with a single SC injection of poly-Glu,Tyr in PBS at different doses (150, 500 and 1000 µg per rat), and the control group was immunized with PBS. NSS were blindly determined 1-2 days, 7-8 days, 10-11 days and 14-15 days post-occlusion. The improvement in NSS, as measured on days 7-8 (1 week), 10-11 (1.5 weeks) and 14-15 (2 weeks) in comparison to the score on days 1-2, was calculated for each animal; the group averages and standard errors are shown in FIG. 12. All the rats immunized with poly-Glu,Tyr showed greater improvement in the neurological score than the control group. The rats that were immunized with 150 or 500 µg/rat showed the greatest improvement following 2 weeks. Analysis of variance (repeated measures) showed significant effect of the treatment on the NSS improvement (p=0.009).

Example 13

Figure 13:
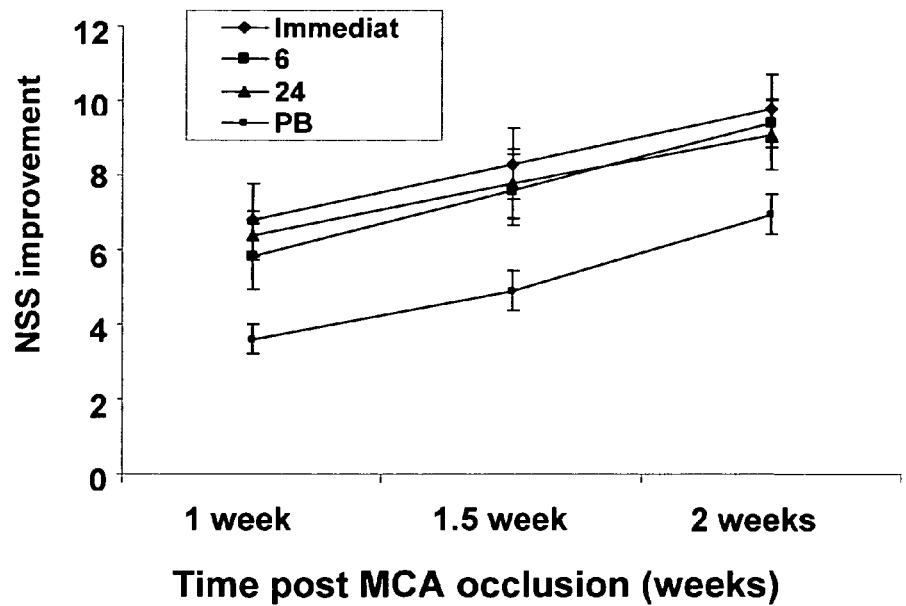
FIG. 13 shows that poly-Glu,Tyr significantly (ANOVA, $p<0.05$) improves the recovery neurological severity scores (NSS), when injected immediately, 6 and 24 hours post MCA occlusion compared to the control group immunized with PBS.

Therapeutic Window: Poly-Glu,Tyr Improves Neurological Severity Scores Following 6 and 24 Hours Post-Mca Occlusion in Rats In order to study the potential of a therapeutic time window after single injection of poly-Glu,Tyr, rats were immunized SC with 500 µg/rat poly-Glu,Tyr in PBS immediately (n=15), 6 hours (n=24) and 24 hours (n=15) post-MCA. The control group was injected with PBS (n=65). FIG. 13 shows the ability of poly-Glu,Tyr to reduce the neurological deficits of rats as measured up to 14 days (2 weeks) post-occlusion.

Figure 14:
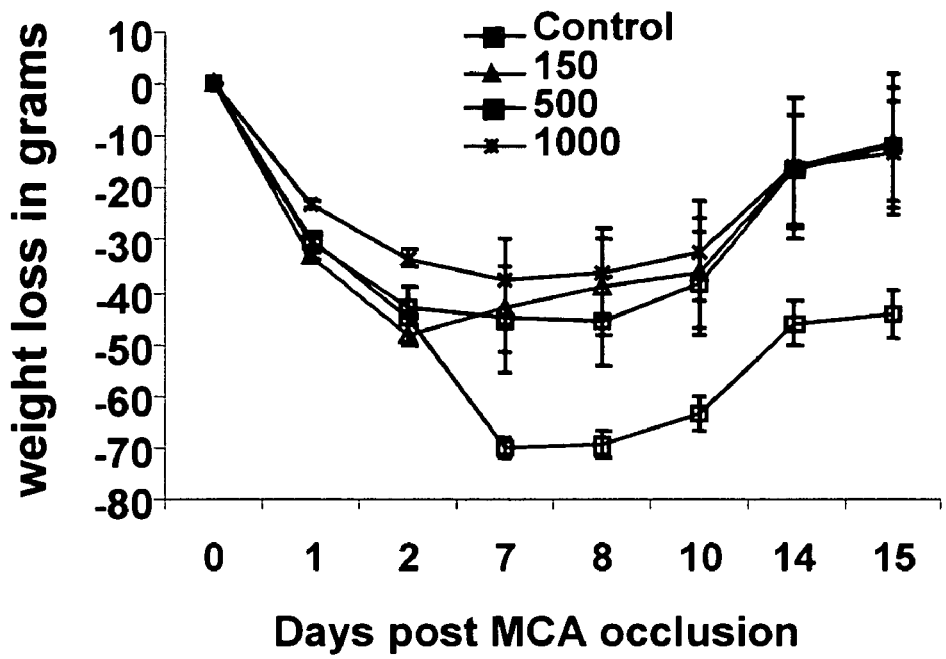
FIG. 14 shows that poly-Glu,Tyr significantly improves the recovery in body weight when injected 6 hours post MCA occlusion in all doses: 150 μg, 500 μg, and 1000 μg. The treated groups differ significantly from the control group (n=13) from day 8 post occlusion till the end of the experiment on day 15.

The beneficial effect of the treatment with poly-Glu,Tyr following induction of cerebral ischemia reflects not only in functional and morphological measures, as shown above, but rather improves the general welfare of the animals as indicated by the significantly better recovery of their body weight. The severe trauma of permanent MCA occlusion causes, in addition to neurological functional loss, dramatic reduction in body weight of about 25% at the first week. The rats immunized with different doses of poly-Glu,Tyr: 150 µg (n=14), 500 µg (n=15) and 1000 µg (n=13) 6 hours post-MCA occlusion were weighed daily from day 1 to day 15. The treated groups differ significantly from the control group (n=13) from day 8 post-occlusion till the end of the experiment on day 15 (t-test, p<0.05). The results depicted in FIG. 14 show that the ischemia-induced weight loss of the rats immunized with poly-Glu,Tyr was significantly lower than of the control group immunized with PBS; Thus, injection of poly-Glu,Tyr to rats 6 hours post-occlusion attenuates significantly the rate of body weight loss and speeds up their recovery.

Example 14

Pathological Evaluation of Rat Brains after MCA Occlusion

Exposure of animals to permanent MCA occlusion produces deleterious effects on the ischemic hemisphere and can project contralaterally. The hippocampal neurons are most vulnerable to stress conditions and necrotic cells can be observed in the CA1, CA2, and CA3 subfields of the hippocampus within 48 hours post-occlusion. We examined the effect of immunization with poly-Glu,Tyr 500 µg/rat on neuronal loss in the hippocampus of occluded rats.

Figure 15:
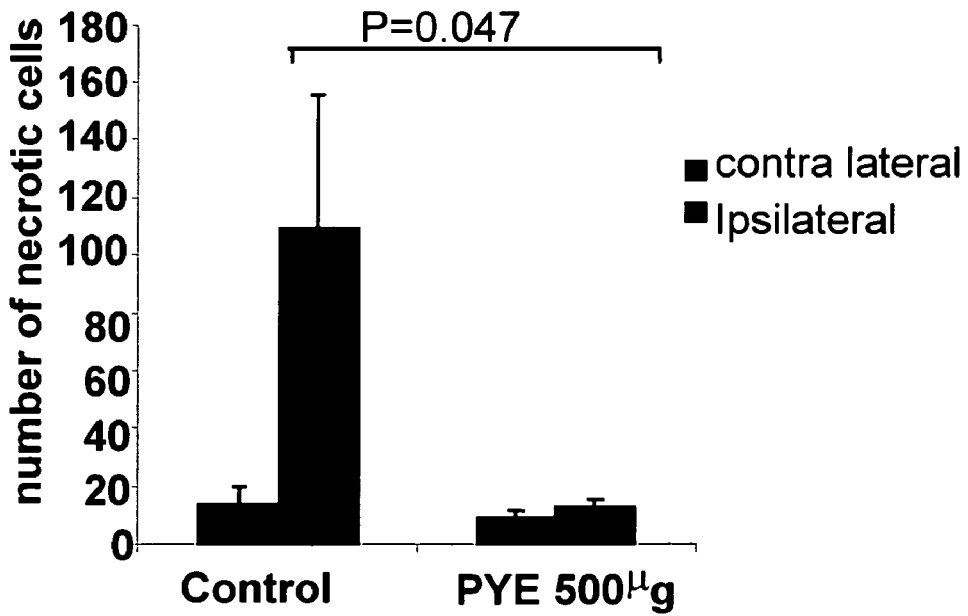
FIG. 15 shows that treatment with poly-Glu,Tyr protects hippocampal neurons from death caused by MCA occlusion. The average number of hippocampal necrotic cells per slice, as measured in 4-5 animals per group, is presented with the standard error.

FIG. 15 shows pathological evaluation (number of necrotic cells) of rat brains after MCA occlusion. Forty-eight hours after MCA occlusion, the brains of treated and control rats (4-5 animals per group) were analyzed. The average number of necrotic neurons was quantified in hippocampal slices of 100 µm thickness, 2-4 slices per each rat. Necrotic cells were counted in the CA1, CA2 and CA3 regions on both the ischemic contralateral and ipsilateral side of each slice. Immunization with poly-Glu,Tyr immediately after MCA occlusion protected significantly (p=0.047, ANOVA) hippocampal neurons from ischemia-induced degeneration. These results are in line with the observation that poly-Glu,Tyr attenuates ischemia-induced functional loss as measured up to 14 days post MCA occlusion, as shown in FIG. 12 above. These results further substantiate the potential of poly-Glu,Tyr to serve as neuroprotective therapy for stroke victims.

Section VI

Effect of Immunization with Poly-Glu,Tyr in the Induction of Neurogenesis after Stroke Diseases of the brain have singularly adverse effects on the quality and duration of life. Unlike many other tissues, the mature brain has limited regenerative capacity, and its unusual degree of cellular specialization restricts the extent to which residual healthy tissue can assume the function of damaged brain. However, cerebral neurons are derived from precursor cells that persist in the adult brain, so stimulation of endogenous neural precursors in the adult brain could have therapeutic potential. Neurogenesis occurs in discrete regions of the adult brain, including the rostral subventricular zone (SVZ) of the lateral ventricles and the subgranular zone (SGZ) of the dentate gyrus (DG). Neurons that arise in the SVZ travel via the rostral migratory stream to the olfactory bulb and also enter association neocortex, and new neurons leaving the SGZ migrate into the adjacent DG granule cell layer.

Pathological events can stimulate neurogenesis in the adult brain. There is substantial evidence supporting enhanced cell proliferation after ischemic injury in regions of the brain known to harbor neural stem cells. Ischemic brain injury triggers molecular and cellular repair mechanisms that contribute to recovery and may include ischemic activation of neurogenesis in the adult brain.

Most of these studies involve the use of 5-bromo-2-deoxyuridine (BrdU), a thymidine analog incorporated into DNA during S phase of the cell cycle, that can be used to visualize cell proliferation. For example, in a focal model of ischemic injury, MCA occlusion (see Section V above), investigations of BrdU incorporation in rats at weekly intervals, after either MCA occlusion or a sham procedure, revealed an 8-fold increase in labeling in the ipsilateral SGZ at 7 days after ischemia compared with sham-operated controls (Jin et al., 2001).

It is thus of interest to examine the effect of poly-Glu,Tyr on adult neurogenesis in the brain after stroke.

Example 15

Effect of Poly-Glu,Tyr on Adult Neurogenesis after Focal Ischemia in Rats

To test the effect of poly-Glu,Tyr on adult neurogenesis in rats after focal ischemia, MCA occlusion is induced in SPD rats as described in Section V above. The animals in the experiment are: (a) rats with 28 days of focal ischemia treated with vehicle (PBS) (n=10); (b) rats with 28 days of focal ischemia treated with 500 µg poly-Glu,Tyr in PBS (n=10); (c) rats with 14 days of focal ischemia treated with vehicle (PBS) (n=5); (d) rats with 14 days of focal ischemia treated with 500 µg poly-Glu,Tyr in PBS (n=5); (e) untreated naïve rats (n=5); and (f) naïve rats treated with 500 µg poly-Glu,Tyr (n=5).

The cell proliferation marker BrdU (Sigma) is injected (i.p.) at a dosage of 50 mg/kg body weight, twice daily for 14 days (starting 1 day after induction of ischemia). BrdU is dissolved in PBS using sonication and filtered before use. Animals are sacrificed 28 days after the induction of ischemia.

For brain excision, rats are anesthetized with 6 ml chloral hydrate solution (4 g/100 ml). Transcardial perfusion is performed first with 0.1 M PBS and then with 4% paraformaldehyde in PBS, followed by removal of the brain and post-fixing in 4% paraformaldehyde in PBS (overnight). Brains are transferred into 30% sucrose solution and stored at 4° C. Freezing of brains is carried out in 2-methylbutane at −80° C.

The analysis is carried out by: (i) Sectioning—brains are cut coronally on a cryomicrotome (thickness of slices ~25 µm), slices are selected (subventricular zone of the lateral ventricle/hippocampus with area dentata and CA1 cell layer), and transferred in cryoprotection solution (CPS=ethyleneglycol/glycerol/PBS 1:1:2) at −20° C. during the experiments and afterwards at 4-6° C.; (ii) Fluorescence double-immunostaining of BrdU/NeuN and BrdU with glial markers (for oligodendrocytes and astrocytes) of selected regions (SVZ, SGL, striatum, cortex) using confocal laser scan microscopy; (iii) BrdU$^+$ cells and double-labeled cells (BrdU/neuronal and glial markers) in the SVZ, SGL, striatum, and cortex, are counted from at least 6 slices per brain; (iv) Quantitative and statistical analyses of number of these cells and their density.

Results showing induction of proliferation and/or differentiation of adult stem cells in the brain will indicate that poly-Glu,Tyr has a positive effect on adult neurogenesis in the brain after ischemia.

Section VII

Neuroprotective Effect of Poly-Glu,Tyr in Motor Neurone Diseases

Amyotrophic Lateral Sclerosis (ALS), also known as Lou Gehrig's disease, is the most common form of motor neurone diseases (MND), a group of related diseases affecting the motor neurones in the brain (upper motor neurons) and spinal cord (lower motor neurons). Motor neurones (or moton neurons) are the nerve cells along which the brain sends instructions, in the form of electrical impulses, to the muscles. Degeneration of the motor neurones leads to weakness and wasting of muscles. This generally occurs in arms or legs initially, some groups of muscles being affected more than others. In ALS, degeneration of both the upper and lower motor neurones occurs. Less common forms are primary lateral sclerosis and progressive muscular atrophy, in which a more selective degeneration of either the upper or lower motor neurons, respectively, is observed.

ALS is a chronic, progressive neurodegenerative disease characterized by gradual degeneration of the nerve cells in the CNS that control voluntary muscle movement, muscle weakness, stiffness and fasciculations (muscle twitching). The progressive loss of motor neurons leads to gradual skeletal muscle atrophy and to inevitable death, usually within 2-3 to ten years of the disease onset. Muscular weakness and atrophy and signs of anterior horn cell dysfunction are initially noted most often in the hands and less often in the feet. The site of onset is random and progression is asymmetric.

There is no cure for ALS. The etiology of the disorder is usually unknown, though a subgroup of familial cases arises from genetic mutations. Thirty thousand people throughout the U.S. currently have ALS, and 8,000 new cases are diagnosed each year. ALS occurs worldwide, with no age, ethnic or economic boundaries.

Oxidative stress is characterized by accumulation of free radicals that can lead to motor neuron death. Free radicals damage components of the cells' membranes, proteins or genetic material by "oxidizing" them. These free radicals may be generated when the enzyme SOD malfunctions, either because of genetic mutation as occurs in some familial ALS patients or because of the chemical environment of the nerve cells, or they may be generated as a result of glutamate excitotoxicity, or for some other reason.

For spinal motor neurons, rapid glutamate removal following synaptic activity is accomplished by the glutamate transporter EAAT2 present in astrocytes. Decrease in EAAT2 activity and protein level was found in brain tissue of ALS patients. This could lead to increased extracellular concentration of glutamate and death of motor neurons.

Excessive glutamate rapidly kills cells in the brain and spinal cord. Cells of ALS patients and animal models have been shown to exhibit major defects in glutamate neurotransmission and it is established that glutamate-based neurotoxicity is part of ALS, part of a process leading to motor neurons' death. The sole drug approved for treatment of ALS is Riluzole, a glutamate release inhibitor. However, its effects are clearly modest—it can prolong the life of ALS patients approximately three months, but it does not halt the degenerative disease or repair damage already incurred. Therefore, the search for additional therapies continues.

The results in Section I above show that poly-Glu,Tyr is effective in protecting RGCs from glutamate toxicity and indicate that poly-Glu,Tyr may be a candidate for treatment of ALS and other motor neurone diseases.

Materials and Methods—Section VII

Animals. Transgenic mice overexpressing the defective human mutant SOD1 allele containing the Gly93→Ala (G93A) gene (B6SJL-TgN(SOD1-G93A)1Gur (herein "ALS mice") are from The Jackson Laboratory (Bar Harbor, Me., USA). Adult female mice (12 weeks old, 20-25 g) of the C57BL/6JO1aHsd strain are from Harlan Winkelmann (Borchen, Germany).

ALS model. ALS mice (n=15) are immunized with poly-Glu,Tyr in PBS (one SC injection in the flank). Control mice are injected with PBS. The mice may be given one or more booster injections later on. Additional ALS mice are not immunized and serve as a control for spontaneous progression of the disease. The muscle strength is evaluated by blindly testing the time of hanging of each mouse on a rotating vertical rod. Since the maximal time that most of the animals are able to hang on the rotating rod is 5 minutes, each experiment is continued up to 5 minutes.

Muscle strength test. The test is performed as previously described (Kong and Xu, 1998). Mice are allowed to grasp and hold onto a vertical wire (2 mm in diameter) with a small loop at the lower end. A vertical wire allows mice to use both fore- and hind-limbs to grab onto the wire. The wire is maintained in a vertically oriented circular motion (the circle radius is 10 cm) at 24 rpm. The time that the mouse is able to hang onto the wire is recorded with a timer. Because most mice fell within 5 min, the testing is cut off at 5 min. Mice are usually tested once a week and testing continues until they can no longer hang onto the wire.

Data analysis. Survival data are analyzed by the Mantel-Cox test or Cox's proportional hazards regression analysis. Statistical significance is tested by one-way ANOVA, followed by a post-hoc Student-Neuman-Keuls procedure with the SPSS—PC software program (SPSS, Chicago, Ill.).

Example 16

Effect of Poly-Glu,Tyr Immunization in Protection from Motor Nerve Degeneration in Transgenic Mutant SOD1 Mice (ALS Mice)

To test whether poly-Glu,Tyr immunization can protect from the progression of motor neuron degeneration, an animal model of ALS is used, For example, ALS mice SOD1 (n=15) are immunized with different doses (25-500 µg) of poly-Glu,Tyr in PBS, at different ages (for example, when they are 45 days old), and one or more boosts are administered later on. A control group (n=15) of ALS mice is not immunized with poly-Glu,Tyr. The mice are then tested several times per week for muscle strength, by blindly testing the time of hanging on a rotating vertical rod. Each experiment lasts 5 min.

The onset of the decline in muscle strength varies among individual mice. To assess the effect of the immunization on the rate of decline in each mouse, the muscle strength at any given time is compared to that found one week before the decline began. The effect of poly-Glu,Tyr is assessed by the average hanging time for each animal per week. Mice immunized with poly-Glu,Tyr are expected to exhibit longer hanging time than the non-immunized mice, a significantly lower rate of muscle strength decline, regardless of their strength on the day of immunization, and to retain motor power for a longer period of time as compared to non-immunized animals.

The beneficial effect of poly-Glu,Tyr immunization is expected also to reflect in the body weight and in the mortality rate of the transgenic mice. Poly-Glu,Tyr immunized transgenic mice are expected to show a slower loss of body weight and a prolonged life span.

Example 17

Effect of Poly-Glu,Tyr Immunization on Protection Against Motor Neuron Degeneration after Facial Nerve Axotomy (Acute Motor Neuron Disorder Model)

Transection of the facial nerve in the adult mouse is known to cause an easily visible late degeneration of 20% to 35% of the axotomized motor neurons. Therefore, axotomy of the facial nerve provides a model for ALS, which is a disease characterized by progressive motor neuron loss. The effect of immunization on the survival and function of the neurons in the facial nerve axotomy model is indicative for the potential of the treatment in attenuating neuronal loss in ALS patients.

Adult female mice of the C57BL/6JOlaHsd strain are subjected to unilateral facial nerve axotomy. Mice in the experimental group are immunized with poly-Glu,Tyr in PBS (25-100 µg). Control animals are axotomized and are either untreated or injected with PBS. Seven days later a facial-facial anastamosis (FFA) is created in anesthetized mice (100 mg ketamine plus 5 mg xylazine per kg body weight) by microsurgical reconnection of the proximal stump to the distal stump with two 11-0 epineural sutures (Ethicon EH 7438G, Norderstedt, Germany). The wound is closed with three 4-0 skin sutures. For assessment of recovery, facial motor neurons supplying the whiskerpad muscles are retrogradely labeled by injection of 30 µl of 1% aqueous solution of the fluorescent retrograde tracer FluoroGold plus 2% dimethylsulfoxide (DMSO) injected into the muscles of each whisker pad. Seven days later, the mice are re-anesthetized and perfused transcardially with 0.9% NaCl followed by fixation with 4% paraformaldehyde in 0.1 M phosphate buffer, pH 7.4, for 20 min. The brains are removed and 50-µm-thick coronal sections are cut through the brain stems with a vibratome. Sections are observed with a Zeiss Axioskop 50 epifluorescence microscope through a custom-made HQ-Schmalband-filter set for FluoroGold (AHF Analysentechnik, Tubingen, Germany).

Eight or more weeks after axotomy, the mean number of FluoroGold-labeled motor neurons in the mice immunized with poly-Glu,Tyr is expected to be significantly larger than the number obtained in the group injected with PBS alone. Treatment with poly-Glu,Tyr should have no effect on the number of motor neurons in the unlesioned facial nucleus.

Retrograde neuronal labeling after injection of FluoroGold into the whiskerpad is not expected to show differences in the localization or amount of motor neurons in the intact facial nucleus between mice immunized with poly-Glu,Tyr and mice injected with PBS. In contrast, the lesioned facial nucleus, after pre-treatment of mice with poly-Glu,Tyr, is expected to contain significantly more labeled motor neurons than that of the lesioned facial nucleus in control animals pre-treated with PBS.

Example 18

Effect of Poly-Glu,Tyr Administration on Preservation of Motor Neuron Activity after Acute Axotomy To determine whether the larger number of motor neurons found in the poly-Glu,Tyr-treated axotomized mice than in the controls is associated with functional improvement, whisking behavior is biometrically analyzed. Baseline parameters of whisking behavior are documented in intact control mice. Under normal physiological conditions, the mystacial vibrissae are erect with anterior orientation. Their simultaneous sweeps, known as "whisking" or "sniffing", occur 5-11 times per second. The key movements of this motor activity are the protraction and retraction of the vibrissal hairs by the piloerector muscles, which are innervated by the buccal branch of the facial nerve. When the facial nerve is transected, the vibrissae acquire a caudal orientation and remain motionless.

Using this model, the following parameters are evaluated: (i) protraction (forward movement of the vibrissae), measured by the rostrally opened angle between the mid-sagittal plane and the hair shaft (large protractions are represented by small angle values); (ii) whisking frequency, represented by cycles of protraction and retraction (passive backward movement) per second; (iii) amplitude—the difference, in degrees, between maximal retraction and maximal protraction; (iv) angular velocity during protraction, in degrees per second; and (v) angular acceleration during protraction, in degrees per second (Angelov et al., 2003).

Mice subjected to facial nerve axotomy and poly-Glu,Tyr immunization are expected to exhibit significantly better whisking activity than the other groups of mice. This can be best demonstrated by the amplitude, the angular velocity during protraction, and the angular acceleration during protraction.

Section VIII Neuroprotective Effect of Poly-Glu,Tyr in Huntington's Disease

Huntington's Disease (HD) is a hereditary brain disorder that affects people of all races all over the world. It is a degenerative disease whose symptoms are caused by the loss of cells in the basal ganglia of the brain. This damage to cells affects cognitive ability (thinking, judgment, memory), movement, and emotional control. Symptoms appear gradually, usually in midlife, between the ages of 30 and 50. However, the disease can strike young children (juvenile form) and the elderly. Huntington's Disease occurs in approximately 1 in 10,000 people in most western countries. Males and females have an equal chance of inheriting the gene from an affected parent. HD is characterized by uncontrollable, dance-like movements and personality changes. HD patients develop slurred speech, an unsteady walk and difficulty in swallowing. People do not die from HD itself but rather from a complication of the disease, such as choking or infection. Death generally occurs about 15 to 20 years after onset.

In 1993, the mutation that causes HD was identified as an unstable expansion of CAG repeats in the IT15 gene encoding huntingtin, a protein of unknown function. The CAG repeat expansion results in an increased stretch of glutamines in the N-terminal portion of the protein, which is widely expressed in brain and peripheral tissues. The exact mechanisms underlying neuronal death in Huntington's disease remain unknown. Proposed mechanisms have included activation of caspases or other triggers of apoptosis, mitochondrial or metabolic toxicity, and interference with gene transcription. There is no effective treatment for HD. Drugs currently used for treatment of HD do not alter the course of the disease but treat common symptoms such as depression and anxiety and reduce involuntary movements. Some drugs have significant side effects. Recent advances in the understanding of the pathophysiology of neurodegenerative diseases in general, and of Huntington's disease in particular, have suggested new therapeutic strategies aimed at slowing progression or delay onset of the neurodegeneration caused by the disease. Neuroprotective therapy for HD is a new approach that can postpone the onset of the neurodegenerative effects and attenuate the rate of disease progression. Poly-Glu,Tyr may be a suitable candidate for the treatment of HD patients.

Materials and Methods—Section VIII

Animals. Mice of the C57BL/6J strain (aged 8-13 weeks) are anesthetized by intraperitoneal administration of 80 mg/kg ketamine and 16 mg/kg xylazine, prior to their use in the experiments. Transgenic HD R6/2 mice overexpressing the human gene encoding huntingtin are obtained from the Jackson Laboratory.

Immunization. For immunization, poly-Glu,Tyr in PBS is injected SC at one site in the flank of the mice. Control mice are injected with vehicle only. The results in the glutamate toxicity model in Section I above showed that the regimen of repeated injections of poly-Glu,Tyr may lead to a sustained neuroprotective effect. Based on these results, the optimal neuroprotective effect in mice may be repeated 25-75 μg injections of poly-Glu,Tyr at 4 weeks or more intervals.

Example 19

Poly-Glu,Tyr in an Animal Model for Huntington's Disease

The beneficial effect of poly-Glu,Tyr immunization is examined for exertion of neuroprotective effects using the HD R6/2 transgenic mice test system or another suitable model. R6/2 transgenic mice overexpress the mutated human huntingtin gene that includes the insertion of multiple CAG repeats (Mangiarini et al., 1996). These mice show progressive behavioral-motor deficits starting as early as 5-6 weeks of age, and leading to premature death at 10-14 weeks. The symptoms include low body weight, clasping, tremor and convulsions.

Different doses of poly-Glu,Tyr are tested for immunization (from 10 to 500, preferably 25 to 75 μg poly-Glu,Tyr/mouse) that are injected to mice at different ages, and thereafter at different intervals (4 weeks or more). For example, one group of mice is immunized with 50 μg poly-Glu,Tyr when they are 45 days old, and every 4 weeks thereafter, and a second group is immunized with 75 μg poly-Glu,Tyr on day 60 of age and every 4 weeks thereafter. The control group is injected with PBS starting on the same age as the tested group and thereafter at the same intervals. Motor neurological functions are evaluated using the rotarod performance test which assesses the capacity of the mice to stay on a rotating rod. For this test, mice are placed on a rod rotating at 2, 5, 15 and 25 rpm. The time until the mouse falls off the rotating rod (best of three attempts, up to 180 sec for each trial) is used as the measure of animal motor-function. Each mouse is tested twice weekly and the two scores averaged. It can be expected that immunization with poly-Glu,Tyr will improve the rotarod performance of the treated mice compared to untreated (control) mice during the follow-up period (8-14 weeks).

The poly-Glu,Tyr-immunized and untreated HD R6/2 transgenic mice are weighed twice a week at the same time during the day. No body weight loss is expected following immunization with any of the poly-Glu,Tyr doses compared to the control group. It can also be expected that poly-Glu,Tyr immunization will delay mortality and onset of disease of HD R6/2 mice. It is also expected that examination of the immunized mice's brain will show fewer dead neurons than in non-treated mice.

Example 20

Treatment of Huntington's Disease in Humans

The primary objective of the human study is to evaluate the tolerability, safety and immunological response of the serial administration of a suitable dose, for example, 20 mg or 2×20 mg dose of poly-Glu,Tyr in PBS, versus placebo, in patients suffering from Huntington's disease. The secondary objective of the study is to evaluate the neurological course of patients with HD disease following administration of poly-Glu,Tyr, by measuring the following neurological clinical parameters: Unified Huntington's Disease Rating Scale (UHDRS) and Total Motor Scale (TMS).UHDRS is a research tool developed by the Huntington Study Group (HSG). The purpose of the scale is to allow the researchers to grade the symptoms of HD in a way that allows them to make accurate comparisons between individual patients, and to better chart the course of the disease in patients. The scale is divided into a number of different subscales, including the Total Motor Score 4 (TMS-4). In the human trial, a primary end-point is the change over a period of time, e.g. one-year period, in the TMS-4 subscale of the UHDRS, the standard rating scale for trials in HD. The pre-determined and end-points of the trial (such as UHDRS scores) are compared for the patients on poly-Glu,Tyr and the placebo. Any improvement in the treated patients may indicate the possibility that the drug can be said to have had some kind of impact on Huntington's disease.

Section IX

Effect OF Poly-Glu,Tyr on $CD4^+CD25^+$ T Regulatory (Treg) Cells

It is becoming increasingly clear that the body, to protect itself against tumor growth or CNS neurodegeneration, needs to elicit autoimmunity against self-antigens associated with the tumor (Dummer et al., 2002) or self-antigens residing in the site of degeneration (Moalem et al., 1999; Mizrahi et al., 2002), respectively. Normally, autoimmunity is suppressed by naturally occurring regulatory $CD4^+CD25^+$ T cells (Treg) (Shevach et al., 2001; Sakaguchi et al., 1995). Depletion of Treg enhances neuronal survival after CNS insults (Kipnis et al., 2002a) and increases spontaneous anti-tumor autoimmunity (Sakaguchi et al., 2001). Therefore, to elicit the desired autoimmune response for anti-tumor therapy or protection of CNS neurons at risk of degeneration, the Treg-imposed suppression must be blocked (Kipnis et al., 2002a; Schwartz and Kipnis, 2002).

Co-culturing of Teff cells (a $CD4^+CD25^-$ population) with Treg isolated from naïve mice results in suppression of Teff proliferation. The suppressive potency depends on the Treg/Teff ratio and the state of Treg activation: the suppression is significantly increased if the Treg cells are activated before being added to Teff (Thornton and Shevach, 1998, 2000). Inhibition of proliferation of Teff, assayed by [$^3$H]thymidine incorporation, can therefore be taken as a measure of the suppressive effect of Treg.

In U.S. Provisional Application No. 60/472,410 of the applicants, filed May 22, 2003, hereby incorporated by reference in its entirety as if fully disclosed herein, the inventor M. Schwartz has shown that the neurotransmitter dopamine, a member of the catecholamine family, acts on Treg cells and alters their suppressive effect on effector T cells. The inventors have then stipulated that agents that down-regulate the suppressive activity of Treg cells on Teff cells can be used for treatment of a neurodegenerative condition, disorder or disease. In U.S. Provisional Application No. 60/472,415 of the applicants, filed May 22, 2003, hereby incorporated by reference in its entirety as if fully disclosed herein, the inventor M. Schwartz has disclosed that down-regulation or up-regulation of the suppressive activity of Treg cells on Teff cells can be used for treatment of cancer or autoimmune diseases, respectively. In U.S. Provisional Application No. 60/527,772, filed Dec. 9, 2003, from which the present application is a non-provisional application, the contents of said provisional application being hereby incorporated by reference in its entirety as if fully disclosed herein, the inventor M. Schwartz has then shown the inhibitory effect of poly-Glu,Tyr on Treg cells.

Materials and Methods—Section IX

Animals. Inbred adult male wild-type BALB/c mice were used in the experiments.

Antibodies and reagents. Mouse recombinant IL-2 (mrIL-2) and anti-mouse ξ-CD3 (anti-CD3; clone 145-2C11) were purchased from R&D Systems (Minneapolis, Minn., USA). Rat anti-mouse phycoerythrin (PE)-conjugated CD25 antibody (PC61) was purchased from Pharmingen (Becton-Dickinson, Franklin Lakes, N.J., USA).

Preparation of Lymphocytes. Donor Mice Lymph Nodes (Axillary, Inguinal, superficial cervical, mandibular, and mesenteric) were ruptured through mesh. The lymphocytes were washed with hypotonic buffer (ACK) to lyse red blood cells.

Preparation of Splenocytes. Donor Splenocytes from Mice were Obtained by rupturing the spleen and following conventional procedures. The splenocytes were washed with hypotonic buffer (ACK) to lyse red blood cells.

Purification of $CD4^+CD25^+$ and $CD4^+CD25^-$ T cells. Lymph nodes were harvested and mashed. T cells were enriched by negative selection and purified on CD3-cell columns (MTCC-25; R&D Systems). The enriched T cells were incubated with anti-CD8 microbeads (Miltenyi Biotec, Bergisch Gladbach, Germany), and negatively selected $CD4^+$ T cells were incubated with PE-conjugated anti-CD25 (30 µg/$10^8$ cells) in PBS/2% fetal calf serum. They were then washed and incubated with anti-PE microbeads (Miltenyi Biotec) and subjected to magnetic separation with AutoMACS (Miltenyi Biotec). The retained cells were eluted from the column as purified $CD4^+CD25^+$ cells. The negative fraction consisted of $CD4^+CD25^-$ T cells. Cell purity was checked by FACSort (Becton-Dickinson) and typically ranged from 88% to 95%. Purified cells were cultured in 24-well plates (1 ml).

Activation of $CD4^+CD25^+$ regulatory T cells. Purified regulatory T cells (Treg; $0.5 \times 10^6$ cells/ml) were activated in RPMI medium supplemented with L-glutamine (2 mM), 2-mercaptoethanol ($5 \times 10^{-5}$ M), sodium pyruvate (1 mM), penicillin (100 IU/ml), streptomycin (100 µg/ml), non-essential amino acids (1 ml/100 ml), and autologous serum 2% (vol/vol) in the presence of mrIL-2 (5 ng/ml) and soluble anti-CD3 antibodies (1 µg/ml). Irradiated (2500 rad) mice splenocytes ($1.5 \times 10^6$ cells/ml) were added to the culture. Cells were activated for 24 or 96 hours. In some of the experiments, poly-Glu,Tyr (20 µg/ml) was added to the culture every 24 h during activation.

Inhibition assay (co-culturing of Teff with Treg). Naïve effector T cells (Teff; $50 \times 10^3$ cells/well) were co-cultured with decreasing numbers of activated Treg for 72 h in 96-well flat-bottomed plates in the presence of irradiated splenocytes ($10^6$/ml) supplemented with anti-CD3 antibodies [$^3$H]-thymidine (1 µCi/well) was added for the last 16 h of culture. After the cells were harvested, their proliferation was measured by their [$^3$H]-thymidine incorporation.

Example 21

Poly-Glu,Tyr Alleviates the Suppressive Activity Mediated by Treg Cells

Figure 16A:
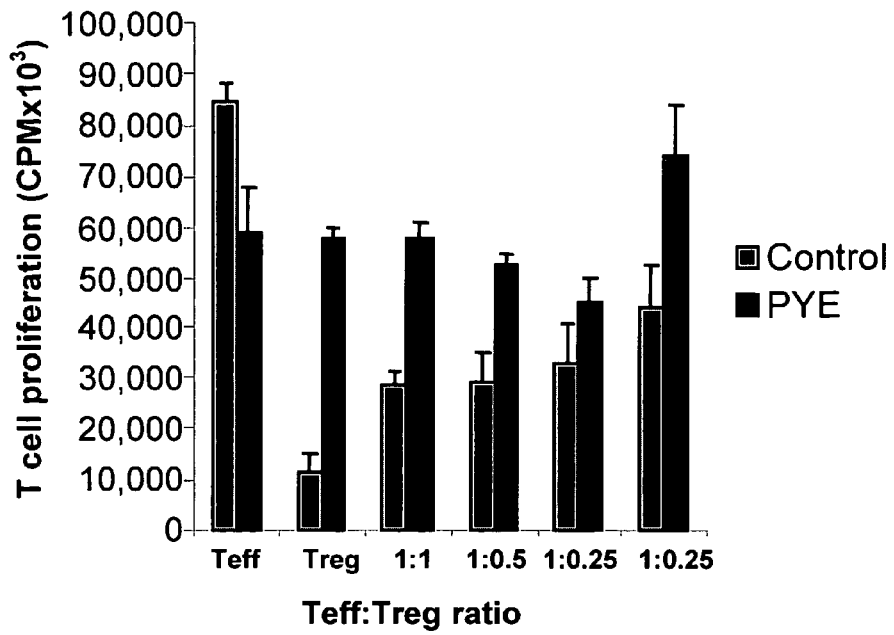
FIGS. 16A-16B show that incubation of activated T regulatory (Treg) cells for 2 h with poly-Glu,Tyr prior to their co-culturing with T effector (Teff) cells (TregYE) alleviated the Treg suppressive activity on Teff, as measured by the resulting proliferation of Teff, compared to that obtained with activated Treg not exposed to poly-Glu,Tyr (control).
Figure 16B:
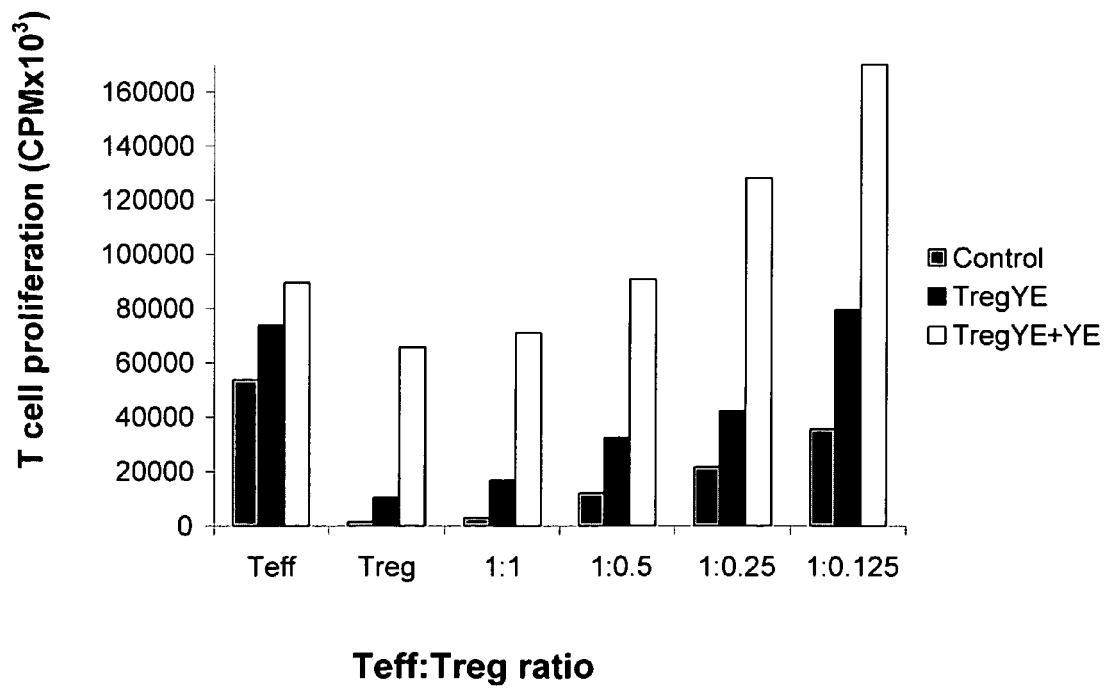

Naïve Teff cells ($50 \times 10^3$ cells/well) were co-cultured with decreasing numbers (50, 25, 12.5 and $6.5 \times 10^3$ cells/well) of Treg cells that have been activated for 24 h with anti-CD3 and mrIL-2. The activation of the Treg cells was carried out in the absence of poly-Glu,Tyr (control) or, after 24 h, activated Treg cells were incubated for 2 h with poly-Glu,Tyr (20 µg/ml in PBS) before co-culturing them with Teff (TregYE). To some of the co-cultures of Teff and Treg, poly-Glu,Tyr (20 µg/ml) was added (TregYE+YE) and the co-cultures were further incubated. FIGS. 16A-16B show that incubation of the activated Treg for 2 h with poly-Glu,Tyr prior to their co-culturing with Teff (TregYE) alleviated the Treg suppressive activity on Teff, as measured by the resulting proliferation of Teff, compared to that obtained with activated Treg not exposed to poly-Glu,Tyr (control). FIG. 16B shows that the effect was even more significant in the co-cultures of Teff and TregYE to which poly-Glu,Tyr was added (TregYE+YE) as shown by the significantly higher Teff proliferation. The proliferation of Teff also increased with decreasing concentrations of activated Treg. T cell proliferation was assayed by incorporation of [$^3$H]-thymidine into effector T cells co-cultured with Treg. Recorded values are from one representative experiment out of three and are expressed as means ±SD of 4 replicates.

Example 22

Poly-Glu,Tyr Causes Changes in the Cytokine Phenotype of the Treg Cells

To test the cytokine profile of Treg cells upon incubation with poly-Glu,Tyr, Treg cells were incubated with mrIL-2 and anti-CD3 for 72 hours, washed and further incubated for 48 hours using fresh medium and poly-Glu,Tyr (20 µg/ml in PBS). Conditioned media were collected 24 hours after incubation with poly-Glu,Tyr and analyzed for cytokines using commercial kits for INF-γ, IL-10, TGF-β and IL-2, according to the manufacturer's instructions (all kits from R&D Systems, Biotest Ltd., Kfar Saba, Israel).

Figure 17A:
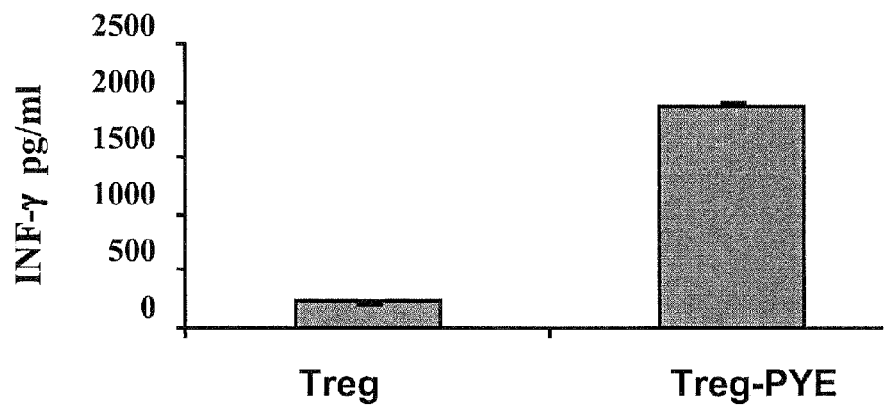
FIGS. 17A-17D show that the cytokine phenotype of the Treg cells is changed in the presence of poly-Glu,Tyr and it becomes similar to the phenotype of Teff cells: there is up-regulation of IFN-γ (A), TGF-β (B) and IL-2 (C) and down-regulation of IL-10(D).
Figure 17B:
Figure 17C:
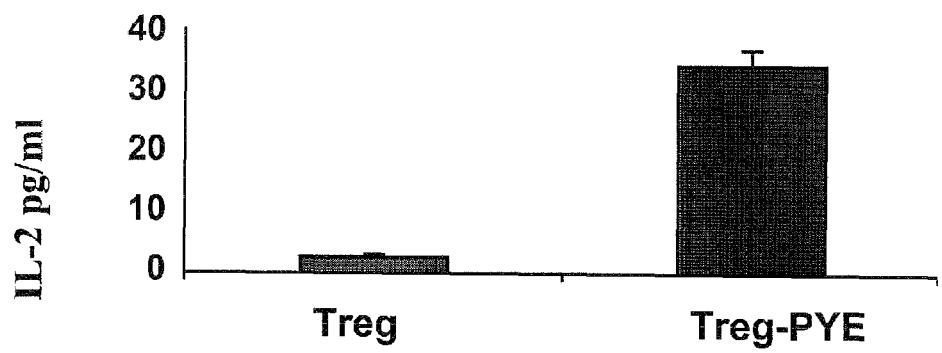
Figure 17D:
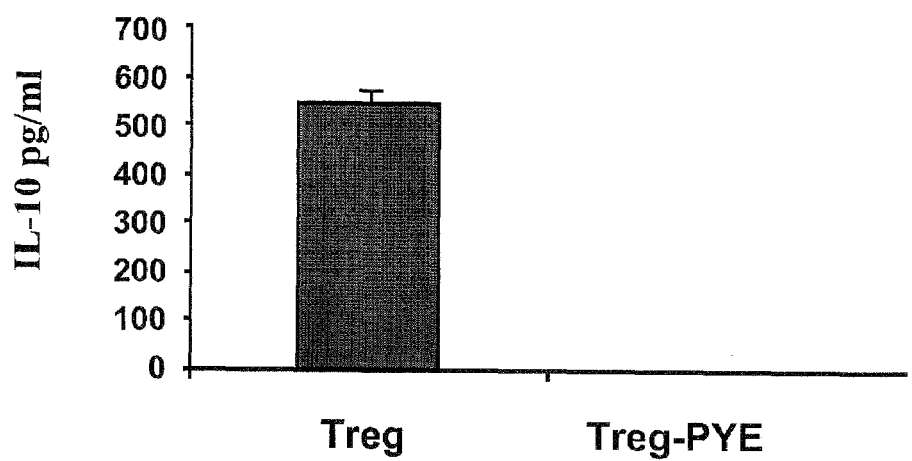

FIGS. 17A-17D show that the cytokine phenotype of the T regulatory cells is changed in the presence of poly-Glu,Tyr and it becomes similar to the phenotype of T effector cells, namely, there is up regulation of IFN-γ (FIG. 17A), TGF-β (17B) and IL-2 (FIG. 17C) and down regulation of IL-10 (FIG. 17D). The change of the cytokine secretion profile of the Treg cells after incubation with poly-Glu,Tyr reflects the changes induced by poly-Glu,Tyr in the biological activity of the Treg cells. The inhibitory cytokine IL-10 secretion is significantly reduced while secretion of the pro-inflammatory cytokine INF-γ is elevated. The appearance of IL-2 secretion goes in line with the observation of increased proliferation of the Treg cells in the presence of poly-Glu,Tyr.

Section X

Poly-Glu,Tyr Immunization is Protective in the Treatment of Psychiatric Disorders Psychological trauma, like physical insults to the CNS, can cause widespread, long-term changes in neurological and neurohormonal functioning, which appear to be related to morphological changes. There is evidence that an individual's mental or emotional state or both can directly affect immune system function (de Groot et al., 2002; McEwen, 2002; Dhabhar and McEwen, 1999). Immune cell activity has undeservedly acquired a bad reputation in the CNS. This is because, in healthy brains, the CNS is assumed to be a site of "immune privilege". Immune abnormalities have been reported in patients with schizophrenia, and there have been numerous attempts to find a connection between schizophrenia and autoimmune disease. However, studies over the last 60 years aimed at identifying an autoimmune basis for schizophrenia have yielded no valid evidence that it exists.

Contrary to long-held belief, however, the effect of the immune system on the nervous system can also be beneficial. Protection against neurodegenerative conditions in the CNS is T-cell dependent. The spontaneous ability to fight off the sequelae of a mechanical (e.g. crush) injury or a biochemical insult (e.g. from glutamate toxicity) to the CNS (Schwartz and Kipnis, 2002; Kipnis et al., 2002a) is suppressed by naturally occurring Treg cells, which comprise approximately 10% of the $CD4^+$ T-cell population and are thought to be responsible for peripheral tolerance of autoimmune T cells (Shevach et al., 2001; Thornton and Shevach, 1998; Nakamura et al., 2001).

In U.S. Provisional Application No. 60/527,772, filed Dec. 9, 2003, from which the present application is a non-provisional application, said provisional application hereby incorporated by reference in its entirety as if fully disclosed herein, the inventors disclosed that protection against consequences of psychological trauma is T-cell dependent and is suppressed by naturally occurring Treg cells. Since the Treg cells suppress the ability to withstand psychological trauma, down-regulation of Treg and/or modulation of the immune response and/or modulation of the autoimmune response in an individual can be beneficial and can improve the individual's ability to withstand and cope with stressful conditions.

Previous studies have shown that exposure of rats or mice to a predator (cat) or odor of a predator (thoroughly soiled cat litter) for 10 minutes causes major stress in these animals (Adamec et al., 1999). Using this stress model in the above U.S. Provisional Application No. 60/527,772, the inventors have first exposed nude BALB/c mice reconstituted with whole splenocytes and nude BALB/c mice replenished with splenocytes devoid of Treg to the odor of a cat, as previously described (Cohen et al., 2003). Seven days later, the inventors assessed the behavioral responses to two sequentially administered behavioral challenges, the elevated plus-maze and the acoustic startle response, which together provide a framework for selected cutoff behavioral criteria (CBC). By classifying the tested mice as either "maladapted" or "well adapted", the prevalence of the more severely affected animals could be determined. Comparison of the nude BALB/c mice reconstituted with whole splenocytes and the nude BALB/c mice replenished with splenocytes devoid of Treg showed that the incidence (20%) of maladaptation in the group of nude mice replenished with splenocytes devoid of Treg was significantly lower than in the group replenished with whole splenocytes (50%). The differences observed between the two groups were significant both in the acute startle response and in the time spent in closed arms of the maze. This was the first demonstration that cross-talk between the brain and the adaptive immune system (T cells) affects the consequences of a single instance of psychological trauma. Complete T cell deficiency was found to correlate with maladaptation to psychological stress, whereas removal of only a subpopulation of T cells, the naturally occurring suppressor T cells (Treg), improved the ability to adapt to the stress. This suggests that, in normal animals subjected to traumatic mental stress, the T cell-mediated response cannot reach its full therapeutic potential, as it is suppressed by the presence of the naturally occurring regulatory T cells.

Since poly-Glu,Tyr was shown in Section IX above to alleviate the suppressive activity of the Treg cells, we have then tested its effect in an animal model of psychotic behavior that simulates schizophrenia.

Materials and Methods—Section X

Animals. Inbred adult male C57B1/6J mice (8-12 weeks old) were housed in a light- and temperature-controlled room and matched for age in each experiment.

Drug solutions. Poly-Glu,Tyr was dissolved in PBS. Fresh solutions of dizocilpine maleate (MK-801; Sigma-Aldrich) were prepared in physiological saline (0.9% NaCl in sterile distilled water) for each batch of mice. Mice were injected with MK-801 or vehicle (PBS) 15 min before being subjected to behavioral tests.

Morris water maze (MWM) behavioral test. Spatial memory was assessed by performance on the Morris water maze task, a hippocampal-dependent visuo-spatial learning task. Mice were given four trials per day, for 4 consecutive days, to find the hidden platform located 1.5 cm below the water surface in a pool 1.4 m in diameter. Within the testing room only distal visuo-spatial cues were available to the mice for location of the submerged platform. The escape latency, i.e., the time required by the mouse to find and climb onto the platform, was recorded for up to 60s. Each mouse was allowed to remain on the platform for 30 s, and was then moved from the maze to its home cage. If the mouse did not find the platform within 120 s, it was manually placed on the platform and returned to its home cage after 30 s. The inter-trial interval was 30 s. On day 5 the platform was removed from the pool, and each mouse was tested by a probe trial for 60 s. On days 6-7 the platform was placed at the opposite location, and the mouse was retrained in four sessions. Data were recorded using an EthoVision automated tracking system (Noldus).

Example 23

Poly-Glu,Tyr Immunization is Protective Against Cognitive Impairment Induced by Psychotomimetic Agents Dizocilpine maleate, (+)MK-801, an antagonist of the N-methyl-D-aspartate (NMDA) receptor channel, act as a psychotomimetic agent, inducing (via neuro-transmitter imbalance) psychotic symptoms in healthy individuals and exacerbating psychotic symptoms in schizophrenic patients. We therefore used this compound in an animal model to induce psychotic behavior that simulates behavioral abnormalities associated with schizophrenia.

Administration of MK-801 also induces cognitive deficits in the mice. Numerous authors have reported an MK-801-induced learning deficit in acquisition of spatial memory (Whishaw and Auer, 1989; Ahlander et al., 1999) and non-spatial memory tasks (Griesbach et al., 1998). We therefore examined the effect of poly-Glu,Tyr immunization on the ability to prevent or reverse the cognitive deficit induced by MK-801.

Figure 18:
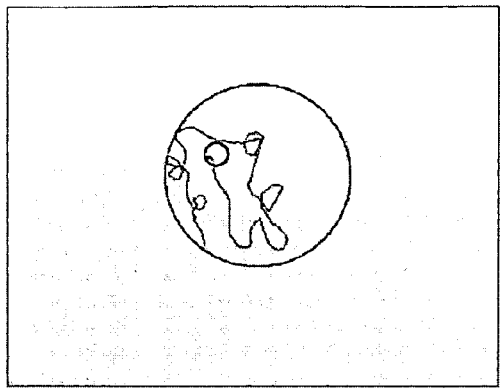
FIG. 18 are 4 panels depicting representative tracks of poly-Glu,Tyr-immunized mice (left panels) and of PBS-injected control mice (right panels) in the Morris water maze (MWM), after injection of the psychotomimetic drug MK-801.
Figure 18:
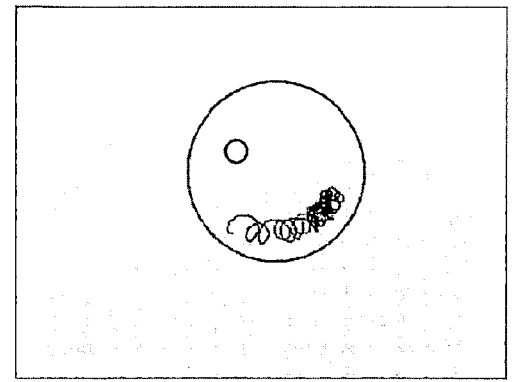
Figure 18:
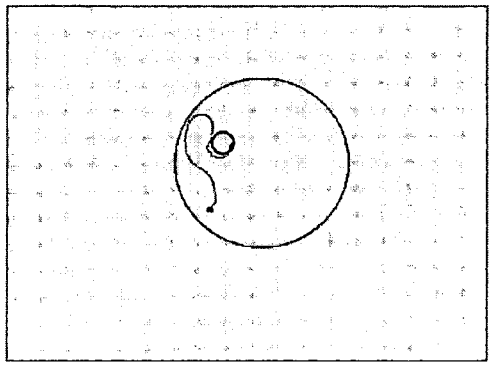
Figure 18:
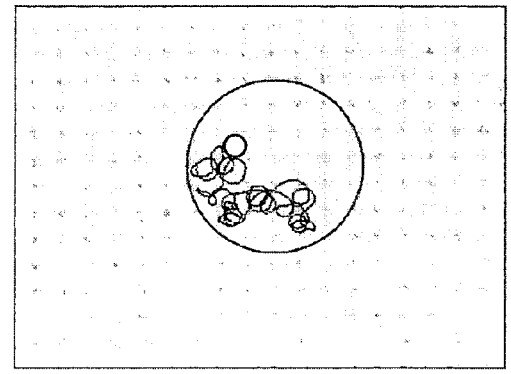

One week before administration of MK-801, each mouse was either immunized SC with poly-Glu,Tyr (25 µg/mouse) or with vehicle (PBS), and then injected i.p. with MK-801 (0.1 mg/kg) 15 min before the mouse was tested. Administration of MK-801 significantly impaired performance of a spatial memory task in the Morris water maze (MWM). FIG. 18 depicts representative tracks of MK-801-injected poly-Glu,Tyr-immunized mice and of MK-801-injected PBS-injected control mice when tested in the MWM at the first day (trails 1 and 4). As shown in FIG. 18, the swimming strategies of the poly-Glu,Tyr-immunized mice (left panels) and the PBS-treated controls (right panels) differed: the poly-Glu,Tyr-immunized mice employed more methodical swimming strategies than the controls. Thus, all the poly-Glu,Tyr-immunized mice learned to swim away from the wall to search for the platform in the inner 50% of the pool and to use the platform as a refuge when they found it. In contrast, the behavior of the PBS-immunized mice showed severe disturbances, including hyperactivity, swimming over the platform, and aimless swimming in circles.

Figure 19:
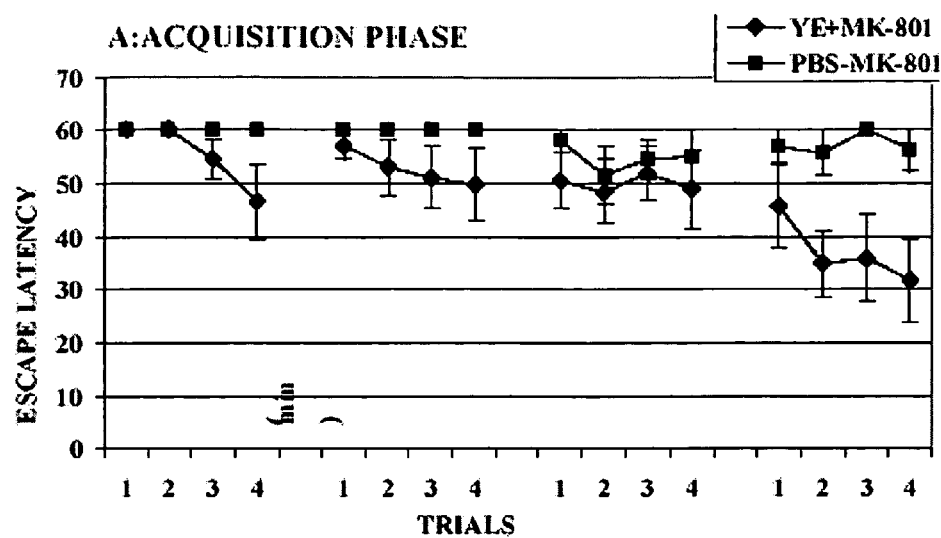
FIG. 19 shows performance of the acquisition phase in the MWM task by poly-Glu,Tyr-immunized mice (YE) and PBS-injected control mice after injection of the psychotomimetic drug MK-801.

Injection of MK-801 significantly impaired task acquisition in the MWM (increased escape latency) in the PBS-treated mice, but not in poly-Glu,Tyr-immunized mice (FIG. 19). During the acquisition phase of the MWM task, the PBS-treated mice took significantly longer than the poly-Glu,Tyr-immunized mice to acquire the spatial navigation task, if they were able to acquire it at all. The poly-Glu,Tyr-immunized mice learned to swim to the hidden platform and make use of it as a refuge by climbing onto it and remaining there, as indicated by decreasing latencies in successive trials. In contrast, when the PBS-treated mice encountered the hidden platform, they behaved in an abnormal and maladaptive way. Even when placed directly on the hidden platform after a trial in which they had failed to locate it, these mice quickly walked or jumped off and continued swimming in a haphazard and disorganized manner.

These results indicate that poly-Glu,Tyr has a beneficial effect on psychotic behavior that simulates behavioral abnormalities associated with schizophrenia, and also improved the memory in this animal model.

Section XI

Immunization with Poly-Glu,Tyr Protects Against Nerve Gases

Some metabolic poisons are known to limit their action to the nervous system. These include poisons such as strychnine and curare, as well as the dreaded nerve gases developed for chemical warfare. The exact modes of action of most neurotoxins are not known for certain.

Among the most dangerous chemical weapons are the so-called nerve gases or nerve agents. Nerve agents acquired their name because they affect the transmission of nerve impulses in the nervous system, and have entirely dominated chemical warfare since the Second World War. All nerve agents belong chemically to the group of organophosphorus compounds. They are stable and easily dispersed, highly toxic and have rapid effects both when absorbed through the skin and via respiration.

Exposure to organophosphorus (OP) cholinesterase (ChE) inhibitors causes a progression of toxic signs and symptoms, including hypersecretion, fasciculations, tremors, convulsions, coma, respiratory distress and death. These toxic manifestations are due to hyperactivity of the cholinergic system as a result of inhibition of ChE, in particular, acetylcholinesterase (AChE), and the subsequent increase in the concentration of the neurotransmitter acetylcholine (ACh) at central and peripheral sites. In case of poisoning, immediate therapeutic treatment with an anticholinergic drug, such as atropine sulfate, antagonizes the effects of excess ACh at muscarinic receptor sites, and an oxime, such as TMB4 or HI-6, might be used to reactivate any non-aged inhibited enzyme. However, this treatment (in the absence of an anticonvulsant) is not efficient in prevention or suppression of seizure activity and the related brain damage induced by OP.

Centrally mediated seizures and convulsions are common consequence of exposure to OP anticholinesterase inhibitors. These seizures rapidly progress to status epilepticus and contribute to profound brain injury. Effective management of these seizures is critical for minimization of brain damage.

Sarin (isopropyl methylfluorophosphonate), a colorless and odorless gas, is one of the world's most dangerous chemical warfare agents. Sarin is an extremely toxic substance (lethal dose of 0.5 milligram for an adult) that, like other nerve agents, functions by competitive inhibition of the enzyme AChE, disrupting the nervous system, and over-stimulating muscles and vital organs. It can be inhaled as a gas or absorbed through the skin. In high doses, sarin suffocates its victims by paralyzing the muscles around their lungs.

It was shown in Section I above that poly-Glu,Tyr immunization conferred neuroprotection to RGC loss resulting from retinal glutamate insult. Here we have tested the efficacy of this copolymer as possible neuroprotective agent against sarin-induced brain damage.

For efficacious evaluation of the neuroprotective effect of poly-Glu,Tyr, two models were used in this study. One model consisted of intoxication with 1 LD50 of sarin (90 µg/kg), in the absence of any pharmacological intervention except for the tested compound (Model A). The second model consisted of conventional therapeutic treatment together with an anti-convulsant applied after 30 min of convulsive state (Model B). This treatment reduces the brain damage induced by sarin exposure, but consistent damage is still observed despite the therapeutic intervention. Clinically, in both models A and B, within 2-6 min following sarin exposure, animals develop abnormal electrographic discharges which rapidly transform into electrographic seizure activity (EGSA), with typical manifestation of convulsive behavior. Application of midazolam after 30 min of ongoing convulsions (model B) attenuates EGSA in most cases, but is not sufficient to ameliorate electrocorticographic (EcoG) paradoxical activity and convulsive behavior. More robust picture is presented in model A, accompanied by 30-40% mortality within 24 h post exposure.

Materials and Methods—Section XI

Animals: SPD rats (260-300 g) were housed in groups of five, at 21±2° C. and 50±10% humidity in controlled animal quarters and maintained on a 12 L:12 D, lighting cycle with lights on at 06.00 h.

Materials: Atropin sulfate, pyridostigmine bromide and HI-6 were obtained from Sigma Chemical Company, UK. All compounds were diluted in saline solution. All drug solutions were prepared and injected separately. Midazolam (Dormicum, 5 mg/ml solution) was purchased from Hoffman La Roche, USA. The poly-Glu,Tyr and the PBS solution were prepared on exposure day. The compounds were injected SC in the flank.

Experimental design: The experimental paradigm consisted of two models:

Model A—Exposure to sarin without treatment. In this model, the animals were exposed to sarin (1 $LD_{50}$, 90 µg/kg) without any pharmacological intervention except for the tested neuroprotective agent (poly-Glu,Tyr). Rats were divided into 2 subgroups: 7 days prior to exposure to sarin, one group was immunized with poly-Glu,Tyr and the other received an injection of PBS.

Model B—Sarin exposure and conventional therapeutic regimen. This model consisted of conventional therapeutic treatment together with an anticonvulsant applied after 30 min of convulsive state. It involved pyridostigmine (0.1 mg/kg) and oxime (HI-6, 5 mg/kg) pretreatment 20 min prior to sarin exposure (1.2×LD$_{50}$, 108 µg/kg), administration of atropine (2 mg/kg) one minute after exposure, and additional anticonvulsive treatment with midazolam (1.5 mg/kg) following 30 min of convulsions. Rats were divided into 2 subgroups: 7 days prior to exposure to sarin, one group was immunized with poly-Glu,Tyr and the other received an injection of PBS. This treatment reduces the brain damage induced by sarin exposure, but consistent damage is still observed despite the therapeutic intervention.

Experimental Protocol: Parameters such as clinical status and body weight were monitored for 7 days post-exposure. Animals were weighed on a daily basis, starting 7 days prior to sarin exposure. Clinical evaluation of animal state started following exposure and continued daily throughout the 7-day study. Then, rats were sacrificed by decapitation and the brain was removed for brain histopathology evaluation on day 7.

Clinical score consisted of grading convulsive state following exposure (convulsion score), for 4 h. From day 1 post exposure, animals were scored clinically on a daily basis according to the clinical score presented.

Convulsion score, starting from exposure to 240 min: Convulsion level 1 (mild)=10; Convulsion level 2 (moderate)=20; Convulsion level 3 (severe)=30. Timing factor (post exposure time of convulsions): 1.5 (30'), 2 (60'), 4 (120') and 5 (240'). This procedure is used to properly consider the weight of the time from exposure to a seizure event (the score is proportional to the interval). Animals that recover do not exhibit seizure event after long intervals.

General clinical state, starting on day 1 post exposure until 7 days post exposure: Good clinical state=0; Moderate I: Slight deficiency in tonus and motor activity=10; Moderate II: Reduced tonus and motor activity=20; Severe I: Reduced tonus and no motor activity=30; Severe II: No tonus and no motor activity=60.

Histology: Surviving rats were sacrificed by decapitation one-week post exposure (5-8 animals per group) and their brains were taken for histological evaluation. The brains were rapidly dissected from the skull, fixed in 4% neutral buffered paraformaldehyde at 4° C., and processed routinely for paraffin embedding. Coronal sections, 7 µm thick, were cut serially at the level of the frontal cortex, the striatum and the hippocampus and selected sections were stained with hematoxylin and eosin (H&E) for light microscopy examination. The histological observations were scored using a pathological scoring scale (see below), based on the well-characterized brain damage induced by OP's.

Histological scoring scale: (O)—Normal morphology; (1)—Minor changes (enlargement of ventricles, few pyknotic cells); (2)—Typical OP damage (moderate) in one out of the three vulnerable regions (piriform cortex, hippocampus, thalamus); (3)—Typical OP damage (moderate) in two out of the three vulnerable regions (piriform cortex, hippocampus, thalamus); (4)—Typical OP damage (moderate) in (piriform cortex, hippocampus, thalamus); (5)—Severe damage in at least one degeneration (out of the three), i.e., degeneration over 50% of CA1 cells; (6)—As 5 with minor to moderate damage in additional brain areas (septum, frontal and fronto-parietal cortex, striatum, amygdala); (7)—As 6 with severe damage in the fronto-parietal cortex; (8) As 6 with severe damage in most of the regions, expressed by loss of cells and extensive vacuolization.

Data: Data are presented as MEAN ±SEM.

Example 24

Neuroprotective Effect of Poly-Glu,Tyr in Rats Exposed to Sarin-Model A (LD50 Model)

(i) Mortality: SPD rats (n=16 in each group) were immunized with poly-Glu,Tyr or with PBS 7 days prior to exposure to sarin. In the first 24 h after exposure, mortality was pronounced in model A (8-10 rats died) in the absence of pharmacological intervention (except for the tested poly-Glu, Tyr).

(ii) Body weight was monitored starting on immunization day to eliminate any adverse effect of the tested poly-Glu,Tyr. No adverse effect was observed due to the treatment. As expected, the effect of sarin exposure in this model on body weight was highly pronounced—no full recovery from the insult was observed within 7 days following exposure. No significant differences were found between the experimental subgroups. Decrease in weight grew until day 3 (post exposure), while from day 4 a progressive increase in weight was observed.

(iii) Clinical state: During the seven days following exposure to sarin, the clinical state of the rats was monitored with emphasis on the first 4 h post intoxication time. The observation was based on graded scores for convulsive state. Clinical severity score was then monitored each day starting at 1 day post-exposure up to 7 days post-exposure. The results are summarized in Table 2.

Statistical analysis was performed for the clinical score, separately for the first 4 hours (convulsions) and for the 1-7 days period (motoric behavior) following exposure of the animals to sarin. No significant interactions were found in both analyses between groups and time, involving the whole observation period. Nevertheless, the motoric behavior of the treated animals tended to be better than the control animals at all times measurements (iv) Brain pathology: Animals were sacrificed 7 days post-exposure, their brains were excised and processed for histological evaluation. A severe brain damage was observed in all animals of the control untreated group: they displayed the typical symptoms of sarin toxicity (1 LD$_{50}$), including persistent convulsions. The lesions were most pronounced in the vulnerable regions, i.e, the piriform cortex, thalamus and in the hippocampus. Higher numbers of CA1 cells were affected, showing extensive damage and acidophilic cytoplasm. A well-defined layer of vacuoles was noted in the stratum radiatum area and in the stratum oriens adjacent to the alveus. Necrotic cells were seen also in the CA3 and CA4 regions. In addition to the above-mentioned areas, a laminar degeneration and gliosis were pronounced in the frontal and fronto-parietal cortex. Enlargement of lateral ventricles and ischemic changes were seen in the striatum (not shown).

A Kruskal-Wallis test found significant differences between the various groups in the LD50 model ($\chi^2$ (2)=7.24, $p<0.027$). Specifically, a Mann-Whitney test found a significant ($p<0.006$) difference between the poly-Glu,Tyr treated group and the control group.

Example 25

Neuroprotective Effect of Poly-Glu,Tyr in Rats Exposed to Sarin-Model B (Midazolam Model)

(i) Mortality: SPD rats (n=16 in each group) were immunized with poly-Glu,Tyr or with PBS 7 days prior to exposure to sarin, and received the therapeutic regimen including midazolam as described in Materials and Methods. As expected, mortality was moderate due to the therapeutic intervention (2 rats of each group died within the first 24 h after exposure to sarin).

(ii) Body weight was monitored starting on immunization day, to eliminate any adverse effect of the tested drugs. Animals exhibited normal growing curve following treatment (not shown). As stated before, model B included a limited therapeutic treatment that reduced the impact of the intoxication. In this model, a significant loss of body weight was observed 24 h post-exposure, followed by weight gain later on. Differences in weight were analyzed by a two-way ANOVA for repeated measurement (days), utilizing SPSS software (version 11.0). No significant differences were found between the two subgroups used in this experiment (PBS and poly-Glu,Tyr groups).

(iii) Clinical state: During seven days following sarin exposure, the clinical state of the rats was monitored with emphasis on the first 4 hours post intoxication. Clinical severity score was then monitored each day starting at I day post-exposure up to 7 days post-exposure. The observation comprised graded scores for convulsive state and later on the grading of clinical state. The results are summarized in Table 2.

Two ANOVAS were performed for the clinical score, separately for the first 4 hours (convulsions) and for the 1-7 days period (motoric behavior) following exposure of the animals to sarin. In the first analysis (convulsions), a significant [group×time] interaction was found (F(9/147)=3.15, p<0.002), indicating various differences between the two groups, in different time points. However, no significant differences were found between the groups 30 min following exposure. Two hours after exposure, the severity score of the poly-Glu,Tyr-treated group was significantly (p<0.02-0.001) lower than that of the control group. Also four hours following exposure, the clinical score of the treated group was significantly lower (p<0.001) than that of the control group.

In the second analysis (motoric behavior), a significant [group×time] interaction was found (F(18/294)=2.96, p<0.0001). Specifically, 24 hours following exposure to sarin, the severity score of the treated group was significantly (p<0.001) lower than that of the control group.

(iv) Brain pathology: Typical OP-induced brain lesions were observed in most animals (6/8) of the PBS-treated control group. The damage was most pronounced in the piriform cortex, thalamus and in the hippocampus, brain areas known as susceptible to OP injury. Briefly, laminar degeneration and loss of neurons were noted in the piriform cortex. Cell damage in the hippocampus, mainly in CA1 layer, and vacuolar necrosis in dorso-lateral thalamic nuclei were the major findings observed at the light microscopy level. Due to the midazolam treatment, in this group, following 30 min of convulsions, the damage was less severe than in the $1LD_{50}$ group. Thus, the characteristic lesions, in particular in the hippocampus, were somewhat milder (score 3 compared to 7 out of 8 in the $1LD_{50}$ model) (not shown).

Table 2 summarizes the raw data for the two experimental models: the LD50 (Model A) and the therapeutic model (Model B), as described in Examples 24 and 25 above. For each model, data analysis was performed separately for the two different functional parameters: convulsions and clinical scores. While the convulsions are a direct result of the gas toxicity, the clinical scores are secondary to the toxic environment and show the ability of the tissue to cope with the stress conditions.

The neuroprotective treatment with poly-Glu,Tyr is not expected to have any effect on the convulsions as measured up to 4 hours post trauma. Yet, the treatment reduced clinical deficits as was measured starting one day and up to 7 days post-trauma. In the severe model of LD50, the clinical scores of the treated groups are lower than these of the control group.

TABLE 2

| | LD50 | | Therapeutic model | |
| --- | --- | --- | --- | --- |
| | Control | Poly-Glu, Tyr | Control | Poly-Glu, Tyr |
| | convulsion (h) | | | |
| Hours | | | | |
| 0.5 | 29 | 21 | 29 | 36 |
| 1 | 43 | 36 | 30 | 35 |
| 2 | 82 | 76 | 43 | 32 |
| 4 | 92 | 70 | 43 | 24 |
| | clinical score (days) | | | |
| Days | | | | |
| 1 | 14.6 | 3.5 | 17.9 | 10.0 |
| 2 | 10.5 | 6.4 | 1.8 | 1.5 |
| 3 | 10.0 | 8.1 | 0.0 | 0.0 |
| 4 | 13.8 | 4.4 | 0.0 | 0.0 |
| 5 | 10.0 | 5.0 | 0.0 | 0.0 |
| 6 | 11.9 | 8.0 | 0.0 | 0.0 |
| 7 | 10.8 | 5.0 | 0.0 | 0.0 |

Section XII

Cardioprotective Immunity: Effect of Immunization With Poly-Glu,Tyr in an Animal Model of Myocardial Infarction As described hereinbefore, accumulating results in our laboratory have led us to formulate the concept that autoimmunity is a physiological T cell-based repair mechanism directed against abundant antigens residing in the site of CNS damage, and that autoimmune disease is an outcome of the body's failure to control such autoimmunity (Moalem et al., 1999; Hauben et al., 2000a, 2000b, 2001a, 2001b; Kipnis et al., 2002a, 2002b; Yoles et al., 2001; Mizrahi et al., 2002). This implies that autoimmunity is basically beneficial, and becomes destructive only when its control mechanism is malfunctioning. According to this view, the autoantigens that participate in disease and in protection are the same, although their epitopes might differ. Thus, in order to achieve protection without risk of destructive autoimmunity, at least in organs that might develop autoimmune disease, it is possible to boost the beneficial autoimmune response in a well-controlled way by using a peptide which, though derived from a potentially pathogenic self-protein, is not itself pathogenic (Mizrahi et al., 2002). The selected peptide should be modified, so that its full protective benefit can be derived even in individuals with a genetically determined tendency to autoimmune disease development (Hauben et al., 2001a, 2001b; Mizrahi et al., 2002).

Based on the concept of protective autoimmunity, we propose that patients with cardiovascular disease will benefit from a therapeutic measure with peptides derived from self-proteins known to be abundant in the heart. As an alternative vaccine, it is possible to use an antigen such as poly-Glu,Tyr, which reduces the inhibition from a wide range of self-reactive T cells. This approach in the heart becomes even more appealing in light of recent publications viewing cardiac diseases as a reflection of a fine line between innate and inappropriate immune responses (Smith et al., 2002; Mann, 2001).

Materials and Methods—Section XII

Rat model of myocardial infarction. Myocardial infarction (MI) is surgically induced in anesthetized male SPD rats (8-week-old, 200-240 g): the chest is opened by left thoracotomy, the pericardium is removed and the left coronary artery is permanently occluded with intramural stitch, approximately 2 mm distal to its aortic origin (Etzion et al., 2001).

Immunization. Rats are immunized with 5 mg of cardiac homogenate, or 0.5 mg or 0.25 mg of poly-Glu,Tyr in PBS. Control groups are injected with PBS.

Echocardiography to evaluate remodeling and contractility. Transthoratic echocardiogarphy is performed on all animals 1-2 day after the MI and 30 days after the MI. Briefly, rats are anesthetized with 50 mg/kg ketamine and 10 mg/kg xylazine. The chest is shaved, and the rats are placed supine. Echocardiograms are performed with a commercially available echocardiography system equipped with 7.5-MHz phased-array transducer (Hewlett-Packard). The transducer is positioned on the left anterior side of the chest after the precordium is shaved. The heart is first imaged in the 2-dimensional mode in the parasternal long- and short-axis views of the LV. By the use of these views, the M-mode cursor is positioned perpendicular to the ventricular septum and posterior wall; M-mode images are then obtained at the level below the tip of the mitral valve leaflets at the level of the papillary muscles. Care is taken to avoid excessive pressure. Posterior wall thickness and LV internal dimensions are measured according to the leading edge method of the American Society of Echocardiography: maximal LV end-diastolic dimension (at the time of maximal cavity dimension), minimal LV end-systolic dimension (at the time of maximum anterior motion of the posterior wall), and fractional shortening as a measure of systolic function, which is calculated as FS (%)=[(LVIDd-LVIDs)/LVIDd]×100, where LVID is LV internal dimension, s is systole, and d is diastole. To further validate these measurements and to determine the accuracy and reproducibility of the technique, we carry out a reproducibility study in normal rats. All measurements are averaged for 3 consecutive cardiac cycles and are made by an experienced technician who is blinded to the treatment group (Etzion et al., 2001).

Histological examinations. Rats are sacrificed, after four weeks, with an overdose of ketamine and xylazine followed by KCl to ensure maximal myocardial relaxation. The hearts are then perfused with formaldehyde for 30 minutes and then embedded in paraffin, sectioned into 5 µm slices 5 mm from the heart's apex, stained for hematoxylin and eosin, and histological examination is carried out.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Adamec R E, P. Burton, T. Shallow, J. Budgell. Unilateral block of NMDA receptors in the amygdala prevents predator stress-induced lasting increases in anxiety-like behavior and unconditioned startle—effective hemisphere depends on the behavior. *Physiol. Behav.* 65: 739-51 (1999).

Ahlander, M., Misane, I., Schott, P. A. & Ogren, S. O. A behavioral analysis of the spatial learning deficit induced by the NMDA receptor antagonist MK-801 (dizocilpine) in the rat. *Neuropsychopharmacology* 21: 414-26 (1999).

Angelov D N, Waibel S, Guntinas-Lichius O, Lenzen M, Neiss W F, Tomov T L, Yoles E, Kipnis J, Schori H, Reuter A, Ludolph A, Schwartz M. Therapeutic vaccine for acute and chronic motor neuron diseases: implications for amyotrophic lateral sclerosis. *Proc Natl Acad Sci USA* 100(8): 4790-5 (2003).

Bakalash, S., Kipnis, J., Yoles, E. & Schwartz, M. Resistance of retinal ganglion cells to an increase in intraocular pressure is immune-dependent. *Invest. Opthalmol. Vis. Sci.* 43: 2648-2653 (2002).

Basso, D M, Beattie, M S and Bresnahan, J C, A sensitive and reliable locomotor rating scale for open field testing in rats, *J. Neurotrauma* 12:1-21 (1995).

Basso D M, Beattie, M S and Bresnahan, J C, Graded histological and locomotor outcomes after spinal cord contusion using the NYU weight-drop device versus transection, *Exp. Neurol.* 139(2): 244-256 (1996).

Ben-Nun A, Wekerle H, Cohen I R. The rapid isolation of clonable antigen-specific T lymphocyte lines capable of mediating autoimmune encephalomyelitis, *Eur. J. Immunol.* 11(3):195-199 (1981).

Cady C T, Lahn M, Vollmer M, Tsuji M, Seo S J, Reardon C L, O'Brien R L, Born W K. Response of murine gamma delta T cells to the synthetic polypeptide poly-Glu50Tyr50. *J Immunol.* 165(4):1790-8 (2000.

Cohen H, Kaplan Z, Kotler M, Mittelman I, Osher Y, Bersudsky Y. Impaired heart rate variability in euthymic bipolar patients. *Bipolar Disord.* 5: 138-43 (2003).

Debre P, Kapp J A, Dorf M E, Benacerraf B. Genetic control of specific immune suppression. II. H-2-linked dominant genetic control of immune suppression by the random copolymer L-glutamic acid 50-L-tyrosine-50(GT), *J. Exp. Med.* 142(6):1447-54 (1975).

de Groot J, W. J. Boersma, J. W. Scholten, J. M. Koolhaas, Social stress in male mice impairs long-term antiviral immunity selectively in wounded subjects. *Physiol. Behav.* 75L 277-85 (2002).

Dhabhar F S, B S McEwen, Acute stress enhances while chronic stress suppresses cell-mediated immunity in vivo: a potential role for leukocyte trafficking. *Brain Behav. Immun.* 11: 286-306 (1997):

Dummer W, Niethammer A G, Baccala R, Lawson B R, Wagner N, Reisfeld R A, Theofilopoulos AN. T cell homeostatic proliferation elicits effective antitumor autoimmunity. *J Clin Invest* 110: 185-192 (2002).

Etzion S, Battler A, Barbash I M, Cagnano E, Zarin P, Granot Y, Kedes L H, Kloner R A, Leor J. Influence of embryonic cardiomyocyte transplantation on the progression of heart failure in a rat model of extensive myocardial infarction. *J Mol Cell Cardiol* 33: 1321-1330 (2001).

Griesbach, G. S., Hu, D. & Amsel, A. Effects of MK-801 on vicarious trial-and-error and reversal of olfactory discrimination learning in weanling rats. *Behav Brain Res* 97: 29-38 (1998).

Hauben E., Nevo, U., Yoles, E., Moalem, G., Agranov, E., Mor, F., Akselrod, S., Neeman, M., Cohen, I. R., and Schwartz, M. Autoimmune T cells as potential neuroprotective therapy for spinal cord injury. *Lancet* 355:286-287 (2000a).

Hauben, E., Butovsky, O., Nevo, U., Yoles, E., Moalem, G., Agranov, E., Mor, F., Leibowitz-Amit, R., Pevsner, E., Akselrod, S., Neeman, M., Cohen, I. R., & Schwartz, M. Passive or active immunization with myelin basic protein promotes recovery from spinal cord contusion. *J. Neurosci.* 20: 6421-6430 (2000b).

Hauben, E., Agranov, E., Gothilf, A., Nevo, U., Cohen, A., Smirnov, I., Steinman, L., & Schwartz, M. Posttraumatic therapeutic vaccination with modified myelin self-antigen prevents complete paralysis while avoiding autoimmune disease. *J. Clin. Invest.* 108: 591-599 (2001a).

Hauben, E., Ibarra, A., Mizrahi, T., Barouch, R., Agranov, E., and Schwartz, M. Vaccination with a Nogo-A-derived peptide after incomplete spinal-cord injury promotes recovery via a T-cell-mediated neuroprotective response: comparison with other myelin antigens. *Proc Natl Acad Sci USA* 98:15173-15178 (2001b).

Hickey W F, Hsu B L, Kimura H., T-lymphocyte entry into the central nervous system, *J. Neurosci. Res.* 28(2):254-260 (1991).

Hirschberg, D. L., Moalem, G., He, J., Mor, F., Cohen, I. R., and Schwartz, M. Accumulation of passively transferred primed T cells independently of their antigen specificity following central nervous system trauma. *J. Neuroimmunol.* 89(1-2):88-96 (1998).

Jin K, Minami M, Lan J Q, Mao X O, Batteur S, Simon R P, Greenberg D A. Neurogenesis in dentate subgranular zone and rostral subventricular zone after focal cerebral ischemia in the rat. *Proc Natl Acad Sci USA* 98: 4710-4715 (2001).

Kipnis J, Yoles E, Porat Z, Cohen A, Mor F, Sela M, Cohen I R, Schwartz M. T cell immunity to copolymer 1 confers neuroprotection on the damaged optic nerve: possible therapy for optic neuropathies. *Proc Natl Acad Sci USA* 97: 7446-7451 (2000).

Kipnis, J, Yoles E, Schori H, Hauben E, Shaked I, Schwartz M. Neuronal survival after CNS insult is determined by a genetically encoded autoimmune response. *J. Neurosci.* 21: 4564-4571 (2001).

Kipnis, J., Mizrahi T. Hauben E., Shaked I., Shevach E., and Schwartz, M. Neuroprotective autoimmunity: naturally occurring $CD4^+CD25^+$ regulatory T cells suppress the ability to withstand injury to the central nervous system. *Proc Natl Acad Sci USA* 99: 15620-15625 (2002a).

Kipnis, J., Yoles, E., Mizrahi, T., Ben-Nur, A. & Schwartz, M. Myelin specific Th1 cells are necessary for post-traumatic protective autoimmunity. *J Neuroimmunol* 130: 78 (2002b).

Kong, J. and Xu, Z. Massive mitochondrial degeneration in motor neurons triggers the onset of amyotrophic lateral sclerosis in mice expressing a mutant SOD1 *J. Neuroscience* 18: 3241-3250 (1998).

Mangiarini L, Sathasivam K, Seller M, Cozens B, Harper A, Hetherington C, Lawton M, Trottier Y, Lehrach H, Davies S W, Bates G P., Exon 1 of the HD gene with an expanded CAG repeat is sufficient to cause progressive neurological phenotype in transgenic mice, *Cell* 87(3):493-506 (1996).

Mann, D. L. Tumor necrosis factor and viral myocarditis: the fine line between innate and inappropriate immune responses in the heart. *Circulation* 103: 626-629 (2001).

McEwen B S, Protective and damaging effects of stress mediators: the good and bad sides of the response to stress. *Metabolism* 51: 2-4 (2002).

Meldrum B S, Glutamate as a neurotransmitter in the brain: review of physiology and pathology, *J. Nutr.* 130:(4S Suppl): 1007S-1015S (2000).

Mizrahi, T., Hauben, E. & Schwartz, M. The tissue-specific self-pathogen is the protective self-antigen: the case of uveitis. *J Immunol* 169: 5971-5977 (2002).

Moalem, G., Leibowitz-Amit R, Yoles E, Mor F, Cohen I R, Schwartz M. Autoimmune T cells protect neurons from secondary degeneration after central nervous system axotomy. *Nat Med* 5: 49-55 (1999).

Nakamura K., Kitani, A. & Strober, W. Cell contact-dependent immunosuppression by CD4(+)CD25(+) regulatory T cells is mediated by cell surface-bound transforming growth factor beta. *J Exp Med* 194: 629-644 (2001).

Ota K, Matsui M, Milford E L, Mackin G A, Weiner H L, Hafler DA, T-cell recognition of an immunodominant myelin basic protein epitope in multiple sclerosis, *Nature* 346(6280):183-187 (1990).

Pette M, Fujita K, Kitze B, Whitaker J N, Albert E, Kappos L, Wekerle H., Myelin basic protein-specific T lymphocyte lines from MS patients and healthy individuals, *Proc. Natl. Acad. Sci. USA* 87(2):7968-7972 (1990).

Pitt D, Werner P, Raine CS. Glutamate excitotoxicity in a model of multiple sclerosis, *Nat Med,* 6:67-70 (2000).

Sakaguchi S., Sakaguchi, N., Asano, M., Itoh, M. & Toda, M. Immunologic self-tolerance maintained by activated T cells expressing IL-2 receptor alpha-chains (CD25). Breakdown of a single mechanism of self-tolerance causes various autoimmune diseases. *J Immunol* 155: 1151-1164 (1995).

Sakaguchi S, Sakaguchi N, Shimizu J, Yamazaki S, Sakihama T, Itoh M, Kuniyasu Y, Nomura T, Toda M, Takahashi T. Immunologic tolerance maintained by CD25$^+$CD4$^+$ regulatory T cells: their common role in controlling autoimmunity, tumor immunity, and transplantation tolerance. *Immunol Rev.* 182: 18-32 (2001).

Schori, H., Yoles, E. & Schwartz, M. T-cell-based immunity counteracts the potential toxicity of glutamate in the central nervous system. *J Neuroimmunol* 119: 199-204 (2001a).

Schori H, Kipnis J, Yoles E, WoldeMussie E, Ruiz G, Wheeler L A, Schwartz M., Vaccination for protection of retinal ganglion cells against death from glutamate cytotoxicity and ocular hypertension: Implications for glaucoma. *Proc Natl Acad Sci USA* 98: 3398-3403 (2001b).

Schori H, Yoles E, Wheeler L A, Raveh T, Kimchi A, Schwartz M. Immune-related mechanisms participating in resistance and susceptibility to glutamate toxicity. *Eur J Neurosci.* 16(4): 557-64 (2002).

Schwartz, M. and Kipnis, J. Protective autoimmunity: regulation and prospects for vaccination after brain and spinal cord injuries. *Trends Mol Med* 7: 252-8 (2001).

Schwartz, M. & Kipnis, J. Autoimmunity on alert: naturally occurring regulatory CD4(+)CD25(+) T cells as part of the evolutionary compromise between a 'need' and a 'risk'. *Trends Immunol* 23: 530-534 (2002).

Seo S J, Lahn M, Cady C, Vollmer M, O'Brien R L, Born W K, Reardon C L. Activation of murine epidermal V gamma 5/V delta 1-TCR(+) T cell lines by Glu-Tyr polypeptides. *J Invest Dermatol.* 116:880-5 (2001).

Shevach EM CD4$^+$CD25$^+$ suppressor T cells: more questions than answers. *Nat Rev Immunol.* 2:389-400 (2002).

Shevach E M, McHugh R S, Thornton A M, Piccirillo C, Natarajan K, Margulies D H. Control of autoimmunity by regulatory T cells. *Adv Exp Med Biol* 490: 21-32 (2001).

Smith, R. M., Suleman, N., McCarthy, J. & Sack, M. N. Classic ischemic but not pharmacologic preconditioning is abrogated following genetic ablation of the TNF-alpha gene. *Cardiovasc Res* 55: 553-560 (2002).

Thornton, A. M. & Shevach, E. M. CD4$^+$CD25$^+$ immunoregulatory T cells suppress polyclonal T cell activation in vitro by inhibiting interleukin 2 production. *J Exp Med* 188: 287-296 (1998).

Thornton, A. M. & Shevach, E. M. Suppressor effector function of CD4$^+$CD25$^+$ immunoregulatory T cells is antigen nonspecific. *J Immunol* 164: 183-190 (2000).

Vidovic D, Klein J, Nagy Z A. Recessive T cell response to poly (Glu50Tyr50) possibly caused by self tolerance. *J Immunol.* 134(6):3563-8 (1985)

Vidovic D, Matzinger P. Unresponsiveness to a foreign antigen can be caused by self-tolerance. *Nature* 336(6196): 222-5 (1988).

Whishaw, I. Q. & Auer, R. N. Immediate and long-lasting effects of MK-801 on motor activity, spatial navigation in a swimming pool and EEG in the rat. *Psychopharmacology (Berl)* 98: 500-7 (1989).

Yoles E, Schwartz M. Degeneration of spared axons following partial white matter lesion: implications for optic nerve neuropathies. *Exp Neurol.* 153(1):1-7 (1998).

Yoles E, Hauben E, Palgi O, Agranov E, Gothilf A, Cohen A, Kuchroo V, Cohen IR, Weiner H, Schwartz M. Protective autoimmunity is a physiological response to CNS trauma. *J. Neurosci.* 21: 3740-3748. (2001).

What is claimed is:

1. A method for down-regulating the suppressive activity of CD4$^+$CD25$^+$ T$_{reg}$ cells at the site of a lesion in the central or peripheral nervous system, comprising administering to a subject in need, an amount of poly-Glu,Tyr effective to down-regulate the suppressive activity of CD4$^+$CD25$^+$ T$_{reg}$ cells at the lesion site.

2. The method in accordance with claim 1, wherein the subject in need is one suffering from the neurodegenerative effects of an injury, disease, disorder or condition that has caused a primary neuronal damage lesion in the CNS or PNS of that individual.

3. The method in accordance with claim 2, wherein the subject in need is one suffering from an injury that has caused a primary neuronal damage lesion.

4. The method in accordance with claim 3, wherein said injury is selected from the group consisting of spinal cord injury, closed head injury, blunt trauma, penetrating trauma, hemorrhagic stroke, ischemic stroke, cerebral ischemia, optic nerve injury and injury caused by tumor excision.

5. The method in accordance with claim 4, wherein said injury is spinal cord injury.

6. The method in accordance with claim 4, wherein said injury is ischemic stroke.

7. The method in accordance with claim 2, wherein said injury, disease, disorder or condition is a neurodegenerative disease, disorder or condition associated with the eye.

8. The method in accordance with claim 7, wherein said neurodegenerative disease, disorder or condition associated with the eye is non-arteritic optic neuropathy or a disease associated with elevated intraocular pressure.

9. The method in accordance with claim 1, wherein the subject in need is one having neurodegeneration at a lesion caused or exacerbated by glutamate toxicity.

10. The method in accordance with claim 9, wherein the lesion caused or exacerbated by glutamate toxicity is associated with a neurodegenerative disease, disorder or condition.

11. The method in accordance with claim 9, wherein the lesion caused or exacerbated by glutamate toxicity is associated with a peripheral neuropathy.

* * * * *